(12) United States Patent
Kovach et al.

(10) Patent No.: US 8,455,688 B2
(45) Date of Patent: Jun. 4, 2013

(54) HDAC INHIBITORS

(75) Inventors: John S. Kovach, East Setauket, NY (US); Francis Johnson, Setauket, NY (US)

(73) Assignee: Lixte Biotechnology, Inc., East Setauket, NY (US)

( * ) Notice: Subject to any disclaimer, the term of this patent is extended or adjusted under 35 U.S.C. 154(b) by 0 days.

(21) Appl. No.: 13/426,417

(22) Filed: Mar. 21, 2012

(65) Prior Publication Data
US 2012/0178783 A1 Jul. 12, 2012

Related U.S. Application Data

(62) Division of application No. 12/286,769, filed on Oct. 1, 2008, now Pat. No. 8,143,445.

(60) Provisional application No. 61/063,965, filed on Feb. 6, 2008, provisional application No. 61/008,673, filed on Dec. 21, 2007, provisional application No. 60/997,338, filed on Oct. 1, 2007.

(51) Int. Cl.
C07C 233/65 (2006.01)
A61K 31/16 (2006.01)

(52) U.S. Cl.
USPC ........... 564/158; 564/154; 546/309; 514/352; 514/616

(58) Field of Classification Search
USPC .................. 564/154, 158; 546/309; 514/616, 514/352
See application file for complete search history.

(56) References Cited

U.S. PATENT DOCUMENTS

| | | | |
|---|---|---|---|
| 2,957,906 A | 10/1960 | Erickson et al. | |
| 3,022,268 A * | 2/1962 | Armitage et al. | 524/291 |
| 4,143,054 A | 3/1979 | Sprague | |
| 4,218,478 A | 8/1980 | Omura et al. | |
| 4,298,752 A | 11/1981 | Dauben et al. | |
| 4,410,681 A * | 10/1983 | Prindle | 528/98 |
| 4,463,015 A | 7/1984 | Haslanger et al. | |
| 4,614,825 A | 9/1986 | Snitman et al. | |
| 4,654,355 A | 3/1987 | Nakane et al. | |
| 4,690,918 A | 9/1987 | Beppu et al. | |
| 4,816,579 A | 3/1989 | Thottathil et al. | |
| 4,851,423 A | 7/1989 | Girijavallabhan et al. | |
| 4,851,553 A | 7/1989 | Thottathil | |
| 5,266,710 A | 11/1993 | Patel et al. | |
| 5,326,898 A | 7/1994 | Chandraratna | |
| 5,763,647 A | 6/1998 | Ohtani et al. | |
| 5,770,382 A | 6/1998 | Hwang et al. | |
| 5,925,651 A | 7/1999 | Hutchinson | |
| 5,968,965 A | 10/1999 | Dinsmore et al. | |
| 6,222,055 B1 | 4/2001 | Wolter et al. | |
| 6,632,823 B1 | 10/2003 | Vernier et al. | |
| 6,696,483 B2 | 2/2004 | Singh | |
| 6,706,762 B1 | 3/2004 | Evans et al. | |
| 6,777,217 B1 | 8/2004 | Schreiber et al. | |
| 6,949,624 B1 | 9/2005 | Liu et al. | |
| 7,067,551 B2 | 6/2006 | Remiszewski et al. | |
| 7,154,002 B1 | 12/2006 | Bressi et al. | |
| 7,998,957 B2 | 8/2011 | Kovach et al. | |
| 8,058,268 B2 | 11/2011 | Kovach | |
| 8,143,445 B2 * | 3/2012 | Kovach et al. | 564/154 |
| 8,227,473 B2 | 7/2012 | Kovach et al. | |
| 2002/0115826 A1 | 8/2002 | Delorme et al. | |
| 2002/0147345 A1 | 10/2002 | El Tayer et al. | |
| 2002/0177692 A1 | 11/2002 | Bartel et al. | |

(Continued)

FOREIGN PATENT DOCUMENTS

| | | |
|---|---|---|
| EP | 1443967 | 1/2007 |
| JP | 2007-511528 | 5/2007 |

(Continued)

OTHER PUBLICATIONS

Tanaka et al, Chem. Pharm. Bull., 1962, 10, 556-62.*
Kijima et al. "Trapoxin, an Antitumor Cyclic Tetrapeptide, Is an Irreversible Inhibitor of Mammalian Histone Deacetylase" J. Biol. Chem., 268(30), pp. 22429-22435.
Kim et al. (199) "Selective Induction of Cyclin-Dependent Kinase Inhibitors and Their Roles in Cell Cycle Arrest Caused by Trichostatin A, an Inhibitor of Histone Deacetylase" Ann. N.Y. Acad. Sci., 886, pp. 200-203.

(Continued)

*Primary Examiner* — Shailendra Kumar
(74) *Attorney, Agent, or Firm* — John P. White; Gary J. Gershik; Cooper & Dunham LLP

(57) ABSTRACT

This invention provides the compound having the structure

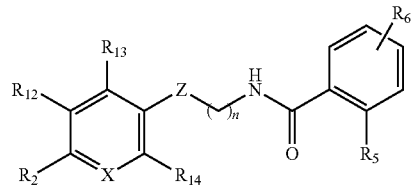

wherein
n is 1-10;
X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;
Z is

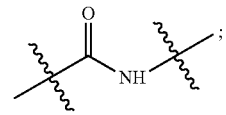

$R_2$ is H or $NR_3R_4$, wherein $R_3$ and $R_4$ are each independently H, $C_1$-$C_6$ alkyl, or $C_3$-$C_8$ cycloalkyl;
$R_5$ is OH or SH; and
$R_6$, $R_{12}$, $R_{13}$, and $R_{14}$ are each independently H, OH, SH, F, Cl, $SO_2R_{15}$, $NO_2$, trifluoromethyl, methoxy, or CO—$R_{15}$,
wherein $R_{15}$ is alkyl, alkenyl, alkynyl, $C_3$-$C_8$ cycloalkyl, or aryl, or
a salt of the compound,
which is useful in the treatment of tumors.

20 Claims, 35 Drawing Sheets

U.S. PATENT DOCUMENTS

| | | |
|---|---|---|
| 2003/0162186 A1 | 8/2003 | Bejanin et al. |
| 2004/0053996 A1 | 3/2004 | Gesing et al. |
| 2004/0087657 A1 | 5/2004 | Richon et al. |
| 2004/0106141 A1 | 6/2004 | Mischel et al. |
| 2004/0122101 A1 | 6/2004 | Miller et al. |
| 2004/0161475 A1 | 8/2004 | Ellison et al. |
| 2004/0197888 A1 | 10/2004 | Armour et al. |
| 2004/0209934 A1 | 10/2004 | McCluskey et al. |
| 2004/0253637 A1 | 12/2004 | Buechler et al. |
| 2005/0014839 A1 | 1/2005 | Kozikowski et al. |
| 2005/0020831 A1 | 1/2005 | Inman et al. |
| 2005/0054626 A1 | 3/2005 | Carter et al. |
| 2005/0119229 A1 | 6/2005 | Ammermann et al. |
| 2005/0136090 A1 | 6/2005 | Falotico et al. |
| 2005/0171202 A1 | 8/2005 | Graupner et al. |
| 2005/0203082 A1 | 9/2005 | Hsu et al. |
| 2005/0215526 A1 | 9/2005 | Hulme et al. |
| 2005/0222013 A1 | 10/2005 | Jung et al. |
| 2005/0277583 A1 | 12/2005 | Yoshida et al. |
| 2006/0030616 A1 | 2/2006 | McCluskey et al. |
| 2006/0117994 A1 | 6/2006 | Ryu et al. |
| 2006/0134682 A1 | 6/2006 | Robert et al. |
| 2006/0167103 A1 | 7/2006 | Bacopoulos et al. |
| 2006/0235231 A1 | 10/2006 | Joel et al. |
| 2006/0264415 A1 | 11/2006 | Leit de Moradei et al. |
| 2007/0004771 A1 | 1/2007 | Lee et al. |
| 2007/0010669 A1 | 1/2007 | Breslow et al. |
| 2007/0049576 A1 | 3/2007 | Barlow et al. |
| 2007/0135365 A1 | 6/2007 | Tanizawa et al. |
| 2007/0135433 A1 | 6/2007 | Dean et al. |
| 2007/0155751 A1 | 7/2007 | Paruch et al. |
| 2007/0197550 A1 | 8/2007 | Georgopapadakou et al. |
| 2007/0208166 A1 | 9/2007 | Baly et al. |
| 2007/0213330 A1 | 9/2007 | Delorme et al. |
| 2008/0132503 A1 | 6/2008 | Moradei et al. |
| 2008/0214569 A1 | 9/2008 | Zhuang et al. |
| 2009/0012066 A1 | 1/2009 | Izumo et al. |
| 2009/0018142 A9 | 1/2009 | Zhuang et al. |
| 2009/0035292 A1* | 2/2009 | Kovach et al. ............... 424/94.6 |
| 2009/0036309 A1 | 2/2009 | Kovach et al. |
| 2009/0143445 A1 | 6/2009 | Kovach et al. |
| 2010/0029484 A1 | 2/2010 | Kovach et al. |
| 2010/0029640 A1 | 2/2010 | Kovach et al. |
| 2010/0029683 A1 | 2/2010 | Kovach et al. |
| 2011/0287537 A1 | 11/2011 | Kovach |
| 2012/0135522 A1 | 5/2012 | Kovach |

FOREIGN PATENT DOCUMENTS

| | | |
|---|---|---|
| JP | 2007-514665 | 6/2007 |
| WO | WO 2005-018673 | 3/2005 |
| WO | WO 2005-049084 | 6/2005 |
| WO | WO 2005-054257 | 6/2005 |
| WO | WO 2005-058280 | 6/2005 |
| WO | WO 2005-074941 | 8/2005 |
| WO | WO 2006-023603 | 3/2006 |
| WO | WO 2006-129105 | 12/2006 |
| WO | WO 2007-014029 | 2/2007 |
| WO | WO 2007-021682 | 2/2007 |
| WO | WO 2007-092414 | 8/2007 |
| WO | WO 2007-118137 | 10/2007 |
| WO | WO 2008-097561 | 8/2008 |
| WO | WO 2009-020565 | 2/2009 |
| WO | WO 2009/045440 | 4/2009 |
| WO | WO 2010-014141 | 2/2010 |
| WO | WO 2010/014220 | 2/2010 |
| WO | WO 2010/014254 | 2/2010 |
| WO | WO 2010/147612 | 12/2010 |

OTHER PUBLICATIONS

Korzus et al. (2004) "CBP Histone Acetyltransferase Activity Is a Critical Component of Memory Consolidation" Neuron, vol. 42, pp. 961-972.

Kozikowski et al. (2007) "Functional differences in epigenetic modulators-superiority of mercaptoacetamide-based histone deacetylase inhibitors relative to hydroxamates in cortical neuron neuroprotection studies" J. Med. Chem., 50, pp. 3054-3061.

Kwon et al. "Depudecin induces morphological reversion of transformed fibroblasts via the inhibition of histone deacetylase" Proc. Natl. Acad. Sci. USA, 95(7), pp. 3356-3361.

Langley et al. (2008) Pulse inhibition of histone deacetylases induces complete resistance to oxidative death in cortical neurons without toxicity and reveals a role for cytoplasmic p21waf1/cip1 in cell cycle-independent neuroprotection J. Neurosci., 28(1), pp. 163-176.

Levenson et al. (2004) "Regulation of Histone Acetylation during memory formation in the hippocampus" J. Biol. Chem., 29(39), pp. 40545-40559.

Lin et al (1998) "Role of the histone deacetylase complex in acute promyelocytic leukaemia" Nature, 391(6669), pp. 811-814.

Price et al. (2007) "Histone deacetylase inhibitors; an analysis of recent patenting activity" Expert Opin. Ther. Patents, 17(7), pp. 745-765.

Richon et al. "A class of hybrid polar inducers of transformed cell differentiation inhibits histone deacetylases" Proc. Natl. Acad. Sci. USA, 95(6), pp. 3003-3007.

Riester et al. (2007) "Histone deacetylase inhibitors-turning epigenic mechanisms of gene regulation into tools of therapeutic intervention in malignant and other diseases" Appl. Microbial. Biotechnol., vol. 75, pp. 499-514.

Saito et al. "A synthetic inhibitor of histone deacetylase, MS-27-275, with marked in vivo antitumor activity against human tumors" Proc. Natl. Acad. Sci. USA, 96(8), pp. 4592-4597.

Smith, W. L., et al. (2002) "Histone deacetylase inhibitors enhance *Candida albicans* sensitivity to azoles and related antifungals: correlation with reduction in CDR and ERG upregulation", Antimicrob. Agents Chemother., 46(11), pp. 3532-3539.

Song et al. (2002) "Synthesis and Biological Properties of Amino Acid Amide Ligand-Based Pyridinioalkanoyl Thioesters as Anti-HIV Agents" Bioorganic and Medicinal Chem., 10(5), pp. 1263-1273.

Suzuki et al. "Synthesis and Histone Deacetylase Inhibitory Activity of New Benzamide Derivatives" J. Med. Chem., 42(15), pp. 3001-3003.

Sweatt, J. D. (2007) "Behavioural neuroscience: Down memory lane" Nature, 447, pp. 151-152.

Warrell, Jr. et al. (1998) "Therapeutic Targeting of Transcription in Acute Promyelocytic Leukemia by Use of an Inhibitor of Histone peacetylase" J. Natl. Cancer Inst., 90, pp. 1621-1625.

Yoshida et al. (1999) "Trichostatin and Leptomycin Inhibition of Histone Deacetylation and Signal-Dependent Nuclear Export" Ann. N.Y. Acad. Sci., 886, pp. 23-35.

McCluskey et al. (2000) "Anhydride Modified Cantharidin Analogues: Synthesis, Inhibition of Protein Phosphatases 1 and 2A and Anticancer Activity" Bioorg. Med. Chem. Lett., 10, pp. 1687-1690.

McCluskey et al. (2000) "Anhydride modified cantharidin analogues. Is ring opening important in the inhibition of protein phosphatase 2A?" Eur. J. Med. Chem., 35, pp. 957-964.

Levesque. Reduction of L-DOPA-induced dyskinesias by retinoid agonists: a new way to improve Parkinson's disease treatment. The Parkinson Aliance, 2004 Pilot Study Grants, abstract only.

Paez et al. "PI3K/PTEN/AKT pathway," Signal Transduction in Cancer, Kluwer Academic Publishers, 2006, vol. 115, pp. 1-28.

Sahin et al. "Retinoic Acid Isomers Protect Hippocampal Neurons From Amyloid-beta Induced Neurodegeneration." Neurotoxicity Res., 2005, vol. 7(3), pp. 243-250.

Avila et al. "Tau phosphorylation, aggregation, and cell toxicity." J. Biomedicine and Biotechnology, Hinwadi Publishing Corporation, vol. 2006, pp. 1-5.

Isfort et al., "Helical Complexes Containing Diamide-Bridged Benzene-o-dithiolate/Catecholato Ligands", Chemistry—A European Journal, vol. 13, No. 8, 2006, 2344-2357.

Kreickmann et al., "Metallosupramolecular Chemistry with Bis (benzene-o-dithiolato) Ligands", J. Am. Chem. Soc., vol. 128, No. 36, 2006, p. 11808-11819.

Zhao et al., "2,3-Dihydro-6,7-dihydroxy-1 H-isoindol-1-one Based HIV-1 Integrase Inhibitors"J. Med. Chem., vol. 51, No. 2, pp. 251-259.

Official Action issued Jun. 26, 2012 in connection with Eurasian Patent Application No. 201070428, filed Apr. 30, 2010.

Official Action issued Aug. 15, 2012 in connection with Mexican Patent Application No. MX/a/2010/003417, filed Mar. 26, 2010.

First Official Action issued Sep. 25, 2012 in connection with Chinese Patent Application No. 200880115815.7, filed May 12, 2010.

International Search Report in connection with PCT/US2007/003095, issued Feb. 14, 2008.

International Preliminary Report on Patentability in connection with PCT/US2007/003095, issued Aug. 12, 2008.

Written Opinion in connection with PCT/US2007/003095, issued Feb. 14, 2008.

Notification of Transmittal of the International Search Report and the Written Opinion of the International Searching Authority, or the Declaration in connections with PCT/US07/03095, issued Feb. 14, 2008.

Notification Concerning Transmittal of International Preliminary Report on Patentability in connection with PCT/US07/03095, issued Aug. 21, 2008.

Notification of Transmittal of the International Search Report and the Written Opinion of the International Searching Authority, or the Declaration in connection with PCT/US08/01549, issued May 16, 2008.

International Search Report in connection with PCT/US08/01549, issued May 16, 2008.

Written Opinion in connection with PCT/US08/01549, issued May 16, 2008.

Notification of Transmittal of the International Search Report and the Written Opinion of the International Searching Authority, or the Declaration in connection with PCT/US08/09330, issued Nov. 4, 2008.

International Search Report in connection with PCT/US08/09330, issued Nov. 4, 2008.

Written Opinion in connection with PCT/US08/09330, issued Nov. 4, 2008.

Notification of Transmittal of the International Search Report and the Written Opinion of the International Searching Authority, or the Declaration in connection with PCT/US08/11367, issued Dec. 12, 2008.

International Search Report in connection with PCT/US08/11367, issued Dec. 12, 2008.

Written Opinion in connection with PCT/US08/11367, issued Dec. 12, 2008.

Supplemental European Search Report in connection with EP 08794986.3, issued Dec. 15, 2010.

Non-final Office Action issued Dec. 10, 2009 in connection with U.S. Appl. No. 11/703,401.

Final Office Action issued Aug. 17, 2010 in connection with U.S. Appl. No. 11/703,401.

Non-final Office Action issued Oct. 26, 2010 in connection with U.S. Appl. No. 12/069,147.

Non-final Office Action issued Sep. 30, 2010 in connection with U.S. Appl. No. 12/460,407.

Eurasian Official Action issued Nov. 19, 2009 in connection with Eurasian Patent Application No. 200970737.

Notification of Transmittal of the International Search Report and the Written Opinion of the International Search Authority, or the Declaration, in connection with PCT/US09/04108, issued Sep. 15, 2009.

International Search Report in connection with PCT/US09/04108, issued Sep. 15, 2009.

Written Opinion in connection with PCT/US09/04108, issued Sep. 15, 2009.

Notification of Transmittal of the International Search Report and the Written Opinion of the International Search Authority, or the Declaration, in connection with PCT/US09/04378, issued Sep. 18, 2009.

International Search Report in connection with PCT/US09/04378, issued Sep. 18, 2009.

Written Opinion in connection with PCT/US09/04378, issued Sep. 18, 2009.

Notification of Transmittal of the International Search Report and the Written Opinion of the International Search Authority, or the Declaration, in connection with PCT/US09/04430, issued Jan. 12, 2010.

International Search Report in connection with PCT/US09/04430, issued Jan. 12, 2010.

Written Opinion in connection with PCT/US09/04430, issued Jan. 12, 2010.

Notification of Transmittal of International Preliminary Report on Patentablility in connection with PCT/US2008/011367, issued Apr. 15, 2010.

International Preliminary Report on Patentablility in connection with PCT/US2008/011367, issued Apr. 7, 2010.

Non-final Office Action issued Dec. 10, 2008 in connection with U.S. Appl. No. 11/703,401.

Notification Concerning Availability of the Publication of the International Application in connection with PCT/US2008/011367, issued Apr. 9, 2009.

Notification Concerning Transmittal of International Preliminary Report on Patentability in connection with PCT/US2008/001549, issued Aug. 11, 2009.

International Preliminary Report on Patentability in connection with PCT/US2008/001549, issued Aug. 11, 2009.

Supplemental European Search Report issued Oct. 4, 2011 in connection with European Patent Application No. 08836599.4, filed Mar. 29, 2010.

Communication pursuant to Rules 70(2) and 70a(2) EPC issued Oct. 21, 2011 in connection with European Patent Application No. 08836599.4, filed Mar. 29, 2010.

Bastian et al. (2004) "Nuclear retinoid receptors and the transcription of retinoid-target genes." Gene vol. 328, pp. 1-16.

Elaheta, A. et al. (2002), "Valproate and Valproate-Analogues: potent Tools to Fight Against Cancer," Current Medicinal Chemistry, vol. 9 pp. 1417-1344.

Blaskovich et al. "Recent discovery and development of protein tyrosine phosphatase inhibitors." Expert Opinion on Therapeutic Patents. 2002, vol. 12, No. 6, pp. 871-905.

Camphausen et al. (2005) "Influence of in vivo growth on human glioma cell line gene expression: Convergent profiles under orthotopic conditions." Proc. Natl. Acad. Sci. USA, vol. 102, No. 23, pp. 8287-8292.

Drewinko et al. (1967), "Combination chemotherapy in vitro with adriamycin. Observations of additive, antagonistic, and synergistic effects when used in two-drug combinations on cultured human lymphoma cells," Cancer Biochem. Biophys., vol. 1, pp. 187-195.

Erdodi et al. (1995), "Endothal thioanhydride inhibits proteins phosphatases-1 and -2A inhibition, and anticancer activity," Am. J. Physol. (Cell Physiol.) vol. 38, pp. C1176-C1184.

Flicker et al. "Tyrosine kinase signaling pathways control the expression of retinoic acid receptor-a in SK-BR-3 breast cancer cells." Cancer Lett. 1997, vol. 115, pp. 63-72.

Giannini, R. and Cavallini, A. (2005), "Expression analysis of a subset of coregulators and three nuclear receptors in colorectal carcinoma." Anticancer Research, vol. 36, No. 6B, pp. 4287-4292.

Gottlicher, M et al. (2001), "Valproic acid defines a novel class of HDAC inhibitors inducing differentiation of transformed cells," EMBO Journal, vol. 20, No. 24, pp. 6969-6978.

Hart, ME et al. (2004) "Modified norcantharidine: synthesis, protein phosphatases 1 and 2A inhibition, and anticancer activity," Bioorganic & Medicinal Chemistry Letters, vol. 14, pp. 1969-1973.

Havrilesky, LJ et al. (2001), "Relationship between expression of coactivators and corepressors of hormone receptors and resistance of ovarian cancers to growth regulation by steroid hormones," J. Soc. Gynecol. Investig., vol. 8, pp. 104-113.

Hermanson et al. (2002) "N-CoR controls differentiation of neural stem cells itno astrocytes," Nature, vol. 419 pp. 934-939.

Hughes et al. (1988) "Ciliary neurotrophic factor induces type-2 astrocyte differentiation in culture." Nature, vol. 335, pp. 70-73.

Kamitami et al. (2002) "Histone acetylation may suppress human glioma cell proliferation when p21WAF/Cip1 and gelsolin are induced." Neuro-Oncology, Apr. 2002, pp. 95-101.

Kawamura, N. et al. (1990) "Endothall Thioanhydride: Structural Aspects of Unusually High Mouse toxicity and Specific Binding Site in Liver." Chem. Res. Toxicol., vol. 3, pp. 318-324.

Kelly et al. (2005) "Drug insight: histone deacetylase inhibitors-development of the new targeted anticancer agent suberoylanilide hydroxamic acid." Nature Clinical Practice Oncology, vol. 2, No. 3, pp. 150-157.

Kim et al. (2004) "Susceptibility and radiosensitization of human glioblastoma cells to Trichostatin A, a histone deacetylase inhibitor." Int. J. Radiation Oncology Biol. Phys., vol. 59, No. 4, pp. 1174-1180.

Kovach, JS, et al. (1985) "Enhancement of the antiproliferative activity of human interferon by polyamine depletion." Cancer Treat. Rep., vol. 69, pp. 97-103.

Kurebayashi et al. "Expression levels of estrogen receptor-a, estrogen receptor-b, coactivators, and corepressors in breast cancer." Clin. Cancer Res., Feb. 2000, vol. 6, pp. 512-518.

Lavinsky et al. "Diverse signaling pathways modulate nuclear receptor recruitment of N-CoR and SMRT complexes." Proc. Natl. Acad. Sci. Mar. 1998, vol. 95, pp. 2920-2925.

Mardor et al. (2001) "Monitoring Response to Convection-enhanced Taxol delivery in brain tumor patients using diffusion-weighted magnetic resonance imaging" Cancer Res., 61, pp. 4971-4973.

Matsuzawa, M. et al. (1987), "Endothal and Cantharidin Analogues: Relation of Structure to Herbicidal Activity and Mammalian Toxicity." J. Agric. Food Chem., 35 (5), pp. 823-829.

Momparlet, RL. (1980), "In vitro systems for evaluation of combination chemotherapy," Pharmacol. Ther., vol. 8, pp. 21-35.

Myers, E. et al. (2005) "Associations and Interactions Between Ets-1 and Ets-2 and Coregulatory Proteins, SRC-1, AIB1 and NCoR in Breast Cancer," Clin. Cancer Res., vol. 11, pp. 2111-2122.

Park, DM. et al. (2007) N-CoR pathway targeting induces glioblastoma derived cancer stem cell differentiation, Cell Cycle, vol. 6, issue 4, pp. 467-470.

Peng, F. et al. (2002), "Induction of apoptosis by norcantharidin in human colorectal cell lines: involvement of the CD95 receptor/ligand," J. Cancer Res. Clin. Oncol., vol. 128, pp. 223-230.

Rutka et al. (1988), "Effect of retinoids on the proliferation, morphology and expression of glial fibrillary acidic protein of an anaplastic astrocytoma cell line," Int. J. Cancer, vol. 42, pp. 419-427.

Sakoff, JA. (2004) "Protein Phosphatase Inhibition: Structure Based Design, Towards New Therapeutic Agents," Current Pharmaceutical Design, vol. 10, pp. 1139-1159.

Sanderson, L et al. (2004), "Plasma Pharmacokinetics and Metabolism of the Histone Deacetylase Inhibitor Trichostatin A after Intraperitoneal Administration to Mice," Drug Metabolism and Disposition, vol. 32, No. 10, pp. 1132-1138.

Singh et al. (2003), "Identification of a cancer stem cell in human brain tumors," Cancer Research, vol. 63, pp. 5821-5828.

Singh et al. (2004), "Identification of human brain tumour initiating cells," Nature, vol. 432, pp. 396-401.

Stupp et al. (2005) "Radiotherapy plus Concomitant and Adjuvant Temozolomide for Glioblastoma." N. Engl. J. Med., vol. 352, pp. 987-996.

Toma et al. (2005) "Retinoids and human breast cancer: in vivo effects of an antagonist for RAR-α." Cancer Lett., 219, pp. 27-31.

Touma et al. (2005) "Retinoic acid and the histone deacetylase inhibitor Trichostatin A inhibit the proliferation of human renal cell carcinoma in a xenograph tumor model." Clin. Cancer Res., 11(9), pp. 3558-2566.

Uchida et al. (2000) "Direct isolation of human central nervous system stem cells." Proc. Natl. Acad. Sci. USA, vol. 97, pp. 14720-14725.

Valeriote, F. (1975), "Synergistic interaction of anticancer agents: A cellular perspective," Cancer Chemother. Rep., vol. 59, pp. 895-900.

Wang, GS (1983), "Hydrolysis and demethylation of cantharidin on the relief of its urinary irritation," Chin. Pharmac. Bull., col. 18, pp. 18-19, with English language summary.

Wang, GS (1989), "Medical uses of mylabris in ancient China and recent studies," J. Ethnopharmacol., vol. 26, pp. 147-162.

Wang, GS et al. (1986), "Results of clinical trials in 244 cases of primary hepatoma and with norcantharidin," Chinese. Pharm. Bull., vol. 21, pp. 90-93, with English translation of abstract.

Wang, GS et al. (1987), "Effect of norcantharidin on the number of white blood cells," Chinese Pharm. Bull., vol. 22, pp. 517-519, with English translation of abstract.

Waters, CE et al. (2004), "Analysis of co-factor 10 function in glucocorticoid-resistant small cell carcinoma line," J. Endocrinol., vol. 183, pp. 375-383.

Weinmann et al. (2005) "Histone deacetylase inhibitors: a survey of recent patents." Expert Opin. Ther. Patents, 15(12), pp. 1677-1690.

Yoshida, M et al. (1990), "Potent and Specific Inhibition of Mammalian Histone Deacetylase Both in vivo and in vitro by Trichostatin A." Journal of Biological Chem., vol. 265, No. 28, pp. 17174-17179.

Yung et al. "Treatment of recurrent malignant gliomas with high-dose 13-cis-retinoic acid" (1996) Clin. Cancer Res. vol. 2, pp. 1931-1935.

Ayaydin, F. et al. (2000) "Inhibition of serine/threonine specific protein phosphatases causes premature activation of cdc2MsF kinase at G2/M transition and early mitotic microtubule organization in alfalfa." The Plant Journal, 23:85-96.

Baskin, T. and Wilson, J. (1997) "Inhibitors of protein kinases and phosphatases alter root morphology and disorganize cortical microtubules." Plant Physiol. 113:493-502.

Essers, M. et al., (2001) "Synthesis of the first fluorinated cantharidin analogues." Tetrahedron Lett., 42, 5429-5433.

Honkanan, R.E. et al., (1993) "Cantharidin, another natural toxin that inhibits the activity of serinelthreonine protein phosphatases types 1 and 2A." FEBS Lett ., 330, 283-286.

Li, Y.M. et al. (1992) "Cantharidin-binding protein: Identification as protein phosphatase 2A." Proc. Natl. Acad. Sci. USA, 89, 11867-11870.

Ramezanian, M. et al., (1989) "A new super-electrophile: alpha-(phenylsulfonyl)maleic anhydride." J. Org. Chem., 54, 2852-2854.

Berthold, F., et al. (2005) "Myeloablative megatherapy with autologous stem-cell rescue versus oral maintenance chemotherapy as consolidation treatment in patients with high-risk neuroblastoma: a randomised controlled trial." Lancet Oncol., 6:649-658.

Chang, Q., et al. (2007) "All-trans-retinoic acid induces cell growth arrest in a human medulloblastoma cell line" J. Neurooncol, 84:263-267.

Gumireddy, K., et al. (2003) "All-trans-Retinoic Acid-induced Apoptosis in Human Medulloblastoma: Activation of Caspase-3/Poly(ADPribose) Polymerase 1 Pathway." Clinical Cancer Research, 9:4052-4059.

Joshi, S., et al. (2006) "Retinoic acid receptors and tissue-transglutaminase mediate short-term effect of retinoic acid on migration and invasion of neuroblastoma SH-SY5Y cells." Oncogene, 25:240-274.

Li, X-N., et al. (2005) "Valproic acid induces growth arrest, apoptosis, and senescence in medulloblastomas by increasing histone hyperacetylation and regulating expression of p21Cip1, CDK4, and CMYC." Mol Cancer Ther., 4(12):1912-1922.

Matthay, KK., et al. (1999) "Treatment of High-Risk Neuroblastoma With Intensive Chemotherapy, Radiotherapy, Autologous Bone Marrow Transplantation, and 13-Cis-Retinoic Acid." N. Engl. J Med. ,341:1165-1173.

Abel et al. (2008) "Epigenetic targets of HDAC inhibition in neurodegenerative and psychiatric disorders", Curr. Opin. Pharmacol., 8, pp. 57-64.

Acharya et al. (2005) "Rational development of histone deacetylase inhibitors as anticancer agents: a review", mol. Pharmacol., 68, pp. 917-932.

Adcock, I. (2007) "HDAC Inhibitors as anti-inflammatory agents" Br. J. Pharm., vol. 150, pp. 829-831.

Albert, M. S. (2007) "Changing the Trajectory of Cognitive Decline?" N. Engl. J. Med., 357(5), pp. 502-503.

Beglopoulis et al. (2006) "Regulation of CRE-dependent transcription by presenilins: prospects for therapy of Alzheimer's disease" Trends Pharmacol. Sci., 27(1), pp. 33-40.

Burke, R. E. (2007) "Inhibition of mitogen-activated protein kinase and stimulation of Akt kinase signaling pathways: Two approaches with therapeutic potential in the treatment of neurodegenerative disease" Pharmacology and Therapeutics, 114, pp. 261-277.

David et al. (1998) "Histone deacetylase associated with mSin3A mediates repression by the acute promyelocytic leukemia-associated PLZF protein" Oncogene, 16, 2549-2556.

Finnin et al (1999) "Structures of a histone deacetylase homologue bound to the TSA and SAHA inhibitors" Nature, 401, pp. 188-193.

Fischer et al. (2007) "Recovery of learning and memory is associated with chromatin remodeling" Nature, vol. 447, pp. 178-183.

Furumai et al. (2001) "Potent histone deacetylase inhibitors built from trichostatin A and cyclic tetrapeptide antibiotics including trapoxin" Proc. Natl. Acad. Sci. USA, 98(1), pp. 87-92.

Hildmann et al. (2007) "Histone deacetylases—an important class of cellular regulators with a variety of functions", Appl. Microbiol. Biotechnol., vol. 75, pp. 487-497.

Hoshikawa et al, (1994) "Trichostatin A Induces Morphological Changes and Gelsolin Expression by Inhibiting Histone Deacetylase in Human Carcinoma Cell Lines" Exp. Cell Res., 214(1), pp. 189-197.

Huang, L. (2006) "Targeting histone deacetylases for the treatment of cancer and inflammatory diseases", J. Cellular Phys., vol. 209, pp. 611-616.

Kitamura et al. (2000) "Histone deacetylase inhibitor but not arsenic trioxide differentiates acute promyelocytic leukaemia cells with t(11,17) in combination with all-trans retinoic acid" Brit. J. Haematol., 108(4), pp. 696-702.

Korzus et al. (2004), "CBP Histone Acetyltransterae Activity Is a Critical, Component of Memory Consolidation" Neuron, vol. 42, pp. 961-972.

Kozikowski et al. (2007) "Functional differences in epigenetic modulators-suberiority of mercaptoacetamide-based histone deacetylase inhibitors relative to hydroxamates in cortical neuron neuroprotection studies" J. Med. Chem., 50, pp. 3054-3061.

Kwon et al, "Depudecin induces morphological reversion of transformed fibroblasts via the inhibition of histone deacetylase" Proc. Natl., Acad. Sci . USA, 95(7), pp. 3356-3361.

Langley et al, (2008) 'Pulse inhibition of histone deacetylases induces complete resistance to oxidative death in cortical neurons without toxicity and reveals a role for cytoplasmic p21wafl/cipl in cell cycle-independent neuroprotection J. Neurosci., 28 (1), pp. 163-176.

Levenson at al. (2004) "Regulation of Histone Acetylation during memory formation in the hippocampus" J. Biol. Chem. , 29(39), pp. 40545-40559.

Lin at al (1998) "Role of the histone deacetylase complex in acute promyelocytic leukaemia" Nature, 391(6669), pp. 811-814.

Mangan et al. (2007) "Turning back the clock on neurodegeneration" Cell, vol. 129, pp. 851-853.

Mielnicki et al. (1999) "Epigenetic regulation of gelsolin expression in human breast cancer cells", Exp. Cell Res., 249(1), pp. 161-176.

Price et al. 2007) "Histone deacetylase inhibitors: an analysis of recent patenting activity" Expert Opin. Ther. Patents, 17(7), pp. 745-765.

Riester et al. (2007) "Histone deacetylase inhibitors-turning epigenic mechanisms of gene regulation into tools of therapeutic intervention in malignant and other diseases" Appl. Microbiol. Biotechnol., vol. 75, pp. 499-514.

Smith, W. L. et al, (2002) "Histone deacetlylase inhibitors enhance Candida albicans sensitivity to azoles and related antifungals: correlation with reduction in CDR and ERG upregulation", Antimicrob. Agents Chemother., 46(11), pp. 3532-3539.

Song et al. (2002) "Synthesis and Biological Properties of Amino Acid Amide Ligand-Based Pyridinioalkanoyl Thioesters as Anti-HIV Agents" Bioorganic and Medicinal (Chem., 10 (5), pp. 1263-1273.

Sweatt, J. D. (2007) "Behavioural neuroscience: Down memory lane" Nature; 447, pp. 151-152.

Warrell, Jr. et al. (1998) "Therapeutic Targeting of Transcription in Promyelocytic Leukemia by Use of an Inhibitor of Histone Deacetylase" J. Natl. Cancer Inst., 90, pp. 1621-1625.

Yoshida at el. (1999) "Trichostatin and Leptomycin Inhibition of Histone Deacetylatlon and Signal-Dependent Nuclear Export" Ann. N.Y. Acad. Sci., 886 pp. 23-35.

Science IP Search Report dated Sep. 20, 2007.

Non-final Office Action issued Mar. 30, 2009 in connection with U.S. Appl. No. 11/703,401.

McCluskey et al. (1996) "Inhibition of Protein Phosphatase 2A by Cantharidin Analogues" Bioorg. Med. Chem. Lett., 6(9), pp. 1025-1028.

McCluskey at al. (2000) "Anhydride Modified Cantharidin Analogues: Synthesis, inhibition of Protein Phosphatases 1 and 2A and Anticancer Activity" Bioorg. Med, Chem, Lett., 10, pp. 1687-1690.

McCluskey et al. (2000) "Anhydride modified cantharidin analogues. Is ring opening important in the inhibition of protein phosphatase 2A?" Eur, J. Med. Chem., 35, pp. 957-964.

Sakoff et al. (2002) "Anticancer activity and protein phosphatase 1 and 2A inhibition of a new generation of cantharidin analogues" Invest. New Drugs, 20, pp. 1-11.

Hill et al. (2007) "Heterocyclic substituted cantharidin and norcantharidin analogues—synthesis, protein phosphatase (1 and 2A) inhibition, and anti-cancer activity" Bioorg. Med. Chem. Lett., 17, pp. 3392-3397.

Levesque. Reduction of L-DOPA-induded dyskinesias by retinoid agonists: a new way to improve Parkinson's disease treatment. The Parkinson Aliance, 2004 Pilot Study Grants, abstract only.

Paez et al. "PI3K/PTEN/AKT pathway." Signal Transduction in Cancer, Kluwer Academic Publishers, 2006, vol. 115, pp. 1-28.

Sahin at al. "Retinoic Acid Isomers Protect Hippocampal Neurons From Amyloid-beta Induced Neurodegeneration." Neurotoxicity Res., 2005, vol. 7(3), pp. 243-250.

Abbas, "Synthesis of Mixed-dono Azaoxathia Macrocyclic Tetraamides, Acyclic Polyether di/and Tetraamide and Their C-Pivot Lariat Derivatives", J. Het. Chem., vol. 44, No. 3, 2007, pp. 651-661.

Isfort et al., "Helical Complexes Containing Diamide-Bridged Benzene-o-dithiolate/Catecholato Ligands", Chemistry-A European Journal, vol. 13, No. 8, 2006, 2344-2357.

Kreickmann at al. "Metallosupramolecular Chemistry with Bis (benzene-o-dithiolato) Ligands", J. Am. Chem. Soc., vol. 128, No. 36, 2006, p. 11808-11819.

Winstanley et al., "Ortho-Substituted Catechol Derivatives: The Effect of Intramolecular Hydrogen-Bonding Pathways on Chloride Anion Recognition", J. Org. Chem., vol. 72, No. 8, 2007, pp. 2803-2815.

* cited by examiner

FIGURE 8A MDA-MB-231-Breast
A.
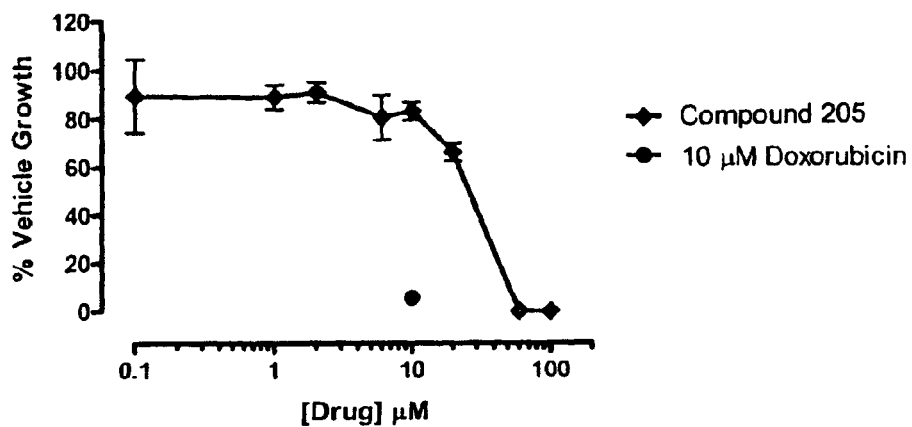
B.
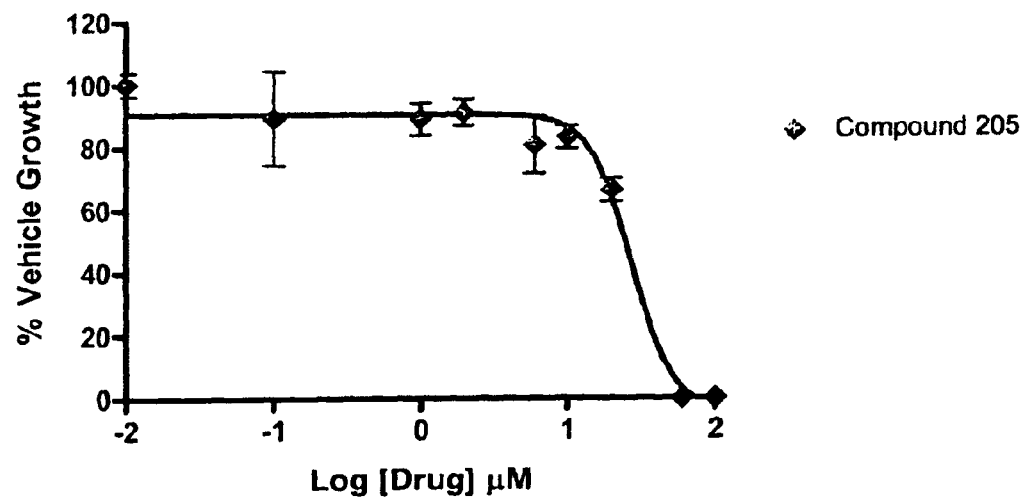

A.
Figure 8B HT-29-Colon
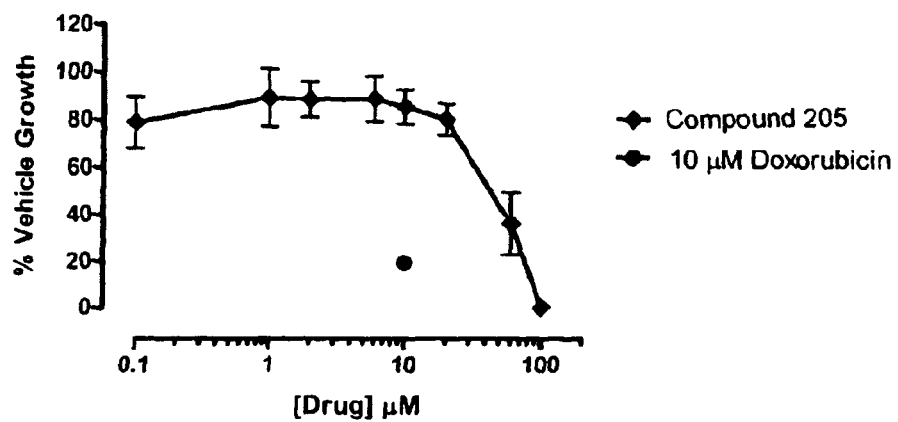
B.
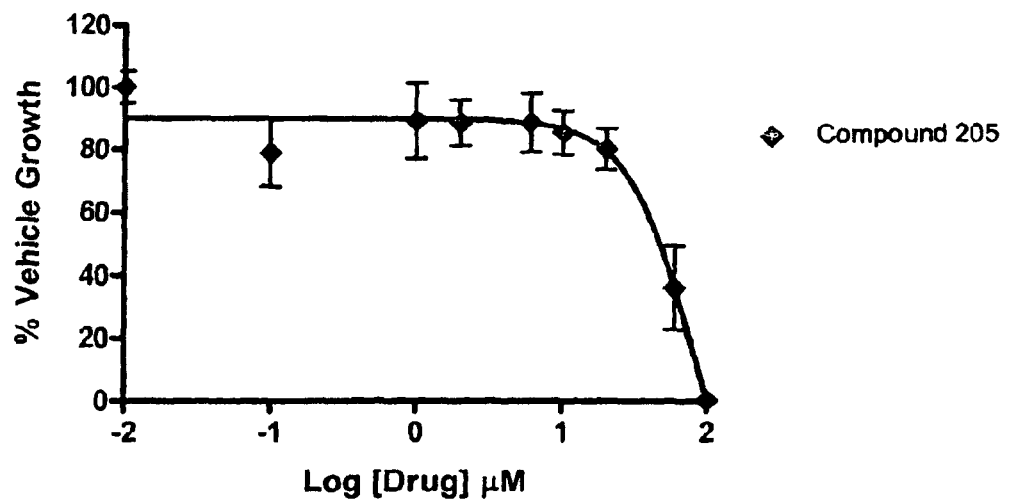

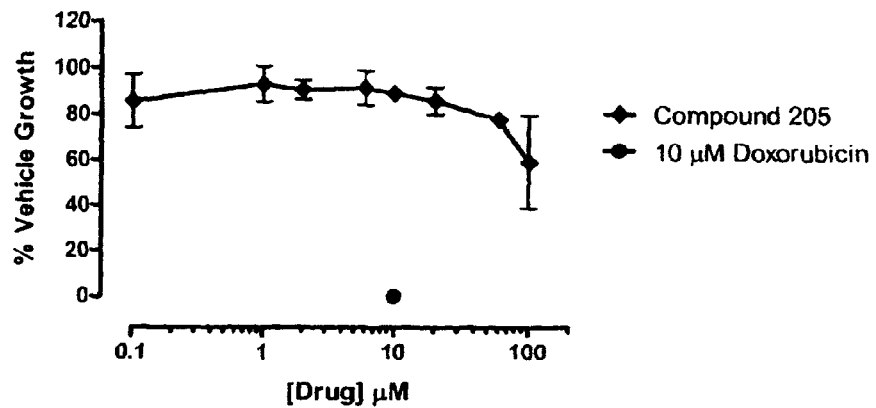
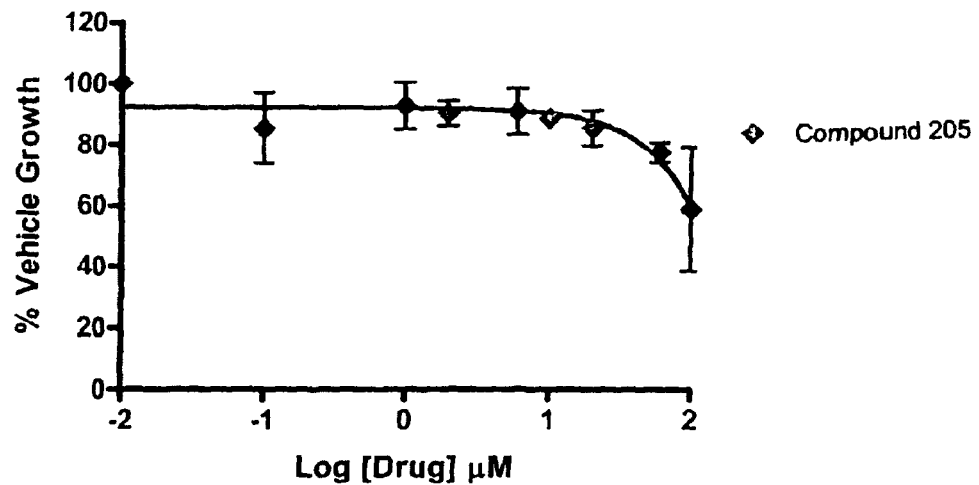
Figure 8C: NCI-H460-Lung, Large Cell

Figure 8D NCI-H522-Lung, Adenocarcinoma
A.
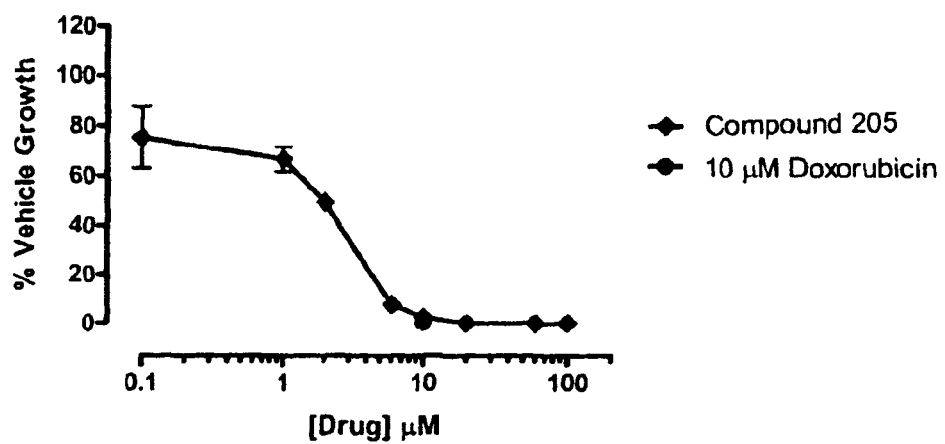
B.
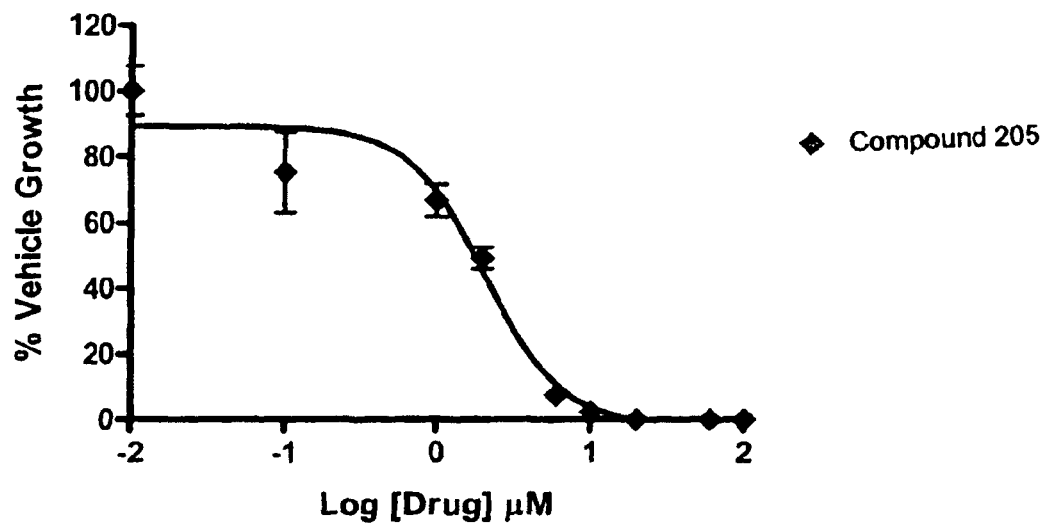

Figure 8E NCI-H69-Lung, Small Cell
A.
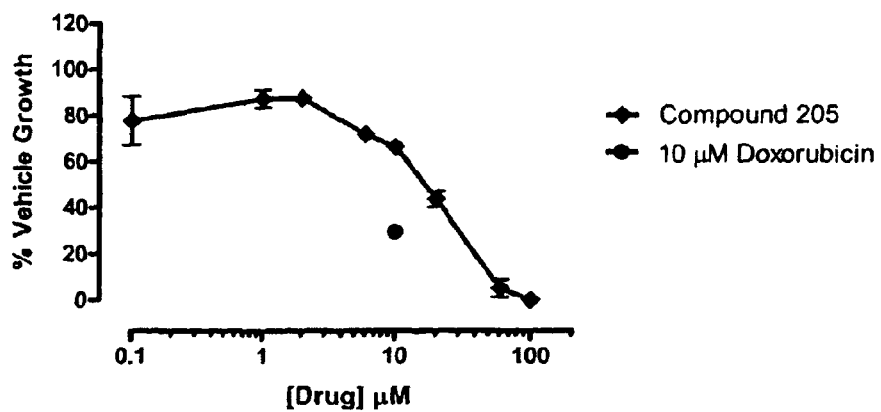
B.
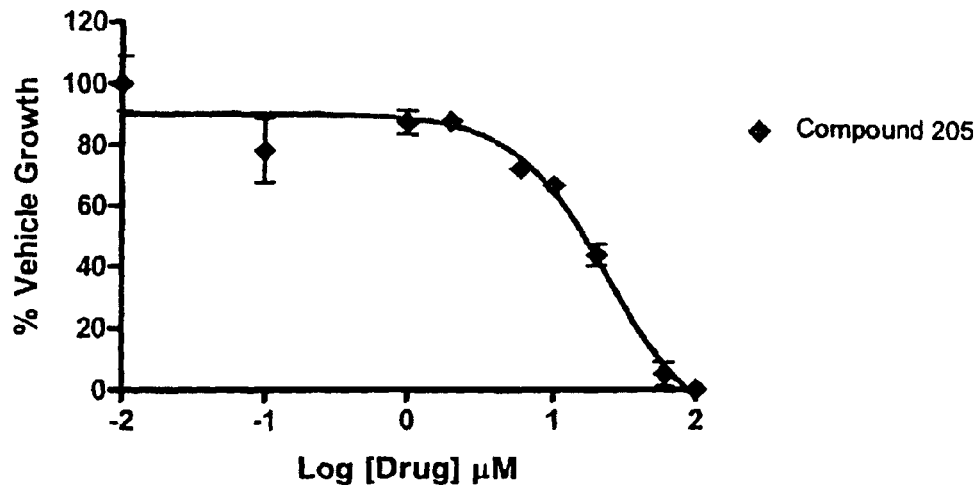

Figure 8F GXF-209-Stomach
A.
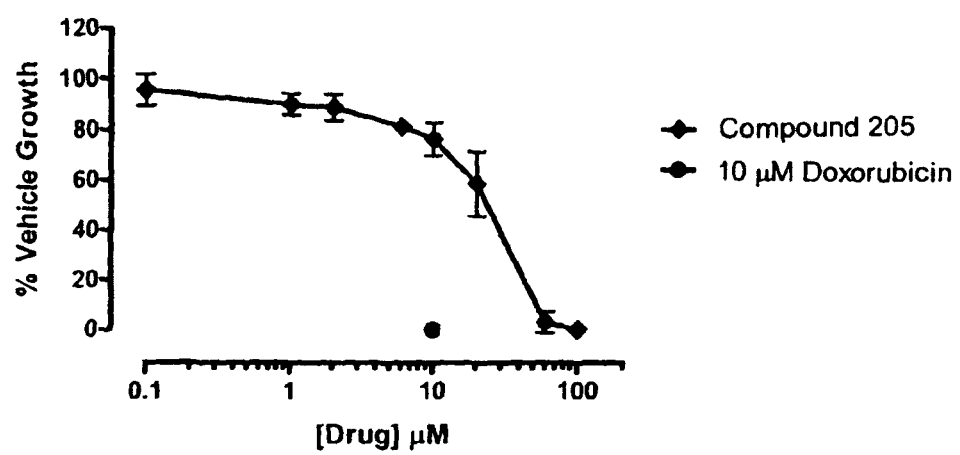
B.
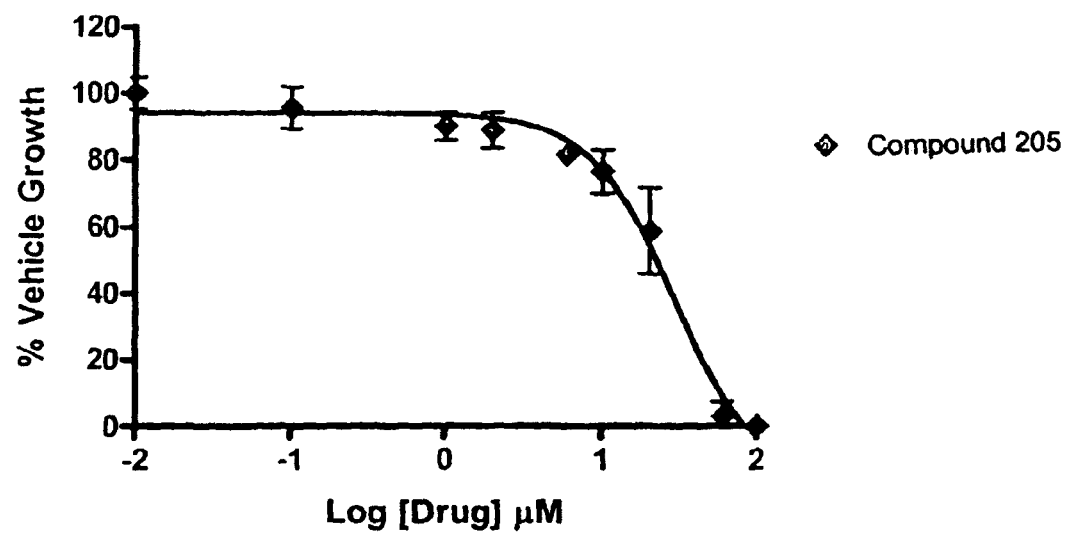

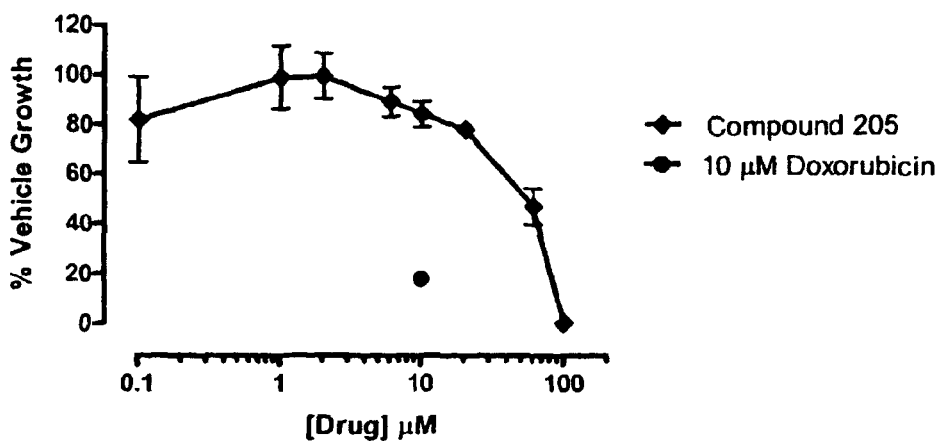
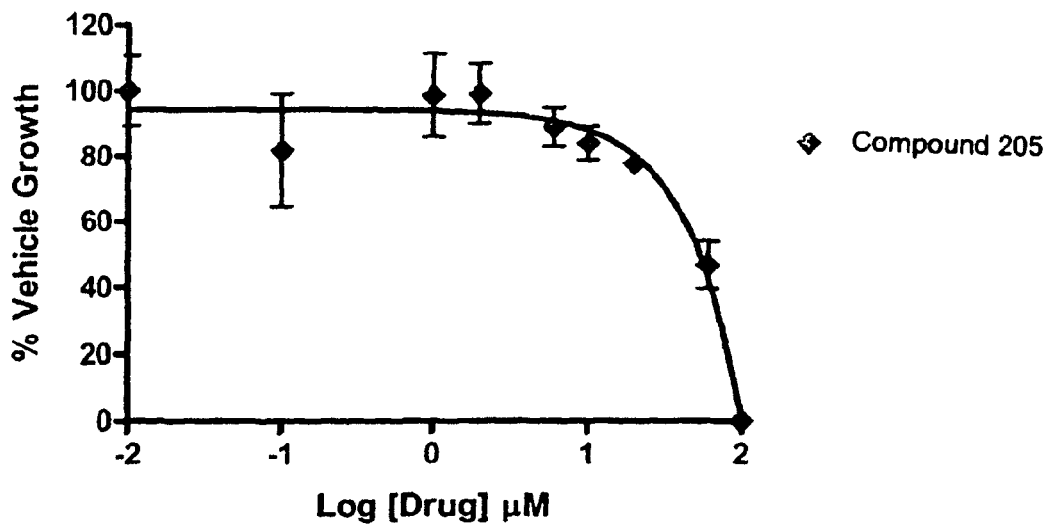
Figure 8G HepG2-Hepatoma

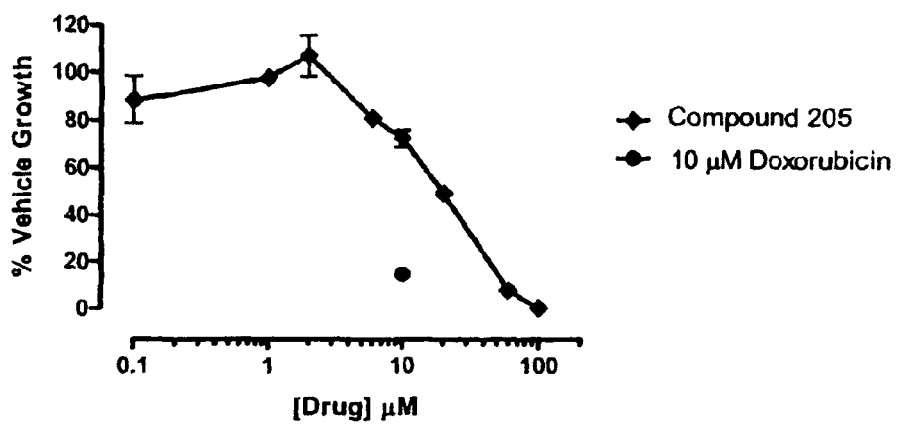
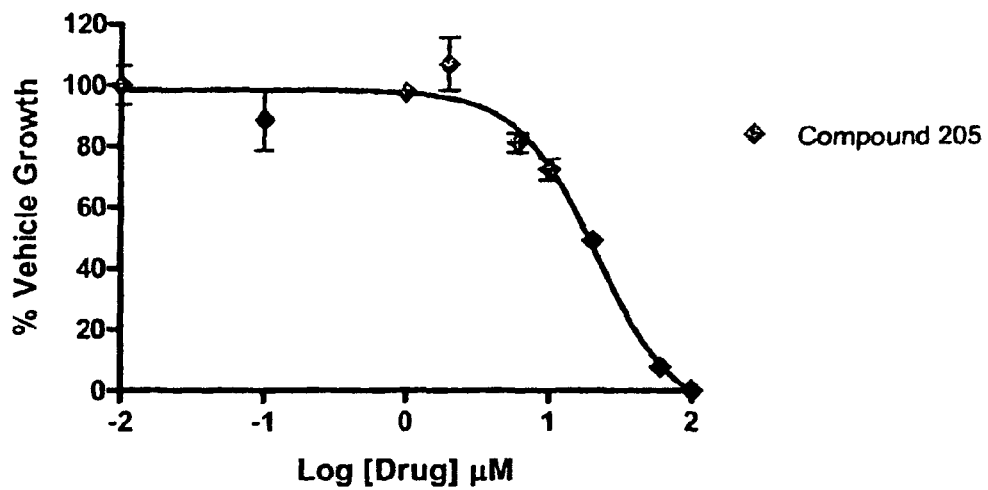
Figure 8H OVCAR-3-Ovarian

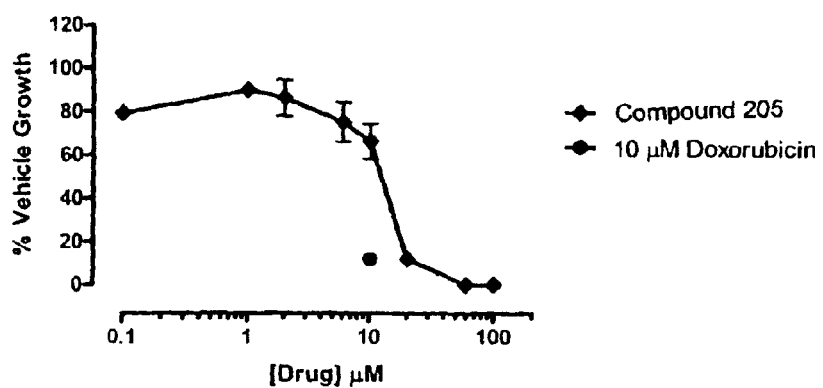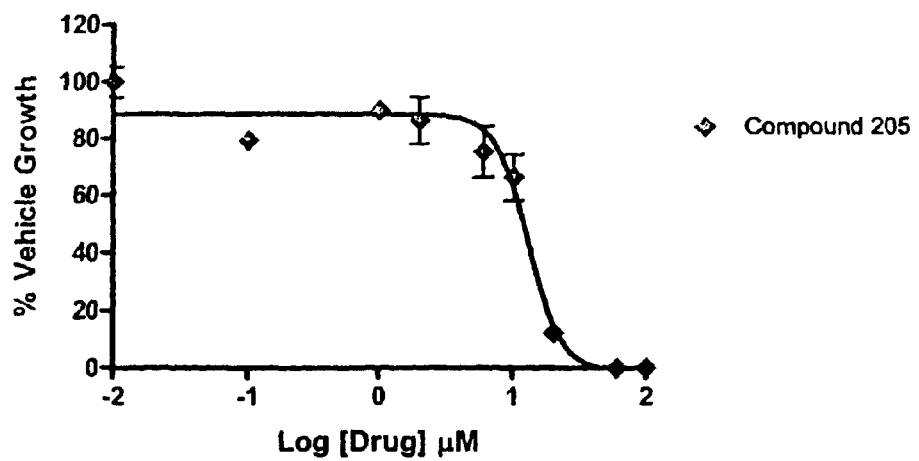
Figure 8I PANC-1-Pancreas

Figure 8J DU-145-Prostate
A.
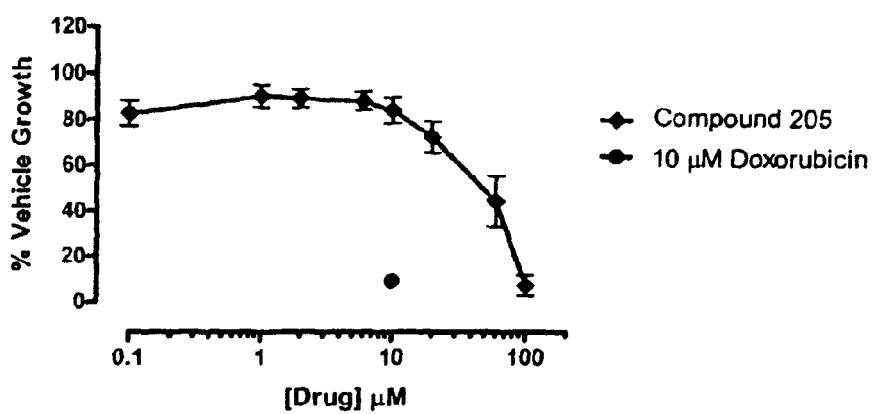
B.
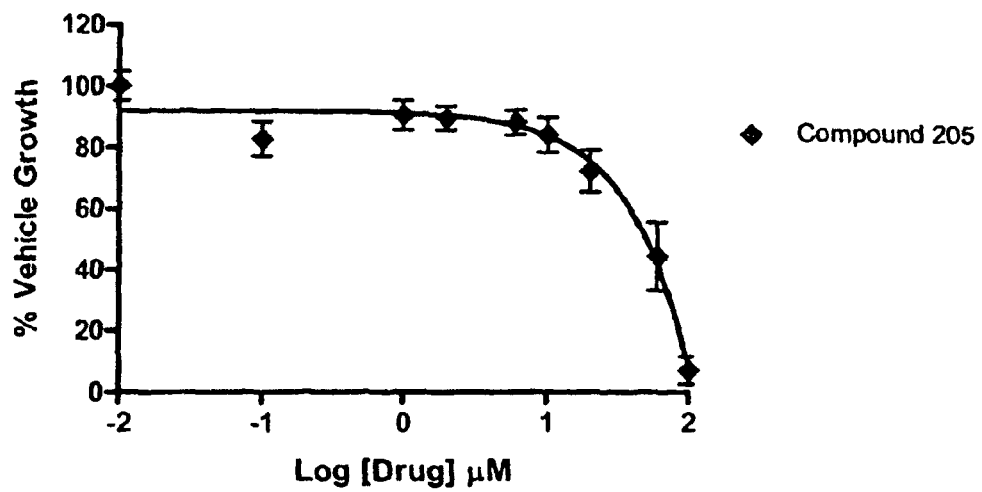

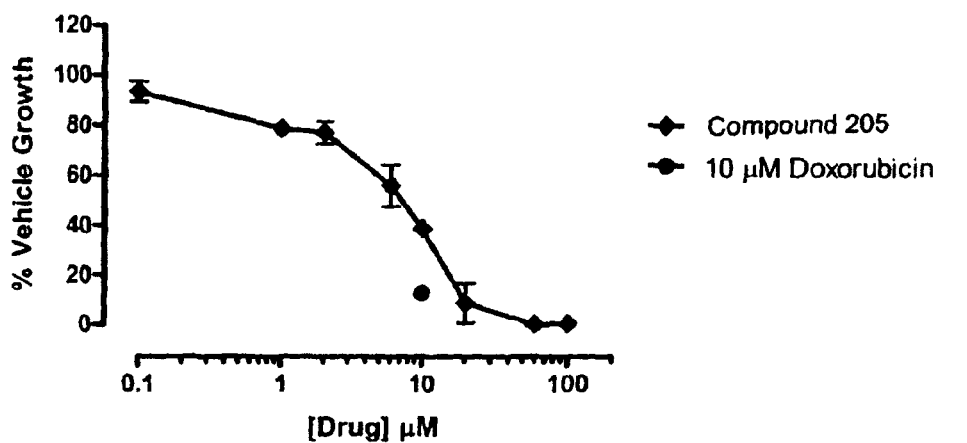
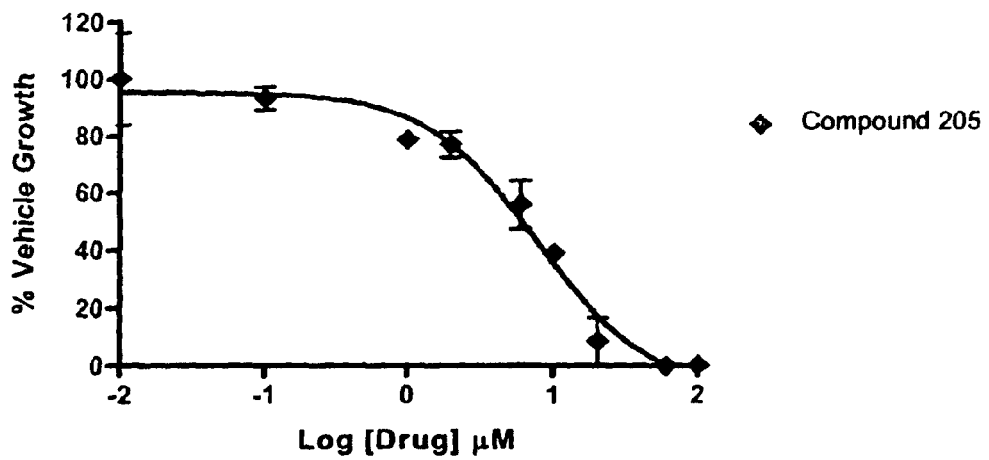

Figure 8L HL-60-Leukemia, Promyelocytic
A.
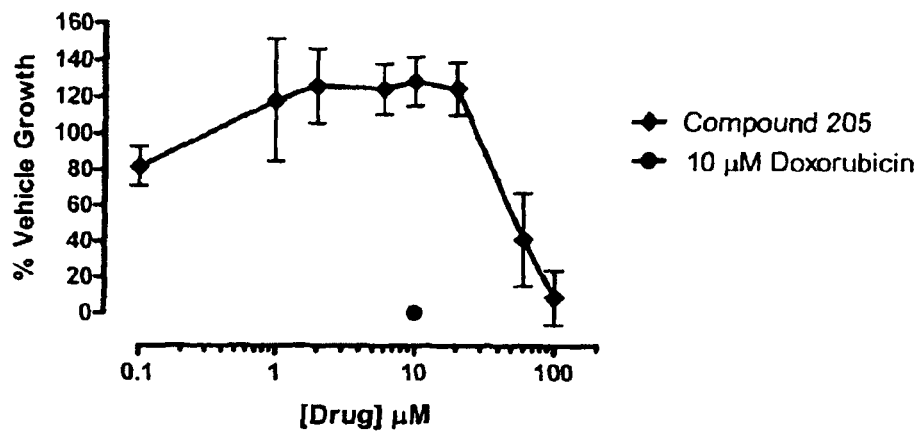
B.
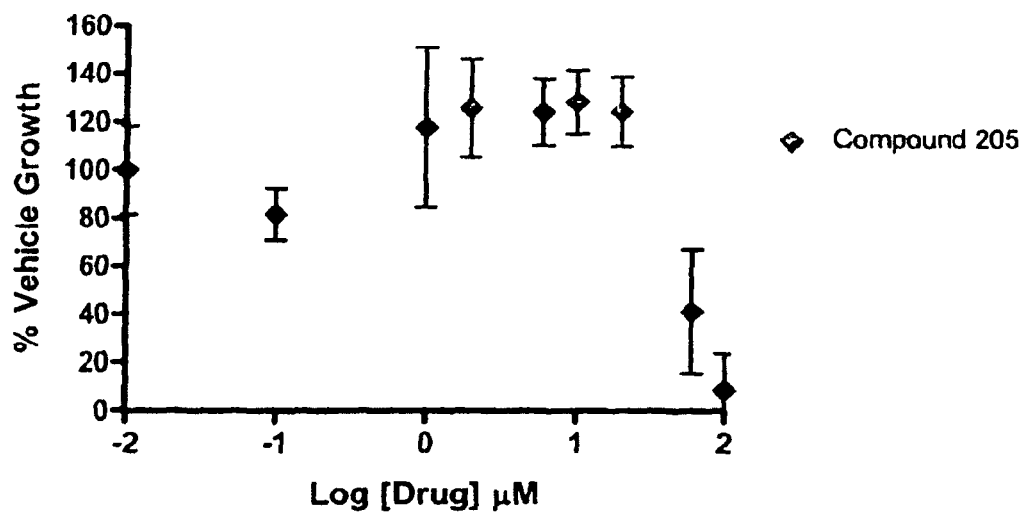

Figure 8M K-562- Leukemia, Chronic Myelocytic
A.
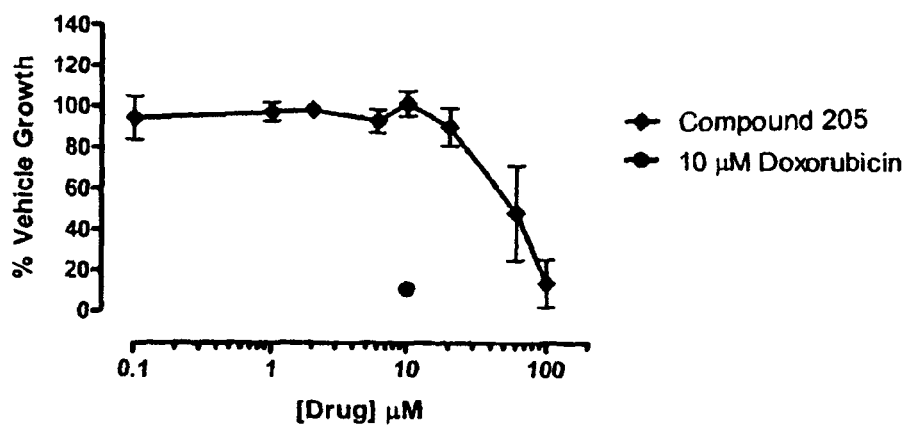
B.
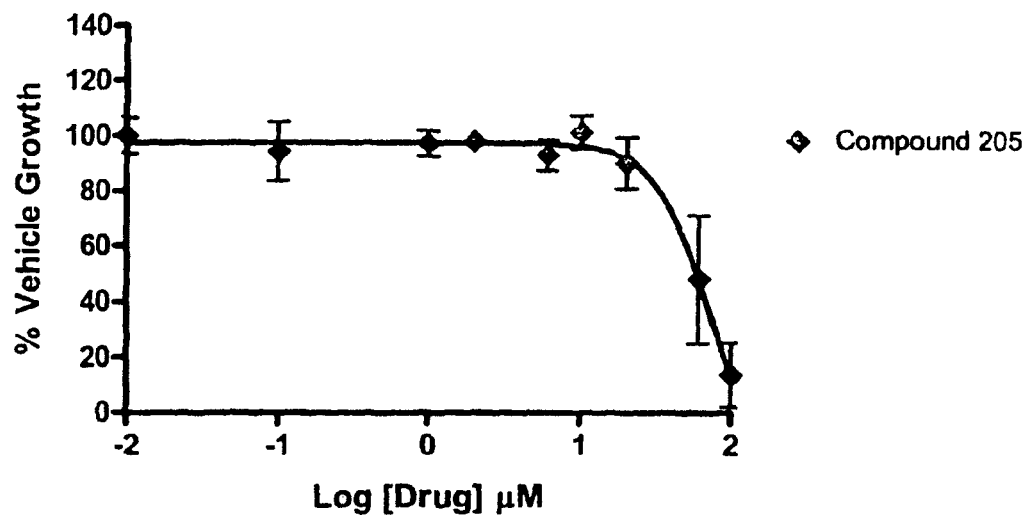

Figure 8N MOLT-4-Leukemia, Acute Lymphocytic
A.
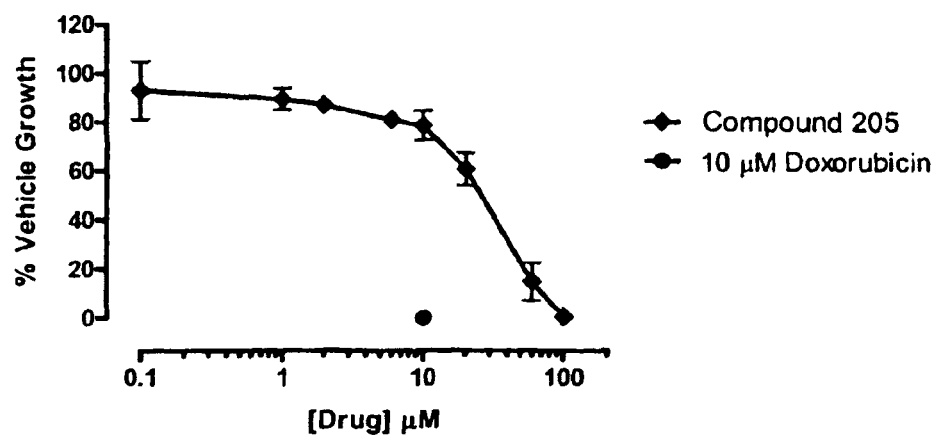
B.
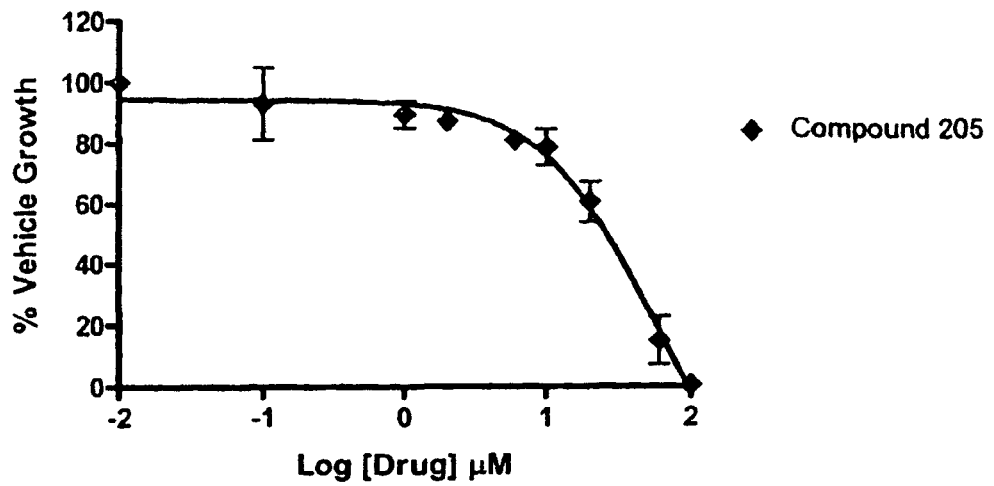

HDAC INHIBITORS

The present application is a divisional of U.S. Ser. No. 12/286,769, filed Oct. 1, 2008, now U.S. Pat. No. 8,143,445, which claims the benefit of U.S. Provisional Application Nos. 61/063,965, filed Feb. 6, 2008; 61/008,673, filed Dec. 21, 2007; and 60/997,338, filed Oct. 1, 2007, the contents of each of which are hereby incorporated by reference.

Throughout this application, certain publications are referenced. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Histone deacetylases (hereinafter also referred as HDACs) are known to play an essential role in the transcriptional machinery for regulating gene expression, induce histone hyperacetylation and to affect the gene expression. Therefore, it is a target of a therapeutic or prophylactic agent for diseases caused by abnormal gene expression such as inflammatory disorders, diabetes, diabetic complications, homozygous thalassemia, fibrosis, cirrhosis, acute promyelocytic leukemia (APL), organ transplant rejections, autoimmune diseases, protozoal infections, tumors, etc., to inhibit HDAC proteins.

Acetylation and deacetylation of histones are carried out by histone acetyl transferases (HAT) and histone deacetylases (HDACs). The state of acetylation of histones is an important determinant of gene transcription. Deacetylation is generally associated with reduced transcription of genes whereas increased acetylation of histones as induced by the action of HDAC inhibitors results in greater transcription of genes. Thus, HDAC inhibitors affect multiple processes in the cell which are likely to depend upon the dynamic state of the cell with respect to its capabilities of replication and differentiation.

The study of inhibitors of histone deacetylases indicates that these enzymes play an important role in cell proliferation and differentiation. The inhibitor Trichostatin A (TSA) (Yoshida et al. (1990) "Structural specificity for biological activity of trichostatin A, a specific inhibitor of mammalian cell cycling with potent differentiation-inducing activity in Friend leukemia cells" J. Antibiot. 43(9):1101-6), causes cell cycle arrest at both G1 and G2 phases (Yoshida and Beppu, (1988) "Reversible arrest of proliferation of rat 3Y1 fibroblasts in both the G1 and G2 phases by trichostatin A" Exp Cell Res. 177(1):122-31), reverts the transformed phenotype of different cell lines, and induces differentiation of Friend leukemia cells and others. TSA and suberoylanilide hydroxamic acid (SAHA) have been reported to inhibit cell growth, induce terminal differentiation, and prevent the formation of tumours in mice (Finnin et al., (1999) "Structures of a histone deacetylase homologue bound to the TSA and SAHA inhibitors" Nature 401, 188-193).

Cell cycle arrest by TSA correlates with an increased expression of gelsolin (Hoshikawa et al., (1994) "Trichostatin A induces morphological changes and gelsolin expression by inhibiting histone deacetylase in human carcinoma cell lines" Exp Cell Res. 214(1):189-97), an actin regulatory protein that is down regulated in malignant breast cancer (Mielnicki et al., (1999) "Epigenetic Regulation of Gelsolin Expression in Human Breast Cancer Cells" Experimental Cell Research, 249(1) pp. 161-176). Similar effects on cell cycle and differentiation have been observed with a number of deacetylase inhibitors (Kim et al., (1999) "Selective Induction of Cyclin-Dependent Kinase Inhibitors and Their Roles in Cell Cycle Arrest Caused by Trichostatin A, an Inhibitor of Histone Deacetylase" Ann. N.Y. Acad. Sci. 886: 200-203).

Trichostatin A has also been reported to be useful in the treatment of fibrosis, e.g., liver fibrosis and liver cirrhosis. See, e.g., Geerts et al., (1998) "Hepatic Stellate Cells and Liver Retinoid Content in Alcoholic Liver Disease in Humans" Clinical and Experimental Research 22 (2), 494-500.

Recently, certain compounds that induce differentiation have been reported to inhibit histone deacetylases. Several experimental antitumour compounds, such as trichostatin A (TSA), trapoxin, suberoylanilide hydroxamic acid (SAHA), and phenylbutyrate have been reported to act, at least in part, by inhibiting histone deacetylase (see, e.g., Yoshida et al. (1990) "Structural specificity for biological activity of trichostatin A, a specific inhibitor of mammalian cell cycle with potent differentiation-inducing activity in Friend leukemia cells" J. Antibiot. 43(9):1101-6; Richon et al., (1998) "A class of hybrid polar inducers of transformed cell differentiation inhibits histone deacetylases" PNAS 95(6) 3003-3007; and Kijima et al., (1993) "Trapoxin, an antitumor cyclic tetrapeptide, is an irreversible inhibitor of mammalian histone deacetylase" J. Biol. Chem., 268(30) 22429-22435). Additionally, diallyl sulfide and related molecules (see, e.g., Lea et al., (1999) "Increased acetylation of histones induced by diallyl disulfide and structurally related molecules" Int J Oncol. 15(2):347-52), oxamflatin (see, e.g., Kim et al., (1999) "Selective Induction of Cyclin-Dependent Kinase Inhibitors and Their Roles in Cell Cycle Arrest Caused by Trichostatin A, an Inhibitor of Histone Deacetylase" Ann. N.Y. Acad. Sci. 886: 200-203), MS-27 275, a synthetic benzamide derivative (see, e.g., Saito et al., (1999) "A synthetic inhibitor of histone deacetylase, MS-27-275, with marked in vivo antitumor activity against human tumors" PNAS 96(8) 4592-4597; Suzuki et al., (1999) "Synthesis and Histone Deacetylase Inhibitory Activity of New Benzamide Derivatives" *J. Med. Chem.*, 42 (15), 3001-3003; note that MS-27 275 was later re-named as MS-275); butyrate derivatives (see, e.g., Lea and Tulsyan, (1995) "Discordant effects of butyrate analogues on erythroleukemia cell proliferation, differentiation and histone deacetylase" Anticancer Res. 15(3):879-83), FR901228 (see, e.g., Nokajima et al., 1998), depudecin (see, e.g., Kwon et al., (1998) "Depudecin induces morphological reversion of transformed fibroblasts via the inhibition of histone deacetylase" PNAS 95(7) 3356-3361), and m-carboxycinnamic acid bishydroxamide (see, e.g., Richon et al., 1998) have been reported to inhibit histone deacetylases. In vitro, some of these compounds are reported to inhibit the growth of fibroblast cells by causing cell cycle arrest in the G1 and G2 phases, and can lead to the terminal differentiation and loss of transforming potential of a variety of transformed cell lines (see, e.g., Richon et al, 1996; Kim et al., 1999; Yoshida et al., 1995; Yoshida & Beppu, 1988 (full cites provided earlier)). In vivo, phenylbutyrate is reported to be effective in the treatment of acute promyelocytic leukemia in conjunction with retinoic acid (see, e.g., Warrell et al., (1998) "Therapeutic Targeting of Transcription in Acute Promyelocytic Leukemia by Use of an Inhibitor of Histone Deacetylase" Journal of the National Cancer Institute, Vol. 90, No. 21, 1621-1625). SAHA is reported to be effective in preventing the formation of mammary tumours in rats, and lung tumors in mice (see, e.g., Desai et al., 1999).

The clear involvement of HDACs in the control of cell proliferation and differentiation suggest that aberrant HDAC activity may play a role in cancer. The most direct demonstration that deacetylases contribute to cancer development comes from the analysis of different acute promyelocytic leukaemias (APL). In most APL patients, a translocation of chromosomes 15 and 17 (t(15;17)) results in the expression of a fusion protein containing the N-terminal portion of PML gene product linked to most of RARα (retinoic acid receptor). In some cases, a different translocation (t(11;17)) causes the fusion between the zinc finger protein PLZF and RARα. In the absence of ligand, the wild type RARα represses target genes by tethering HDAC repressor complexes to the promoter DNA. During normal hematopoiesis, retinoic acid (RA) binds RARα and displaces the repressor complex, allowing expression of genes implicated in myeloid differentiation. The RARα fusion proteins occurring in APL patients are no longer responsive to physiological levels of RA and they interfere with the expression of the RA-inducible genes that promote myeloid differentiation. This results in a clonal expansion of promyelocytic cells and development of leukemia. In vitro experiments have shown that TSA is capable of restoring RA-responsiveness to the fusion RARα proteins and of allowing myeloid differentiation. These results establish a link between HDACs and oncogenesis and suggest that HDACs are potential targets for pharmaceutical intervention in APL patients. (See, for example, Kitamura et al., (2000) "Histone deacetylase inhibitor but not arsenic trioxide differentiates acute promyelocytic leukaemia cells with t(11;17) in combination with all-trans retinoic acid" Brit. J. Hemat. 108 (4) 696-702,; David et al., (1998) "Histone deacetylase associated with mSin3A mediates repression by the acute promyelocytic leukemia-associated PLZF protein" Oncogene (1998) 16, 2549-2556; Lin et al., (1998) "Role of the histone deacetylase complex in acute promyelocytic leukaemia" Nature 391(6669):811-4).

Furthermore, different lines of evidence suggest that HDACs may be important therapeutic targets in other types of cancer. Cell lines derived from many different cancers (prostate, colorectal, breast, neuronal, hepatic) are induced to differentiate by HDAC inhibitors (Yoshida and Horinouchi, (1999) "Trichostatin and Leptomycin: Inhibition of Histone Deacetylation and Signal-Dependent Nuclear Export" *Annals of the New York Academy of Sciences* 886:23-35). A number of HDAC inhibitors have been studied in animal models of cancer. They reduce tumor growth and prolong the lifespan of mice bearing different types of transplanted tumours, including melanoma, leukemia, colon, lung and gastric carcinomas, etc. (Ueda et al., (1994) "Serum levels of cytokines in patients with colorectal cancer: Possible involvement of interleukin-6 and interleukin-8 in hematogenous metastasis" 29(4); Kim et al., 1999).

Several of the known HDAC inhibitors have been found to be protective in different cellular and animal models of acute and chronic neurodegenerative injury and disease, for example, ischemic stroke, multiple sclerosis, and polyglutamine-expansion diseases, such as Huntington's disease and spinal and bulbar muscular atrophy (SBMA) (Kozikowski et al, J. Med. Chem. (2007), 50, 3054-3061). Furthermore, recent findings suggest that HDAC inhibitors can ameliorate deficits in synaptic plasticity, cognition, and stress-related behaviors in a wide range of neurologic and psychiatric disorders including Huntington's disease, Parkinson's disease, anxiety and mood disorders, Rubinstein-Taybi syndrome, and Rett syndrome (Abel, T. and Zukin, R. S., *Current Opinion in Pharmacology* (2008) 8:57-64). Beglopoulos and Shen (Beglopoulos, V. and Shen, J., *TRENDS in Pharmacological Sciences* (2006) 27:33-40) found that inhibitors of phosphodiesterase 4 and histone deacetylases reduce memory deficits and neurodegeneration in animal models of AD affecting cAMP response element (CRE) genes. Recently, Fischer et al (Fischer, A. et al., *Nature* (2007) 447:178-182) reported improved learning behavior and access to long-term memories after significant neuronal loss and brain atrophy can be reestablished in a mouse model by environmental enrichment and by treatment with inhibitors of histone deacetylases (see reviews and commentaries by Sweat, J. D. et al., *Nature* (2007) 447:151-152; Mangan, K. P. and Levenson, J. M., *Cell* (2007) 129:851-853; Albert, M. S., *New Engl. J. Med.* (2007) 357(5):502-503; and Abel, T. and Zukin, R. S., *Current Opinion in Pharmacology* (2008) 8:57-64). There appears to be a poorly understood component of neurodegenerative diseases related to excessive histone deacetylase activity, or at least a condition of reduced acetylation of certain histones that is corrected by increased acetylation resulting in improved learning and memory. In this respect, inhibition of certain histone deacetylases with the compounds described herein may potentially prove to be advantageous in the treatment of neurodegenerative diseases such as AD.

It has been estimated that neurodegenerative diseases presently affect 20 million individuals worldwide. The cost for medical care of patients with AD, for example, was $91 billion in 2005 and is predicted to increase to $160 billion by 2010 (Burke, R. E., *Pharmacology and Therapeutics* (2007) 114:262-277). Despite considerable research on the etiology and pharmacologic treatment of these diseases, no therapy is known to delay their progression (Schapira, A. H. V. and Olanow, C. W., *JAMA* (2004) 291:358-364; Burke, R. E., *Pharmacology and Therapeutics* (2007) 114:262-277). Alzheimer's disease (AD) and other neurodegenerative diseases are called tauopathies because they are characterized by the accumulation of aggregates of the tau protein in neurons. Tau proteins promote the assembly and stabilization of microtubular structures in neurons. Neurodegenerative diseases such as AD are frequently characterized by impaired learning and memory. The mechanism(s) responsible for these most troublesome symptoms is associated with death of neuronal cells. At a molecular level, the basis for changes in memory formation and consolidation has been linked to the activity of histone deacetylylases chromatin structures (Korzus, E. et al., *Neuron* (2004) 42:961-972; Levenson, J. M. et al., *The Journal of Biological Chemistry* (2004) 279:40545-40559).

Histone deacetylases also play a significant role in inflammatory diseases (Hildemann et al. Appl Microbiol Biotechnol (2007), 75(3), 487-497; Riester et al. Appl Microbiol Biotechnol (2007), 75(3), 499-514; Adcock, I M. Br J Pharmacol (2007), 150(7), 829-831; Huang L, J Cell Physiol (2006), 209(3), 611-616). Diverse cellular functions including the regulation of inflammatory gene expression, DNA repair and cell proliferation are regulated by changes in the acetylation status of histones and non-histone proteins. Recently, in vitro and in vivo data indicate that HDAC inhibitors may be anti-inflammatory due to their effects on cell death acting through acetylation of non-histone proteins. Although there are concerns over the long-term safety of these agents, they may prove useful particularly in situations where current anti-inflammatory therapies are suboptimal (Adcock, I M. Br J Pharmacol (2007), 150(7), 829-831).

Histone deacetylase inhibitors are also proposed as potential anti-HIV agents targeting Zn functional groups in retroviral zinc finger domains, based on the hypothesis and data advanced by Song et al. (2002) "Synthesis and Biological Properties of Amino Acid Amide Ligand-Based Pyridinioalkanoyl Thioesters as Anti-HIV agents" Bioorganic & Medicinal Chemistry 10, 1263-1273.

Histone deactylase inhibitors are also proposed as potential inhibitors of cardiac hypertrophy based on the data advanced by the following references: WO 2007021682, WO 2006129105, WO 2007014029, WO 2006023603, U.S. Patent Application Publication No. 2007-0004771, U.S. Patent Application Publication 2007-0135433, U.S. Patent Application Publication 2006-0235231, EP 1663310, U.S. Patent Application Publication 2007-0135365, EP 1694688, EP 1715870, EP 1691891, JP 2007511528, EP 1699436, and JP 2007514665.

The major structural group of HDAC inhibitors includes a hydroxamic acid component, presumed to be critical to the inhibitory activity of these molecules by their ability to bind zinc. Several other types of zinc binding groups as components of novel HDAC inhibitors are under evaluation. We have developed a novel series of HDAC inhibitors using a mercaptobenzaminoyl group as the zinc binder and believe that this moiety could be used in place of the hydroxamic acid and other zinc binding moieties on all other HDAC inhibitors to potential advantage. The synthesis of these HDAC inhibitors is described herein.

The compounds disclosed herein are also active inhibitors of proliferation of human cancer cells. These compounds inhibit the activity of histone deacetylase 3 and histone deacetylase 4 (HDAC3 and HDAC4, respectively), and also affect the stability of N-CoR in human brain cell lines (U-87) when cells are exposed to these compounds in culture.

SUMMARY OF THE INVENTION

This invention provides the compound having the structure

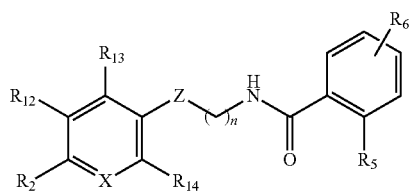

wherein n is 1-10;

X is C—$R_{11}$ or N, wherein $R_{11}$ is H, OH, SH, F, Cl, $SO_2R_7$, $NO_2$, trifluoromethyl, methoxy, or CO—$R_7$, wherein. $R_7$ is alkyl, alkenyl, alkynyl, $C_3$-$C_8$ cycloalkyl, or aryl;

Z is

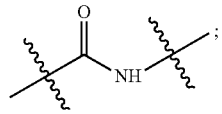 [SMILES: *NC(*)=O]

$R_2$ is H or $NR_3R_4$, wherein $R_3$ and $R_5$ are each independently H, $C_1$-$C_6$ alkyl, or $C_3$-$C_6$ cycloalkyl;

$R_5$ is OH or SH; and $R_6$, $R_{12}$, $R_{13}$, and $R_{14}$ are each independently H, OH, SH, F, Cl, $SO_2R_{15}$, $NO_2$, trifluoromethyl, methoxy, or CO—$R_{15}$, wherein $R_{15}$ is alkyl, alkenyl, alkynyl, $C_3$-$C_8$ cycloalkyl, or aryl, or a salt of the compound.

This invention provides a process for preparing a compound having the structure:

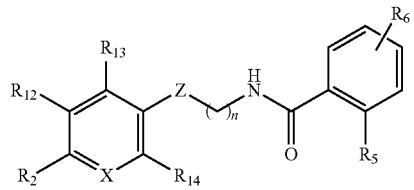

wherein n is 1-10;

X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;

Z is

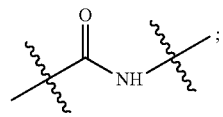 [SMILES: *NC(*)=O]

$R_2$ is H or $NR_3R_4$, wherein $R_3$ and $R_4$ are each independently H, $C_1$-$C_6$ alkyl, or $C_3$-$C_6$ cycloalkyl;

$R_5$ is OH or SH; and $R_6$, $R_{12}$, $R_{13}$, and $R_{14}$ are each independently H, OH, SH, F, Cl, $SO_2R_{15}$, $NO_2$, trifluoromethyl, methoxy, or CO—$R_{15}$, wherein $R_{15}$ is alkyl, alkenyl, alkynyl, $C_3$-$C_8$ cycloalkyl, or aryl;

comprising:

a) contacting a compound having the structure

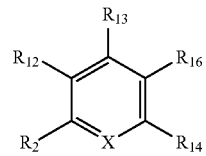

wherein $R_{16}$ is

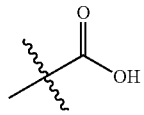

or $NH_2$, with a compound having the structure

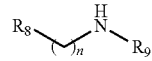

wherein $R_8$ is

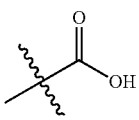 [SMILES: *C(=O)O]

or NH, $R_9$ is H or

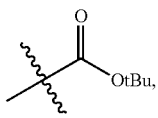

and with a compound having the structure

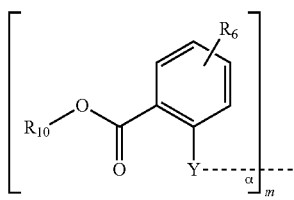

wherein $R_{10}$ is H or Me,
m is 1 or 2, and
when n is 1, α is absent, Y is OH or SH; or
when m is 2, α is present, and Y is S, to form the compound having the structure

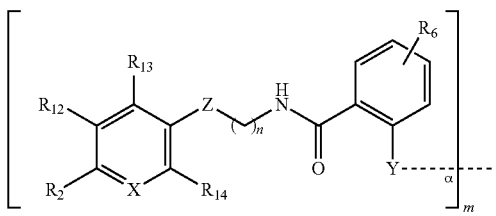

wherein Z is

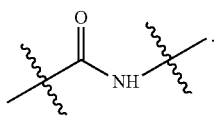 [SMILES: *NC(*)=O]

This invention provides a method of treating a subject with a neurodegenerative disease comprising administering to the subject a compound having the structure

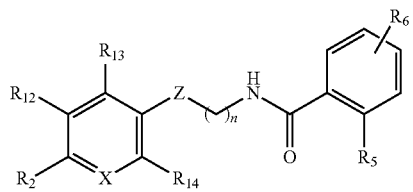

wherein
n is 1-10;
X is C—$R_{11}$ or N, wherein $R_{11}$ is H, OH, SH, F, Cl, $SO_2R_7$, $NO_2$ trifluoromethyl, methoxy, or CO—$R_7$, wherein $R_7$ is alkyl, alkenyl, alkynyl, $C_3$-$C_8$ cycloalkyl, or aryl;
Z is

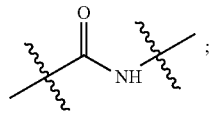 [SMILES: *NC(*)=O]

$R_2$ is H or $NR_3R_4$, wherein $R_3$ and $R_4$ are each independently H, $C_1$-$C_6$ alkyl, or $C_3$-$C_8$ cycloalkyl;
$R_5$ is OH or SH; and
$R_6$, $R_{12}$, $R_{13}$, and $R_{14}$ are each independently H, OH, SH, F, Cl, $SO_2R_{15}$, $NO_2$, trifluoromethyl, methoxy, or CO—$R_{15}$,
wherein $R_{15}$ is alkyl, alkenyl, alkynyl, $C_3$-$C_8$ cycloalkyl, or aryl, or
a salt of the compound in an amount effective to treat the subject.

This invention provides a method for reducing the aggregation of Tau protein in a cell comprising contacting the cell with an effective amount of a compound having the structure

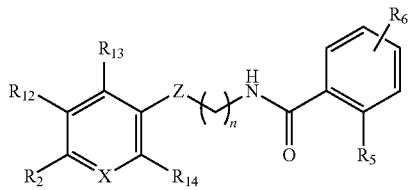

wherein
n is 1-10;
X is C—$R_1$ or N, wherein $R_{11}$ is H, OH, SH, F, Cl, $SO_2R_7$, $NO_2$, trifluoromethyl, methoxy, or CO—$R_3$, wherein $R_7$ is alkyl, alkenyl, alkynyl, $C_3$-$C_8$ cycloalkyl, or aryl;
Z is

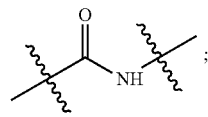 [SMILES: *NC(*)=O]

$R_2$ is H or $NR_3R_4$, wherein $R_3$ and $R_4$ are each independently H, $C_1$-$C_6$ alkyl, or $C_3$-$C_8$ cycloalkyl;
$R_5$ is OH or SH; and
$R_6$, $R_{12}$, $R_{13}$, and $R_{14}$ are each independently H, OH, SH, F, Cl, $SO_2R_{15}$, $NO_2$, trifluoromethyl, methoxy, or CO—$R_{15}$.

wherein $R_{18}$ is alkyl, alkenyl, alkynyl, $C_3$-$C_8$ cycloalkyl, or aryl, or a salt of the compound, so as to thereby inhibit the aggregation of Tau protein in the cell.

BRIEF DESCRIPTION OF THE FIGURES

FIG. 8A: Inhibition of the growth of breast cancer cell line, MDA-MB-231: Graphical representation (A) and curve fit with $IC_{50}$ value (B) of data obtained following exposure of MDA-MB-231 cells to compound 205 using the CellTiter-Glo assay. The effects of 10 µM doxorubicin that was used as a positive control are also shown in A. Each Each point represents the mean±SD of at least triplicate samples.

FIG. 8B: Inhibition of the growth of the colon cancer cell line HT-29: Graphical representation (A) and curve fit with $IC_{50}$ value (B) of data obtained following exposure of HT-29 cells to compound 205 using the CellTiter-Glo assay. The effects of 10 µM doxorubicin that was used as a positive control are also shown in A. Each point represents the mean±SD of at least triplicate samples.

FIG. 8C: Inhibition of the growth of the large cell lung cancer cell line NCI-H460: Graphical representation (A) and curve fit with $IC_{50}$ value (B) of data obtained following exposure of NCI-H460 cells to compound 205 using the CellTiter-Glo assay. The effects of 10 µM doxorubicin that was used as a positive control are also shown in A. Each point represents the mean±SD of at least triplicate samples.

FIG. 8D: Inhibition of the growth of the lung adenocarcinoma cell line NCI-H522: Graphical representation (A) and curve fit with $IC_{50}$ value (B) of data obtained following exposure of NCI-H522 cells to compound 205 using the CellTiter-Glo assay. The effects of 10 µM doxorubicin that was used as a positive control are also shown in A. Each point represents the mean±SD of at least triplicate samples.

FIG. 8E: Inhibition of the growth of the lung small-cell cell line NCI-H69: Graphical representation (A) and curve fit with $IC_{50}$ value (B) of data obtained following exposure of NCI-H69 cells to compound 205 using the CellTiter-Glo assay. The effects of 10 µM doxorubicin that was used as a positive control are also shown in A. Each point represents the mean±SD of at least triplicate samples.

FIG. 8F: Inhibition of the growth of the stomach cancer cell line GXF-209: Graphical representation (A) and curve fit with $IC_{50}$ value (B) of data obtained following exposure of GXF-209 cells to compound 205 using the CellTiter-Glo assay. The effects of 10 µM doxorubicin that was used as a positive control are also shown in A. Each point represents the mean±SD of at least triplicate samples.

FIG. 8G: Inhibition of the growth of the liver cancer (hepatoma) cell line HepG2: Graphical representation (A) and curve fit with $IC_{50}$ value (B) of data obtained following exposure of HepG2 cells to compound 205 using the CellTiter-Glo assay. The effects of 10 µM doxorubicin that was used as a positive control are also shown in A. Each point represents the mean±SD of at least triplicate samples.

FIG. 8H: Inhibition of the growth of the ovary adenocarcinoma cell line OVCAR-3: Graphical representation (A) and curve fit with $IC_{50}$ value (B) of data obtained following exposure of OVCAR-3 cells to compound 205 using the CellTiter-Glo assay. The effects of 10 µM doxorubicin that was used as a positive control are also shown in A. Each point represents the mean±SD of at least triplicate samples.

FIG. 8I: Inhibition of the growth of the pancreas cancer cell line PANC-1: Graphical representation (A) and curve fit with $IC_{50}$ value (B) of data obtained following exposure of PANC-1 cells to compound 205 using the CellTiter-Glo assay. The effects of 10 µM doxorubicin that was used as a positive control are also shown in A. Each point represents the mean±SD of at least triplicate samples.

FIG. 8J: Inhibition of the growth of the prostate cancer cell line DU-145: Graphical representation (A) and curve fit with $IC_{50}$ value (B) of data obtained following exposure of DU-145 cells to compound 205 using the CellTiter-Glo assay. The effects of 10 µM doxorubicin that was used as a positive control are also shown in A. Each point represents the mean±SD of at least triplicate samples.

FIG. 8K: Inhibition of the growth of the prostate cancer cell line LNCAP: Graphical representation (A) and curve fit with $IC_{50}$ value (B) of data obtained following exposure of LNCAP cells to compound 205 using the CellTiter-Glo assay. The effects of 10 NM doxorubicin that was used as a positive control are also shown in A. Each point represents the mean±SD of at least triplicate samples.

FIG. 8L-N: Inhibition of the growth of the leukemia cell lines HL-60 (FIG. 9L), K562 (FIG. 8M), and MOLT4 (FIG. 8N): Graphical representation (A) and curve fit with $IC_{50}$ value (B) of data obtained following exposure of HL-60 (FIG. 8L), K562 (FIG. 8M), and MOLT4 (FIG. 8N) cells to compound 205 using the CellTiter-Glo assay. The effects of 10 µM doxorubicin that was used as a positive control are also shown in A. Each point represents the mean±SD of at least triplicate samples.

DETAILED DESCRIPTION OF THE INVENTION

Figure 1:
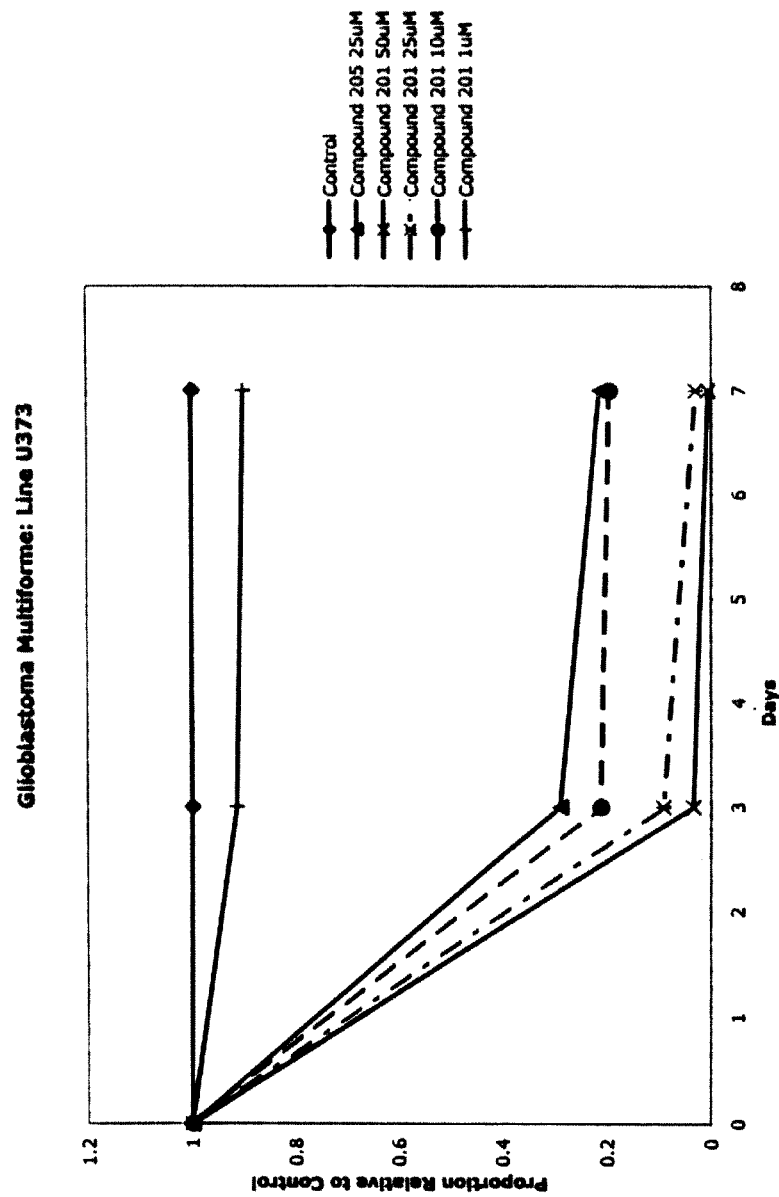
FIG. 1: Inhibition of growth of glioblastoma multiforme cell line U373 by compound 201 measured at 1, 3 and 7 days.
Figure 2:
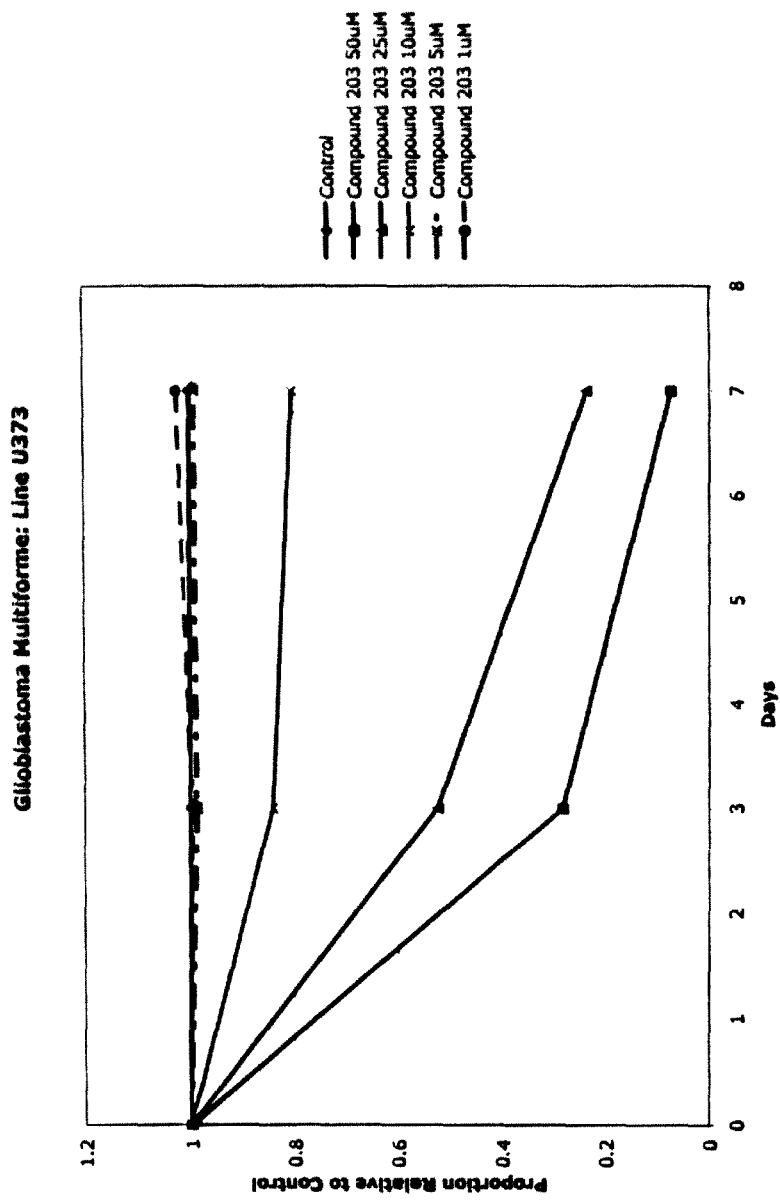
FIG. 2: Inhibition of growth of glioblastoma multiforme cell line U373 by compound 203 measured at 1, 3 and 7 days.
Figure 3:
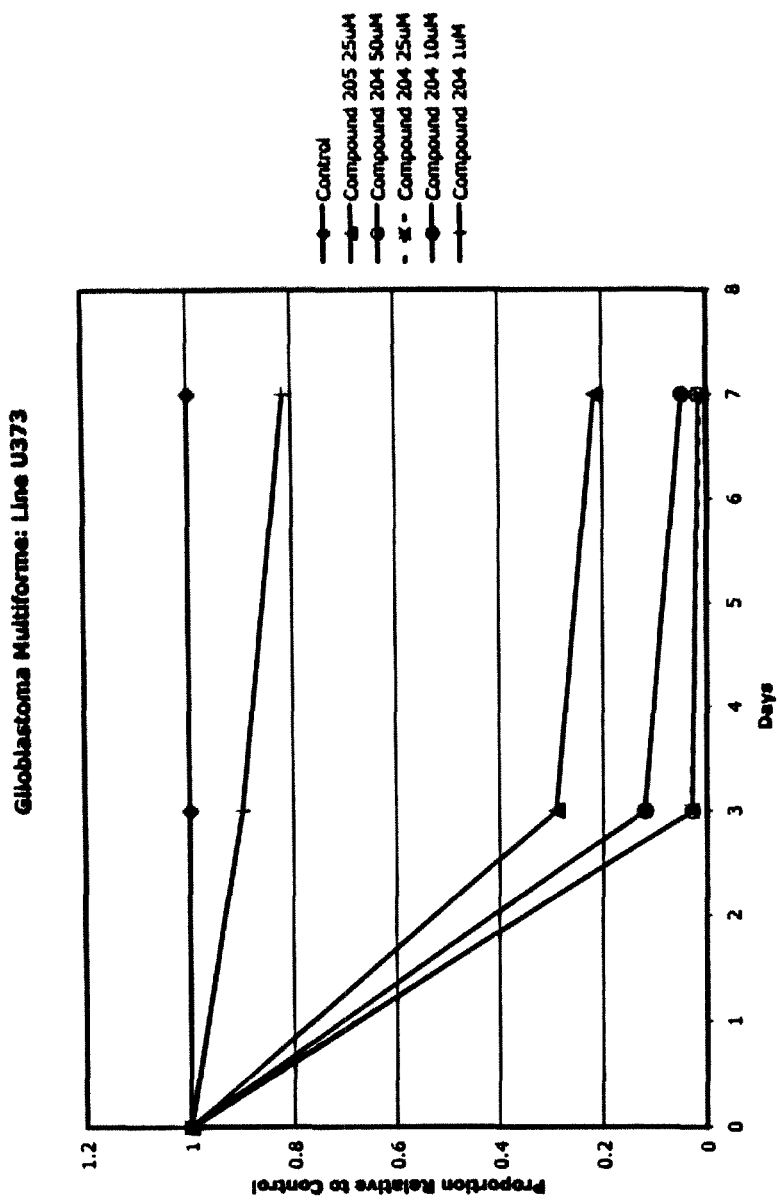
FIG. 3: Inhibition of growth of glioblastoma multiforme cell line U373 by compound 204 measured at 1, 3 and 7 days.
Figure 4:
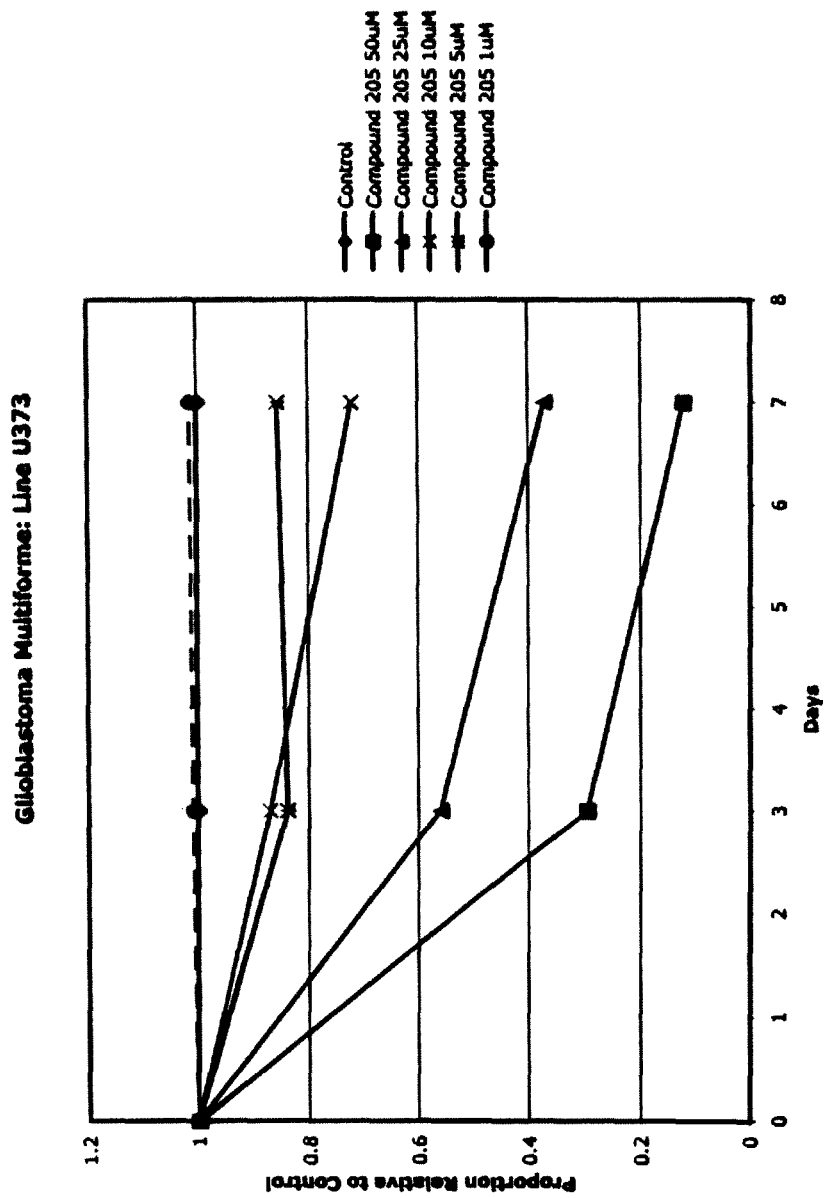
FIG. 4: Inhibition of growth of glioblastoma multiforme cell line U373 by compound 205 measured at 1, 3 and 7 days.
Figure 5:
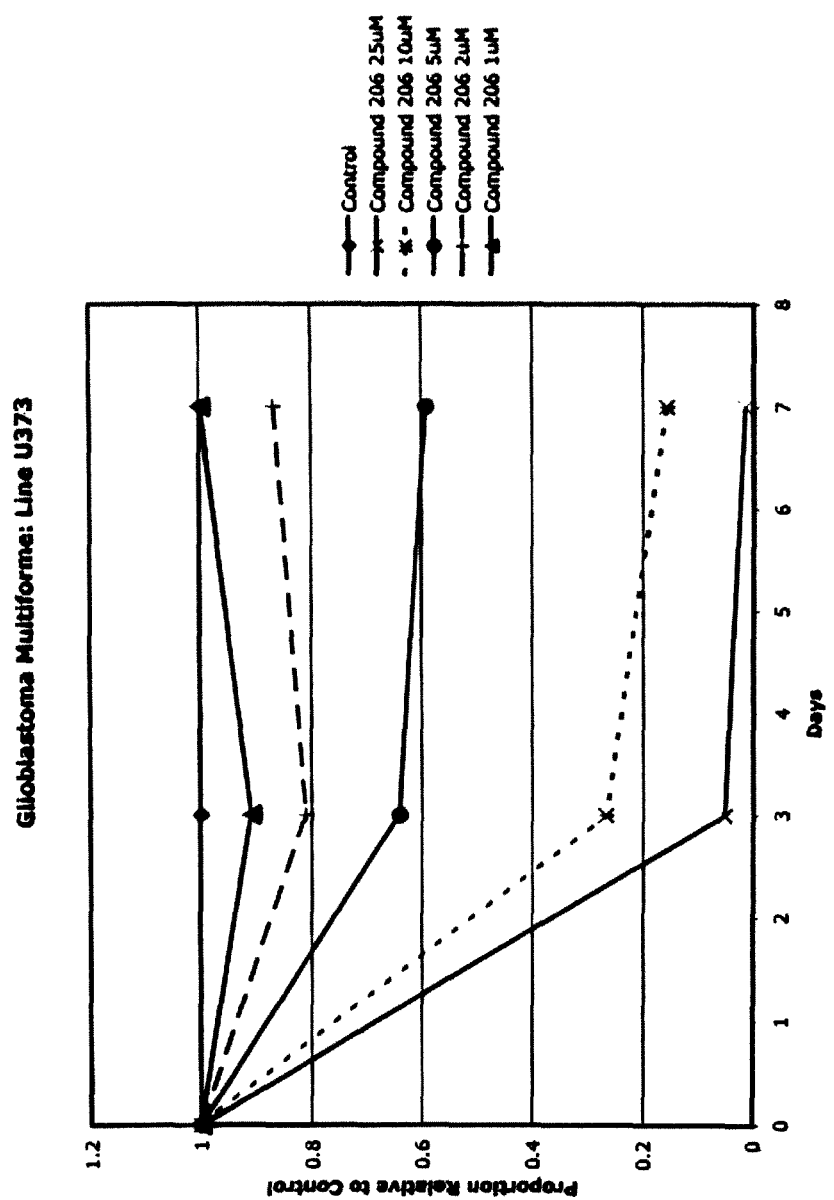
FIG. 5: Inhibition of growth of glioblastoma multiforme cell line U373 by compound 206 measured at 1, 3 and 7 days.

This inventions provides the compound having the structure

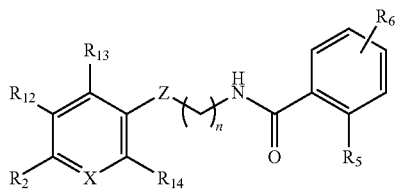

wherein
n is 1-10;
X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;
Z is

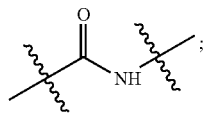 [SMILES: *NC(*)=O]

$R_2$ is H or $NR_3R_4$, wherein $R_3$ and $R_4$ are each independently H, $C_1$-$C_6$ alkyl, or $C_7$-$C_8$ cycloalkyl;
$R_3$ is OH or SH; and
$R_6$, $R_{12}$, $R_{13}$, and $R_{14}$ are each independently H, OH, SH, F, Cl, $SO_2R_{15}$, $NO_2$, trifluoromethyl, methoxy, or CO—$R_{15}$,
wherein $R_{15}$ is alkyl, alkenyl, alkynyl, $C_3$-$C_8$ cycloalkyl, or aryl, or
a salt of the compound.

In an embodiment, the compound has the structure

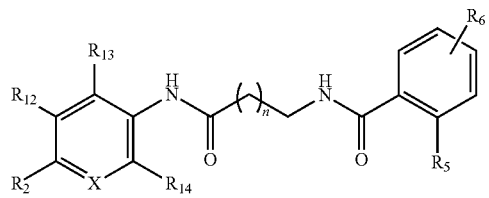

wherein
n is 1-9;
X is C—$R_{11}$ or N, wherein $R_{11}$ is H, OH, SH, F, Cl, $SO_2R_7$, $NO_2$, trifluoromethyl, methoxy, or CO—$R_7$ wherein $R_7$ is alkyl, alkenyl, alkynyl, $C_3$-$C_8$ cycloalkyl, or aryl;
$R_2$ is H or $NR_3R_4$, wherein $R_3$ and $R_4$ are each independently H, $C_1$-$C_6$ alkyl, or $C_3$-$C_8$ cycloalkyl;
$R_5$ is OH or SH; and
$R_6$, $R_{12}$, $R_{13}$, and $R_{14}$ are each independently H, OH, SH, F, Cl, $SO_2R_{15}$, $NO_2$, trifluoromethyl, methoxy, or CO—$R_{15}$, wherein $R_{15}$ is alkyl, alkenyl, alkynyl, $C_3$-$C_8$ cycloalkyl, or aryl.

In an embodiment, the compound has the structure

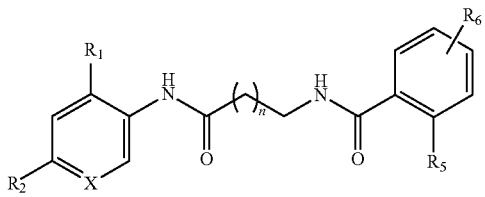

wherein
n is 1-8;
X is CH or N;
$R_1$ is H or OH;
$R_2$ is H or $NR_3R_4$, wherein $R_3$ and $R_4$ are each independently $C_1$-$C_8$ alkyl or $C_3$-$C_8$ cycloalkyl;
$R_5$ is OH or SH; and
$R_6$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl.

In an embodiment, the compound has the structure

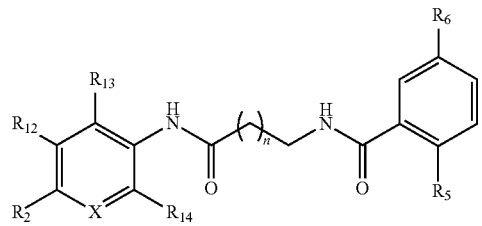

wherein
n is 1-9;
X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;
$R_2$ is H or $NR_3R_4$, wherein $R_3$ and $R_4$ are each independently H, $C_1$-$C_8$ alkyl, or $C_3$-$C_8$ cycloalkyl;
$R_5$ is OH or SH; and
$R_6$, $R_{12}$, $R_{13}$, and $R_{14}$ are each independently H, OH, SH, F, Cl, trifluoromethyl, methoxy, or CO—$R_{15}$, wherein $R_{15}$ is alkyl, alkenyl, alkynyl, $C_3$-$C_8$ cycloalkyl, or aryl.

In an embodiment, the compound has the structure

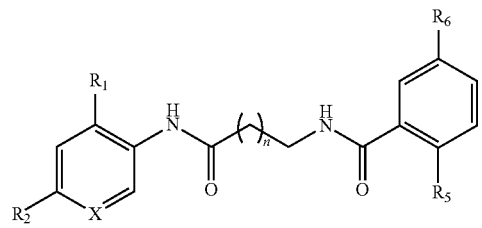

wherein
n is 1-8;
X is CH or N;
$R_1$ is H or OH;
$R_2$ is H or $NR_3R_4$, wherein $R_3$ and $R_4$ are each independently $C_1$-$C_6$ alkyl or $C_3$-$C_8$ cycloalkyl;
$R_5$ is OH or SH; and
$R_6$ is H, OH, SH, F, Cl, trifluoromethyl, methoxy, or CO—$R_7$, wherein $R_7$ is alkyl, alkenyl, alkynyl, or $C_3$-$C_8$ cycloalkyl, or aryl.

In an embodiment, the compound has the structure

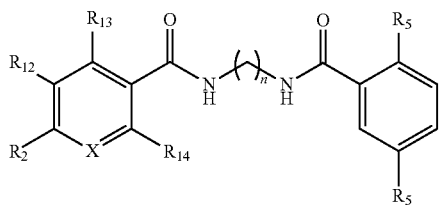

wherein
n is 1-8;
X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;
$R_2$ is H or $NR_3R_4$, wherein $R_3$ and $R_4$ are each independently $C_1$-$C_6$ alkyl or $C_3$-$C_8$ cycloalkyl; and
$R_5$ is OH or SH; and
$R_6$, $R_{12}$, $R_{13}$, and $R_{14}$ are each independently is H, OH, SH, F, Cl, $SO_2R_{15}$, $NO_2$, trifluoromethyl, methoxy, or CO—$R_{15}$,
wherein $R_{15}$ is alkyl, alkenyl, alkynyl, $C_3$-$C_8$ cycloalkyl, or aryl, or
a salt of the compound.

In an embodiment, the compound has the structure

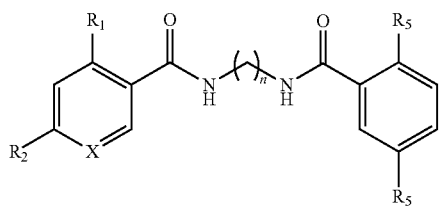

wherein
n is 1-8;
X is CH or N;
$R_1$ is H, OH or SH;
$R_2$ is H or $NR_3R_4$, wherein $R_3$ and $R_4$ are each independently $C_1$-$C_6$ alkyl or $C_3$-$C_8$ cycloalkyl; and
$R_5$ is OH or SH; and
$R_6$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl.

In embodiments of the instant compound, $R_5$ or $R_6$ is SH, and the aromatic ring bearing the SH group is a benzenoid, aza, or polyaza-aromatic five- or six-membered ring.

In an embodiment, $R_1$ and $R_2$ are H, X is CH, $R_5$ is SH, $R_6$ is H, and n is 4.

In an embodiment, $R_1$ is OH, $R_2$ is H, X is CH, $R_5$ is OH, $R_6$ is H, and n is 6.

In an embodiment, $R_1$ is SH, $R_2$ is H, X is CH, $R_5$ is SH, $R_6$ is H, and n is 6.

In an embodiment, $R_1$ and $R_2$ are H, X is N, $R_5$ is SH, $R_6$ is H, and n is 4.

In an embodiment, $R_1$ is H, $R_2$ is $NR_3R_4$, wherein $R_3$ and $R_4$ are each $C_1$ alkyl, X is CH, $R_5$ is SH, $R_6$ is H, and n is 4.

In an embodiment, $R_1$ and $R_2$ are H, X is N, $R_5$ is SH, $R_6$ is Cl, and n is 4.

In an embodiment, wherein $R_1$ and $R_2$ are H, X is N, $R_5$ is SH, $R_6$ is H, and n is 5.

In an embodiment, $R_1$ is H, $R_2$ is $NR_3R_4$, wherein $R_3$ and $R_4$ are each H, X is CH, $R_5$ is SH, $R_6$ is H, and n is 4.

In an embodiment, $R_1$ and $R_2$ are H, X is CH, $R_5$ is SH, $R_6$ is Cl, and n is 4.

In an embodiment, $R_1$ and $R_2$ are H, X is CH, $R_5$ is SH, $R_6$ is methoxy, and n is 4.

In an embodiment, $R_1$ and $R_2$ are H, X is CH, $R_5$ is SH, $R_6$ is H, and n is 5.

In an embodiment, $R_1$ and $R_2$ are H, X is CH, $R_6$ is SH, $R_6$ is H, and n is 6.

In an embodiment, $R_1$ and $R_2$ are H, X is CH, $R_5$ is SH, $R_6$ is H, and n is 9.

In embodiments, the compound has the structure

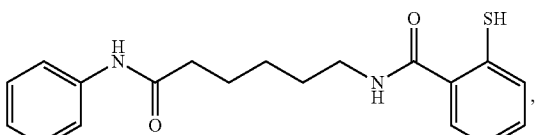

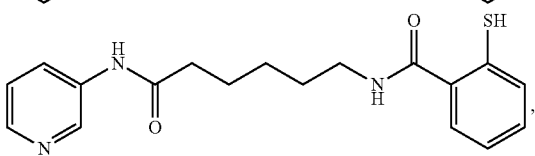

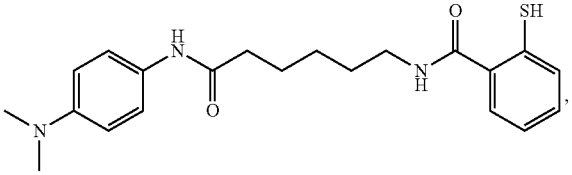

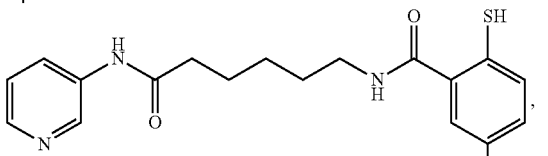

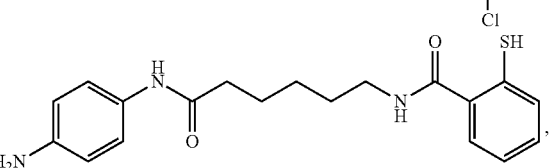

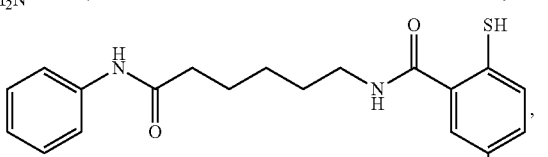

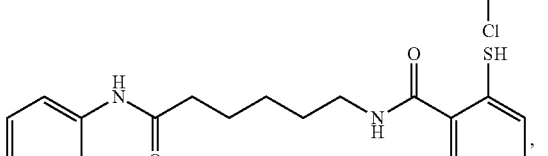

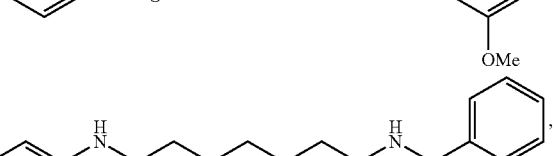

-continued

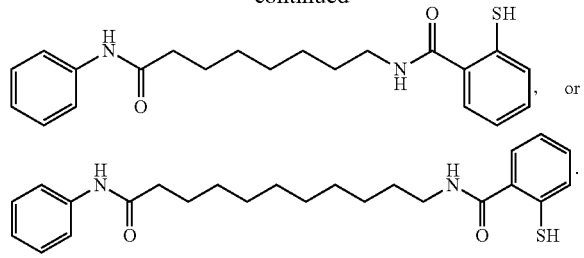

In embodiments, the compound has the structure

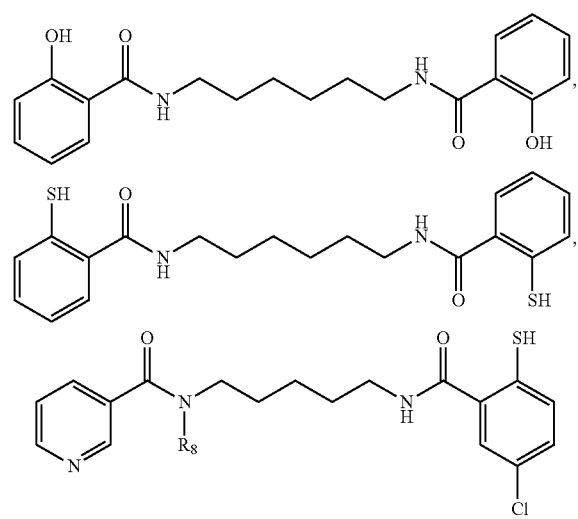

wherein $R_8$=H, alkyl, or aryl, or

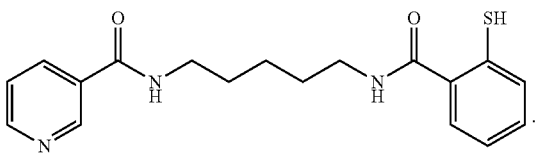 [SMILES: O=C(NCCCCCNC(=O)c1ccccc1S)c1cccnc1]

This invention provides a pharmaceutical composition comprising one or more of the above compounds or pharmaceutically acceptable salts thereof, and a pharmaceutically acceptable carrier.

This invention provides a method for reducing the size of a tumor overexpressing nuclear receptor corepressor (N-CoR) comprising administering to the subject the above pharmaceutical composition so as to reduce the size of the tumor.

In an embodiment of the instant method, the tumor overexpressing nuclear receptor corepressor (N-CoR) is a brain tumor.

This invention provides a method of inhibiting the activity of histone deactylase (HDAC) comprising contacting the HDAC with one or more of the above compounds so as to inhibit the activity of histone deacetylase.

In an embodiment, the HDAC is histone deacetylase 3 (HDAC3).

In an embodiment, the HDAC is histone deacetylase 4 (HDAC4).

This invention provides a method of inhibiting HIV replication comprising contacting an HIV-infected cell with one or more of the above compounds so as to inhibit HIV replication.

This invention provides a method of inhibiting cardiac hypertrophy comprising administering to the subject an amount of one or more of the above compounds effective to inhibit cardiac hypertrophy.

This invention provides a method of treating a subject afflicted with breast cancer, colon cancer, large cell lung cancer, adenocarcinoma of the lung, small cell lung cancer, stomach cancer, liver cancer, ovary adenocarcinoma, pancreas carcinoma, prostate carcinoma, promylocytic leukemia, chronic myelocytic leukemia, or acute lymphocytic leukemia, comprising administering to the subject the pharmaceutical composition above, thereby treating the subject.

This invention provides a method of inhibiting fungal growth comprising contacting the fungus with one or more of the above compounds so as to inhibit the growth of the fungus.

This invention provides process for preparing a compound having the structure:

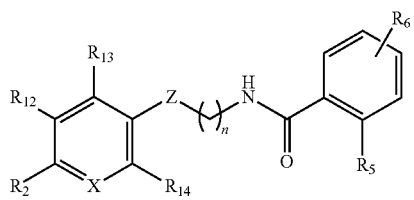

wherein n is 1-10;

X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;

Z is

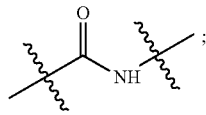 [SMILES: *NC(*)=O]

$R_2$ is H or $NR_3R_4$, wherein $R_3$ and $R_4$ are each independently H, $C_1$-$C_6$ alkyl, or $C_3$-$C_8$ cycloalkyl;

$R_5$ is OH or SH; and $R_6$, $R_{12}$, $R_{13}$, and $R_{14}$ are each independently H, OH, SH, F, Cl, $SO_2R_{15}$, $NO_2$, trifluoromethyl, methoxy, or CO—$R_{15}$, wherein $R_{15}$ is alkyl, alkenyl, alkynyl, $C_3$-$C_8$ cycloalkyl, or aryl; comprising:

a) contacting a compound having the structure

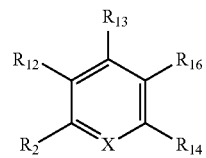

wherein $R_{16}$ is

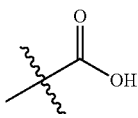

or $NH_2$, with a compound having the structure

wherein $R_8$ is

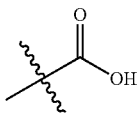

or $NH_2$, $R_9$ is H or

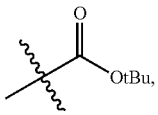 [SMILES: *C(=O)OC(C)(C)C]

and with a compound having the structure

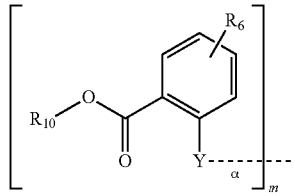

wherein $R_{10}$ is H or Me,
m is 1 or 2, and
when m is 1, α is absent, Y is OH or SH; or
when m is 2, α is present, and Y is S, to form the compound having the structure

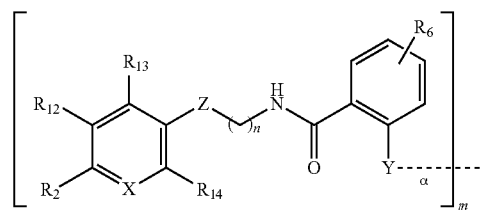

wherein Z is

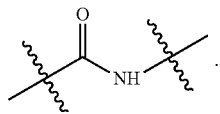 [SMILES: *NC(*)=O]

In an embodiment, the process for preparing a compound having the structure:

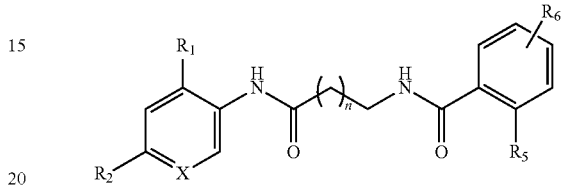

wherein
n is 1-9;
X is CH or N;
$R_1$ is H or OH;
$R_2$ is H or $NR_3R_4$, wherein $R_3$ and $R_4$ are each independently H, $C_1$-$C_6$ alkyl, or $C_3$-$C_8$ cycloalkyl;
$R_5$ is OH or SH; and
$R_6$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;

comprises:
a) contacting the compound having the structure

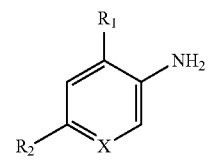

with a compound having the structure

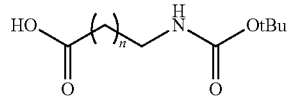

in the presence of one or more suitable first amide bond-forming reagents, a suitable first base, and a suitable first solvent to form the compound having the structure

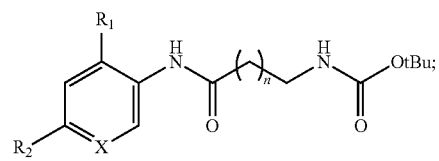

b) exposing the product of step a) to suitable deprotection conditions to form the compound having the structure

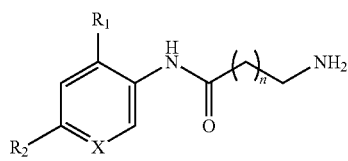

wherein the product is obtained as a free base or salt;

c) contacting the product of step b) with a compound having the structure

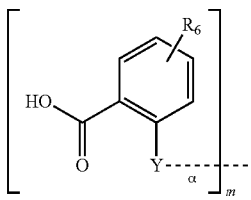

in the presence of one or more suitable second amide bond-forming reagents, a suitable second base, and a suitable second solvent to form the compound having the structure

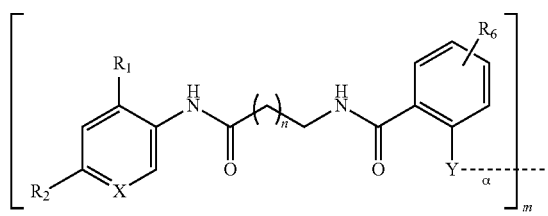

wherein m is 1 or 2, and
when m is 1, α is absent, Y is OH or SH; or
when m is 2, α is present, and Y is S.

In an embodiment, the instant process further comprises:

i) reacting the product of step c) with zinc in the presence of hydrochloric acid to obtain the compound having the structure

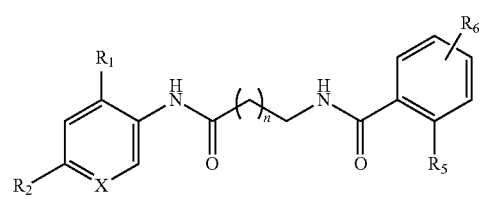

when m is 2, α is present, and Y is S.

In an embodiment, the process for preparing a compound having the structure:

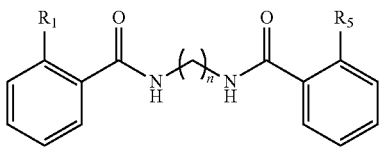

wherein
n is 1-8;
$R_1$ and $R_5$ are both OH or both SH;
comprises:

a) contacting a compound having the structure

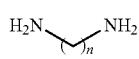

with at least two equivalents of a compound having the structure

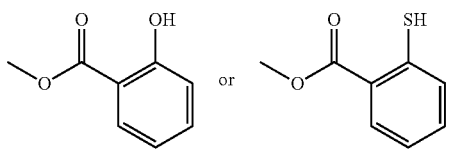

so as to form the compound having the structure

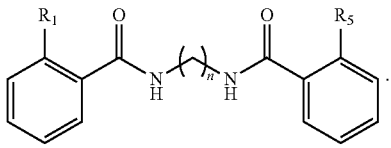

In an embodiment, the process for preparing the compound having the structure

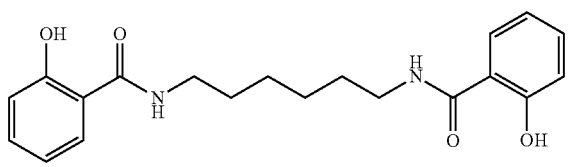 [SMILES: O=C(NCCCCCCNC(=O)c1ccccc1O)c1ccccc1O]

comprises:

a) heating methyl 2-hydroxybenzoate and 1,6-diaminohexane in a flask with a Dean-Stark apparatus to distill methanol;
b) cooling flask to room temperature and triturating with water;
c) collecting the solid in the flask by filtration; and
d) recrystallizing the solid from alcohol.

In an embodiment, the process for preparing a compound having the structure:

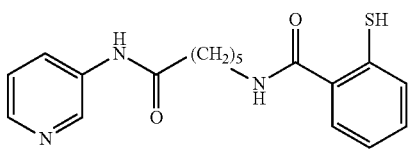

comprises:
a) combining 3-aminopyridine, 6-tert-Butoxycarbonyl amino-hexanoic acid in methylene chloride;
b) adding HOBt, EDC.HCl and DIPEA to the mixture of step a); and
c) stirring the mixture of step b) for 3 hours at room temperature to produce the compound

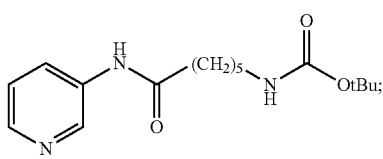

d) allowing the compound of step c) to react under deprotection conditions to produce the compound

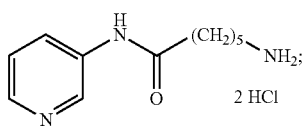

e) combining 2,2'-dithiodibenzoic acid, HOBt, EDC.HCl and DMF;
f) adding the compound of step d) to the mixture of step e) and DIPEA and stirring at room temperature overnight;
g) pouring the product of step f) into water and extracting with ethyl acetate;
h) washing the organic layer with brine, drying with sodium sulfate, and concentrating;
i) purifying the crude residue with column chromatography to produce the compound

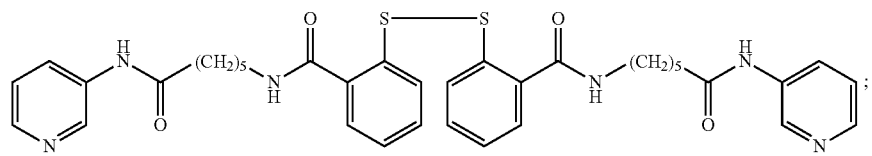
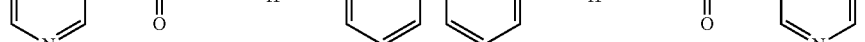

j) dissolving the compound of step i) in ice-cold methanol and methylene chloride and adding concentrated HCl and Zn dust;
k) stirring the mixture of step j) for 4 hours and diluting the mixture with water and methylene chloride;
l) separating the aqueous layer and adding aqueous saturated sodium bicarbonate and then cooling;

m) collecting the solid by filtering, followed by drying overnight;
n) extracting the dried solid using a mixture of hot methanol and methylene chloride;
o) filtering the hot solution through glass filter paper; and
p) evaporating the filtrate to dryness and triturating with ethyl acetate to produce the compound

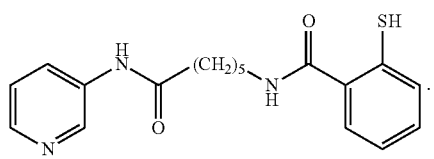

This invention provides a method of treating a subject with a neurodegenerative disease comprising administering to the subject a compound having the structure

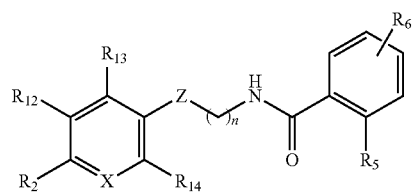

wherein
n is 1-10;
X is C—$R_{11}$ or N, wherein $R_{11}$ is H, OH, SH, F, Cl, $SO_2R_7$, $NO_2$, trifluoromethyl, methoxy, or CO—$R_7$, wherein $R_5$ is alkyl, alkenyl, alkynyl, $C_3$-$C_6$ cycloalkyl, or aryl;
Z is

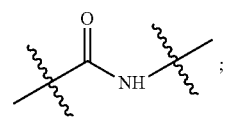 [SMILES: *NC(*)=O]

$R_2$ is H or $NR_3R_4$, wherein $R_5$ and $R_4$ are each independently H, $C_1$-$C_6$ alkyl, or $C_3$-$C_6$ cycloalkyl;
$R_5$ is OH or SH; and $R_6$, $R_{12}$, $R_{13}$, and $R_{16}$ are each independently H, OH, SH, F, Cl, $SO_2R_{15}$, $NO_2$, trifluoromethyl, methoxy, or CO—$R_{15}$,
wherein $R_7$ is alkyl, alkenyl, alkynyl, $C_3$-$C_8$ cycloalkyl, or aryl, or
a salt of the compound in an amount effective to treat the subject.

In an embodiment, the method comprises administering to the subject a compound having the structure

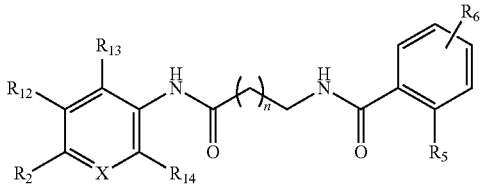

wherein
n is 1-9;
X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;
$R_2$ is H or $NR_3R_4$, wherein $R_3$ and $R_4$ are each independently H, $C_1$-$C_6$ alkyl, or $C_7$-$C_8$ cycloalkyl;
$R_5$ is OH or SH; and
$R_6$, $R_{12}$, $R_{13}$, and $R_{14}$ are each independently H, OH, SH, F, Cl, $SO_2R_{15}$, $NO_2$, trifluoromethyl, methoxy, or CO—$R_{15}$,
wherein $R_{15}$ is alkyl, alkenyl, alkynyl, $C_3$-$C_8$ cycloalkyl, or aryl; or
a salt of the compound.

In an embodiment, the method comprises administering to the subject a compound having the structure

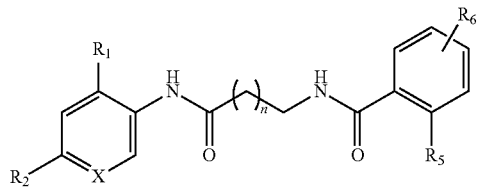

wherein
n is 1-9;
X is CH or N;
$R_1$ is H or OH;
$R_2$ is H or $NR_3R_4$, wherein $R_3$ and $R_4$ are each independently H, $C_1$-$C_8$ alkyl, or $C_3$-$C_8$ cycloalkyl;
$R_5$ is OH or SH; and
$R_6$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;
or a salt of the compound.

In an embodiment, the method comprises administering to the subject a compound having the structure

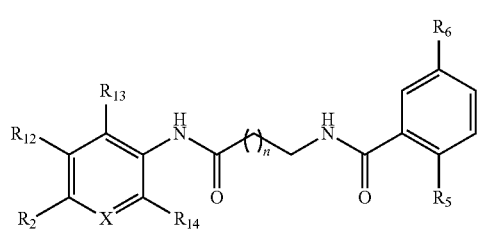

wherein
n is 1-9;
X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;

$R_2$ is H or $NR_3R_4$, wherein $R_3$ and $R_4$ are each independently H, $C_1$-$C_6$ alkyl, or $C_3$-$C_8$ cycloalkyl;
$R_5$ is OH or SH; and
$R_6$, $R_{12}$, $R_{43}$, and $R_{14}$ are each independently H, OH, SH, F, Cl, trifluoromethyl, methoxy, or CO—$R_{15}$, wherein $R_{15}$ is alkyl, alkenyl, alkynyl, $C_3$-$C_8$ cycloalkyl, or aryl; or
a salt of the compound.

In an embodiment, the method comprises administering to the subject a compound having the structure

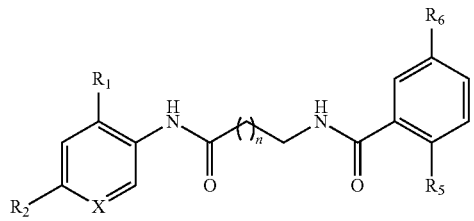

wherein
n is 1-9;
X is CH or N;
$R_1$ is H or OH;
$R_2$ is H or $NR_3R_4$, wherein $R_3$ and $R_4$ are each independently H, $C_1$-$C_6$ alkyl, or $C_3$-$C_8$ cycloalkyl;
$R_5$ is OH or SH; and
$R_5$ is H, OH, SH, F, Cl, trifluoromethyl, methoxy, or CO—$R_7$, wherein $R_7$ is alkyl, alkenyl, alkynyl, $C_3$-$C_8$ cycloalkyl, or aryl; or
a salt of the compound.

In an embodiment, the method comprises administering to the subject a compound having the structure

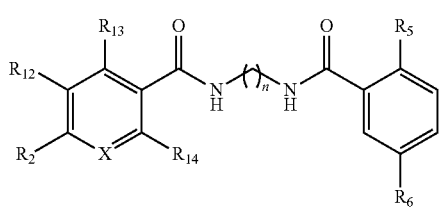

wherein
n is 1-8;
X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;
$R_2$ is H or $NR_3R_4$, wherein $R_3$ and $R_4$ are each independently $C_1$-$C_6$ alkyl or $C_3$-$C_9$ cycloalkyl; and
$R_5$ is OH or SH; and
$R_6$, $R_{12}$, $R_{13}$, and $R_{14}$ are each independently is H, OH, SH, F, Cl, $SO_2R_7$, $NO_2$ trifluoromethyl, methoxy, or CO—$R_7$,
wherein $R_7$ is alkyl, alkenyl, alkynyl, $C_3$-$C_8$ cycloalkyl, or aryl, or
a salt of the compound.

In an embodiment, the method comprises administering to the subject a compound having the structure

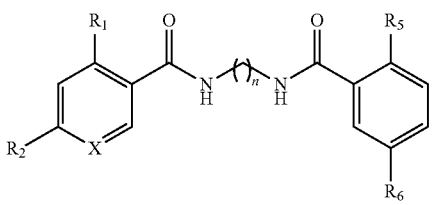

wherein n is 1-8;

X is CH or N;

$R_1$ is H, OH or SH;

$R_2$ is H or $NR_3R_4$, wherein $R_3$ and $R_4$ are each independently $C_1$-$C_6$ alkyl or $C_3$-$C_8$ cycloalkyl; and $R_5$ is OH or SH; and $R_6$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;

or a salt of the compound.

In embodiments of the instant method, the subject is a human.

In embodiments of the instant method, the neurodegenerative disease is Alzheimer's disease, Mild Cognitive Impairment, Parkinsons Disease, Frontotemporal Dementia, Dementia, or Lewy Body Dementia.

In an embodiment, the neurodegenerative disease is Alzheimer's disease.

In an embodiment, the methods further comprise administering to the subject an NMDA receptor antagonist, an acetylcholinesterase inhibitor, an anti-amyloid antibody, a 5-HT6 antagonist, a gamma secretase inhibitor, a beta secretase inhibitor, or an inhibitor of aggregation of amyloid-β peptide.

In embodiments, the method further comprise administering to the subject a tau aggregation inhibitor. Examples of tau aggregation inhibitors include methylthioninium chloride, naphthoquinone derivatives, and anthraquinones.

In an embodiment, the neurodegenerative disease is Parkinson's disease.

In an embodiment, the methods further comprise administering to the subject a dopamine receptor agonist.

This invention provides a method for reducing the aggregation of Tau protein in a cell comprising contacting the cell with an effective amount of a compound having the structure

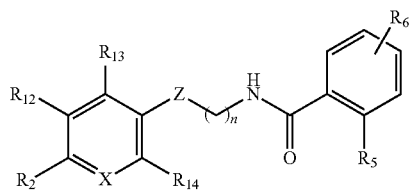

wherein n is 1-10;

X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;

Z is

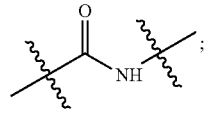

$R_2$ is H or $NR_3R_5$, wherein $R_3$ and $R_4$ are each independently H, $C_1$-$C_6$ alkyl, or $C_3$-$C_8$ cycloalkyl;

$R_5$ is OH or SH; and $R_6$, $R_{12}$, $R_{13}$, and $R_{14}$ are each independently H, OH, SH, F, Cl, $SO_2R_{15}$, $NO_2$, trifluoromethyl, methoxy, or CO—$R_{15}$, wherein $R_{15}$ is alkyl, alkenyl, alkynyl, $C_3$-$C_8$ cycloalkyl, or aryl, or a salt of the compound, so as to thereby inhibit the aggregation of Tau protein in the cell.

In an embodiment, the method comprises administering to the subject a compound having the structure

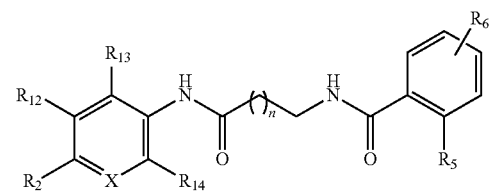

wherein n is 1-9;

X is C—$R_{11}$ or N, wherein $R_{11}$ is H, OH, SH, F, Cl, $SO_2R_7$, $NO_R$, trifluoromethyl, methoxy, or CO—$R_7$, wherein $R_7$ is alkyl, alkenyl, alkynyl, $C_3$-$C_8$ cycloalkyl, or aryl;

$R_2$ is H or $NR_3R_4$, wherein $R_3$ and $R_4$ are each independently H, $C_1$-$C_6$ alkyl, or $C_3$-$C_8$ cycloalkyl;

$R_5$ is OH or SH; and $R_5$, $R_{12}$, $R_{13}$, and $R_{14}$ are each independently H, OH, SH, F, Cl, $SO_2R_{15}$, $NO_2$ trifluoromethyl, methoxy, or CO—$R_{15}$, wherein $R_{15}$ is alkyl, alkenyl, alkynyl, $C_3$-$C_8$ cycloalkyl, or aryl; or a salt of the compound.

In an embodiment, the method comprises administering to the subject a compound having the structure

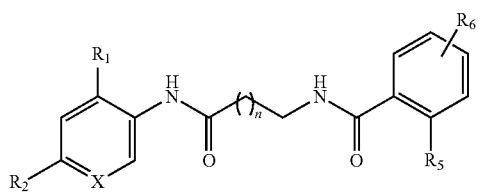

wherein n is 1-9;

X is CH or N;

$R_1$ is H or OH;

$R_2$ is H or $NR_3R_4$, wherein $R_3$ and $R_4$ are each independently H, $C_1$-$C_6$ alkyl, or $C_3$-$C_8$ cycloalkyl;

$R_6$ is OH or SH; and $R_6$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;

or a salt of the compound.

In an embodiment, the method comprises administering to the subject a compound having the structure

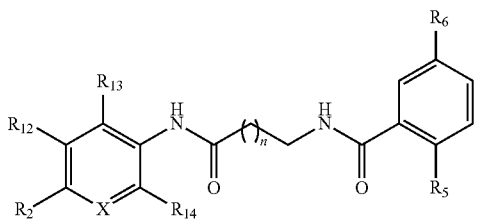

wherein
n is 1-9;
X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;
$R_2$ is H or $NR_3R_4$, wherein $R_3$ and $R_4$ are each independently H, $C_1$-$C_6$ alkyl, or $C_3$-$C_8$ cycloalkyl;
$R_5$ is OH or SH; and
$R_6$, $R_{12}$, $R_{13}$, and $R_{14}$ are each independently H, OH, SH, F, Cl, trifluoromethyl, methoxy, or CO—$R_{15}$, wherein $R_{15}$ is alkyl, alkenyl, alkynyl, $C_3$-$C_8$ cycloalkyl, or aryl; or a salt of the compound.

In an embodiment, the method comprises administering to the subject a compound having the structure

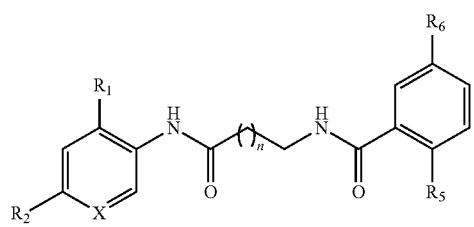

wherein
n is 1-9;
X is CH or N;
$R_1$ is H or OH;
$R_2$ is H or $NR_3R_8$, wherein $R_3$ and $R_4$ are each independently H, $C_1$-$C_6$ alkyl, or $C_3$-$C_8$ cycloalkyl;
$R_5$ is OH or SH; and
$R_6$ is H, OH, SH, F, Cl, trifluoromethyl, methoxy, or CO—$R_7$, wherein $R_7$ is alkyl, alkenyl, alkynyl, $C_3$-$C_8$ cycloalkyl, or aryl; or
a salt of the compound.

In an embodiment, the method comprises administering to the subject a compound having the structure

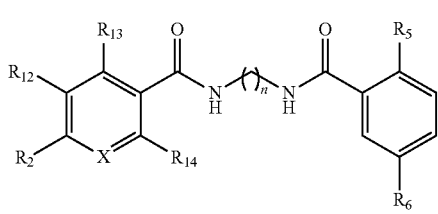

wherein
n is 1-8;
X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;

$R_2$ is H or $NR_3R_8$, wherein $R_3$ and $R_4$ are each independently $C_1$-$C_6$ alkyl or $C_3$-$C_8$ cycloalkyl; and
$R_5$ is OH or SH; and
$R_6$, $R_{12}$, $R_{13}$, and $R_{14}$ are each independently is H, OH, SH, F, Cl, $SO_2R_{18}$, $NO_2$, trifluoromethyl, methoxy, or CO—$R_{15}$,
wherein $R_{15}$ is alkyl, alkenyl, alkynyl, $C_3$-$C_8$ cycloalkyl, or aryl, or
a salt of the compound.

In an embodiment, the method comprises administering to the subject a compound having the structure

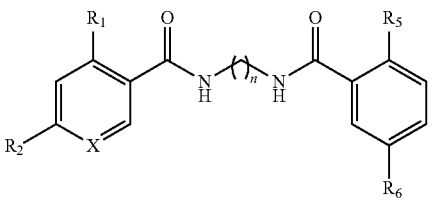

wherein
n is 1-8;
X is CH or N;
$R_1$ is H, OH or SH;
$R_2$ is H or $NR_3R_4$, wherein $R_3$ and $R_4$ are each independently $C_1$-$C_6$ alkyl or $C_3$-$C_8$ cycloalkyl; and
$R_5$ is OH or SH; and
$R_6$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl, or
a salt of the compound.

In embodiments of the instant method, the cell is a neural cell.

In embodiments, the cell is in a subject.

The invention provides a method of treating a patient suffering from a tumor overexpressing N-CoR comprising administering to the patient one or more of the compounds of this invention, alone or in combination with one or more retinoid receptor ligand, or one or more histone deacetylase ligands, or both, in each case in an amount effective to treat the patient.

The compounds of this invention may be used in combination with other compounds which inhibit the enzyme histone deacetylase (HDAC). These HDAC enzymes post-translationally modify histones (U.S. Patent Publication No. 2004/0197880, Armour et al.) Histones are groups of proteins which associate with DNA in eukaryotic cells to form compacted structures called chromatin. This compaction allows an enormous amount of DNA to be located within the nucleus of a eukaryotic cell, but the compact structure of chromatin restricts the access of transcription factors to the DNA. Acetylation of the histones decreases the compaction of the chromatin allowing transcription factors to bind to the DNA. Deacetylation, catalysed by histone deacetylases (HDACs), increases the compaction of chromatin, thereby reducing transcription factor accessibility to DNA. Therefore, inhibitors of histone deacetylases prevent the compaction of chromatin, allowing transcription factors to bind to DNA and increase expression of the genes.

In the methods of the invention, an assessment of the percentage of cells with N-CoR in the cytoplasm relative to the percentage of cells with N-CoR in the nucleus is representative of the ratio of the number of more-differentiated cells to the number of less-differentiated cells in a given tissue.

In the method of the invention, tumors that overexpress N-CoR may include glioblastoma multiforme, breast cancer, colorectal cancer, small cell lung cancer or ovarian cancer.

This invention also provides a method of inhibiting growth of a tumor overexpressing N-CoR in a patient, comprising administering to the patient one or more of the compounds of this invention, alone or in combination with one or more retinoid receptor ligand, one or more histone deacetylase ligand, or both, in each case in amounts effective to affect N-CoR so as to thereby induce differentiation of cells of the tumor overexpressing N-CoR and inhibit growth of the tumor in the patient.

As used herein, "therapeutically effective amount" means an amount sufficient to treat a subject afflicted with a disease (e.g. tumors overexpressing N-CoR) or to alleviate a symptom or a complication associated with the disease without undue adverse side effects (such as toxicity, irritation, or allergic response) commensurate with a reasonable benefit/risk ratio when used in the manner of this invention. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, "treating" means slowing, stopping or reversing the progression of a disease, particularly tumors overexpressing N-CoR.

As used herein, "alkyl" includes both branched and straight-chain saturated aliphatic hydrocarbon groups having the specified number of carbon atoms. Thus, $C_1$-$C_n$, as in "$C_1$-$C_n$ alkyl" is defined to include groups having 1, 2, ..., n−1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, propyl, butyl, pentyl, hexyl, and so on. In an embodiment the alkyl is $C_1$ (methyl).

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "alkenyl" refers to a non-aromatic hydrocarbon radical, straight or branched, containing at least 1 carbon to carbon double bond, and up to the maximum possible number of non-aromatic carbon-carbon double bonds may be present. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

The term "alkynyl" refers to a hydrocarbon radical straight or branched, containing at least 1 carbon to carbon triple bond, and up to the maximum possible number of non-aromatic carbon-carbon triple bonds may be present. Thus, "$C_2$-$C_6$ alkynyl" means an alkynyl radical having 2 or 3 carbon atoms and 1 carbon-carbon triple bond, or having 4 or 5 carbon atoms and up to 2 carbon-carbon triple bonds, or having 6 carbon atoms and up to 3 carbon-carbon triple bonds. Alkynyl groups include ethynyl, propynyl and butynyl.

As used herein, "aryl" is intended to mean any stable monocyclic, bicyclic or polycyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

In choosing compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry Part B: Reaction and Synthesis, Francis Carey and Richard Sundberg, (Springer) 5th ed. Edition. (2007), the content of which is hereby incorporated by reference.

The instant compounds may be in a salt form. As used herein, a "salt" is salt of the instant compounds which has been modified by making acid or base salts of the compounds. In the case of compounds used for treatment of cancer, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compositions of this invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds may comprise a single compound or mixtures thereof with anti-cancer compounds, or tumor growth inhibiting compounds, or with other compounds also used to treat neurite damage. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection or other methods, into the cancer, all using dosage forms well known to those of ordinary skill in the pharmaceutical arts.

The compounds can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone but are generally mixed with a pharmaceutically acceptable carrier. This carrier can be a solid or liquid, and the type of carrier is generally chosen based on the type of administration being used. In one embodiment the carrier can be a monoclonal antibody. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incoporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds may also be coupled to soluble polymers as targetable drug carriers or as a prodrug. Such polymers include polyvinylpyrrolidone, pyran copolymer, polyhydroxylpropylmethacrylamide-phenol, polyhydroxyethlasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The active ingredient can be administered orally in solid dosage forms, such as capsules, tablets, and powders, or in liquid dosage forms, such as elixirs, syrups, and suspensions. It can also be administered parentally, in sterile liquid dosage forms.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The instant compounds may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The compounds and compositions of the invention can be coated onto stents for temporary or permanent implantation into the cardiovascular system of a subject.

This invention will be better understood by reference to the Experimental Details which follow, but those skilled in the art will readily appreciate that the specific experiments detailed are only illustrative of the invention as described more fully in the claims which follow thereafter.

Experimental Details

Methods and Materials

Synthesis of
Bis-1,6-(2-hydroxybenzoylamino)hexane (203)

Scheme 1

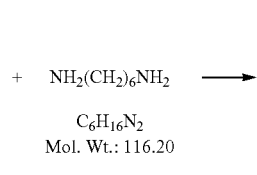

C$_8$H$_8$O$_3$
Mol. Wt.: 152.15

NH$_2$(CH$_2$)$_6$NH$_2$

C$_6$H$_{16}$N$_2$
Mol. Wt.: 116.20

-continued

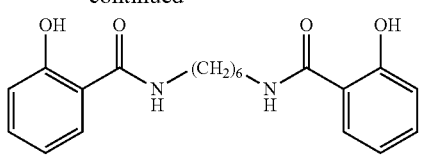

203

C$_{20}$H$_{24}$N$_2$O$_4$
Mol. Wt.: 356.42

Methyl 2-hydroxybenzoate (17.6 g, 115.65 mmole) and 1,6-diaminohexane (6.4 g, 55, 32.1 mmole) were heated in a 100 ml round-bottomed flask in a heating mantle using a Dean-Stark apparatus. After 20 minutes, methanol began to distil out of the reaction mixture into the Dean-Stark apparatus. Heating was continued for 40 minutes, and thereafter the mixture was cooled to room temperature and triturated with water (100 mL). The solid, which separated, was removed by filtration and air-dried overnight. The solid was recrystallized from alcohol which gave a first crop of the title compound (4 gm) and a second crop of 1.8 g both having mp 141-142° C. (lit. mp 141-142° C.). Total yield 5.8 g (30%). $^1$H NMR (CDCl$_3$) δ 12.30 (br s, 2H), 7.40 (m, 4H), 6.98 (d, 2H), 6.82 (t, 2H), 6.40 (br s, 2H), 3.42 (q, 4H), 1.70 (m, 4H), 1.41 (m, 4H). The experimental method is based on a literature procedure (J. Med. Chem. (1981); 24, 1245-1249).

Synthesis of
Bis-1,6-(2-mercaptobenzoylamino)hexane (204)

The title compound was synthesized in two steps starting from 1,6-diaminohexane and 2,2'-dithiodibenzoyl chloride as shown in Scheme 1.

Scheme 2

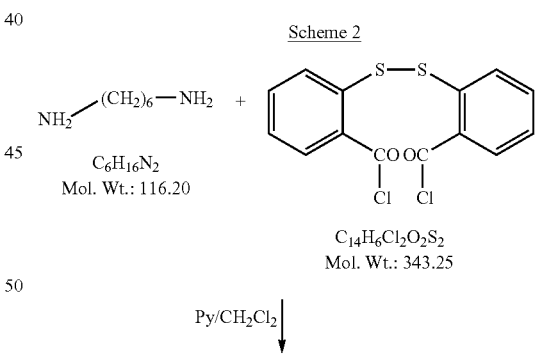

NH$_2$(CH$_2$)$_6$—NH$_2$

C$_6$H$_{16}$N$_2$
Mol. Wt.: 116.20

C$_{14}$H$_6$Cl$_2$O$_2$S$_2$
Mol. Wt.: 343.25

Py/CH$_2$Cl$_2$

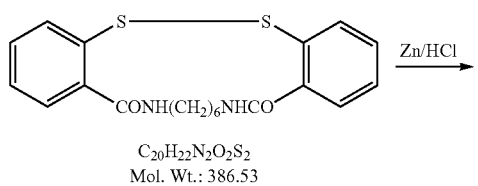

Zn/HCl

C$_{20}$H$_{22}$N$_2$O$_2$S$_2$
Mol. Wt.: 386.53

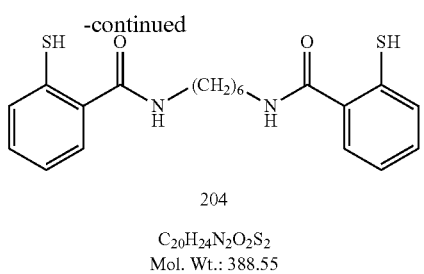

204

C$_{20}$H$_{24}$N$_2$O$_2$S$_2$
Mol. Wt.: 388.55

To a solution of 1,6-diaminohexane (465 mg, 4 mmole) in methylene chloride (20 mL) was added pyridine (3 mL) followed by a solution of 2,2'-dithiodibenzoyl dichloride (1.03 g, 3 mmole) in methylene chloride (5 mL). The reaction mixture was stirred at room temperature overnight. It was then evaporated to dryness and the product was purified by column chromatography using 2% methanol in methylene chloride which eluted the pure disulfide compound. Yield 0.365 g (31%, mp 220° C.). To the ice-cold solution of the disulfide derivative (0.365 g, 0.95 mmole) in a mixture of methanol (2 mL) and methylene chloride (5 mL) was added conc. HCl (0.57 mL, 6 mmole) followed by zinc dust (285 mg, 4.4 mg atom) in portions over 10 minutes. After stirring at 0-10° C. for 2 h, the residual zinc was removed by filtration and washed with a hot mixture of methanol and methylene chloride (50 mL). The filtrate was concentrated to dryness, redissolved in hot methanol (5 mL) and water (25 mL) was added. The separated solid was filtered, washed with water and dried to give bis-1,6-(2-mercaptobenzoylamino)-hexane. Yield 100 mg (27%, mp 133-135° C. (decomp)). $^1$H NMR (DMSO-d$_6$-D$_2$O) δ 7.01-7.40 (m, 8H), 3.22 (m, 4H), 1.26-1.62 (m, 8H). FAB (MH$^+$) 389.

Synthesis or 2-Mercapto-N-[5-(pyridine-3-ylcarbamoyl)pentyl]benzamine (205)

Step 1: [5-(pyridin-3-ylcarbamoyl)pentyl]carbamic acid tert-butyl ester (3)

Scheme 3

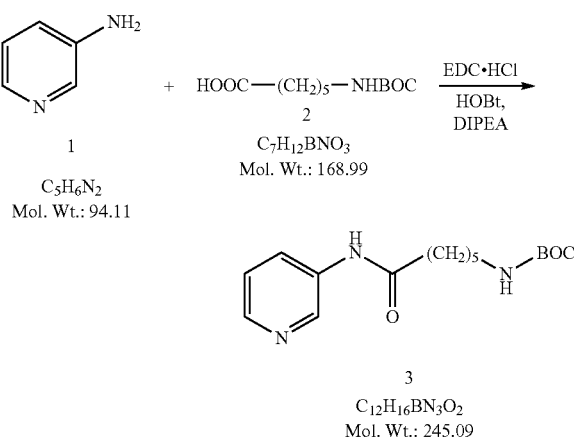

To a mixture of 3-aminopyridine (1, 2.82 g, 30 mmole) and 6-tert-Butoxycarbonylamino-hexanoic acid (2, 9.2 g, 40 mmole) in methylene chloride (50 mL) was added HOBt (135 mg, 1 mmole), EDC.HCl (7.6 g, 40 mmole) followed by DIPEA (10.45 mL, 60 mmole). The reaction mixture was stirred at room temperature for 3 h. At this point the TLC showed the disappearance of starting material. The reaction solution was washed with water (3×25 mL), followed by aqueous sodium bicarbonate (25 mL), then brine and finally dried over anhydrous sodium sulfate, filtered and concentrated. The crude residue was purified by column chromatography using 1% methanol in methylene chloride as the eluant to give the pure product as an oily residue. This residue on trituration with hexane gave 3 as a colorless solid (6.3 g, 68%, mp 96-98° C.). $^1$H NMR (CDCl$_3$) δ 8.68 (br s, 2H), 8.48 (m, 1H), 8.30 (m, 2H), 7.32 (m, 1H), 4.62 (br s, 1H), 3.16 (m, 2H), 2.40 (m, 2H), 2.78 (m, 2H), 1.50 (m, 4H), 1.40 (s, 9H).

Step 2: 6-Amino-N-(pyridin-3-yl)hexanoamide dihydrochloride (4)

Scheme 4

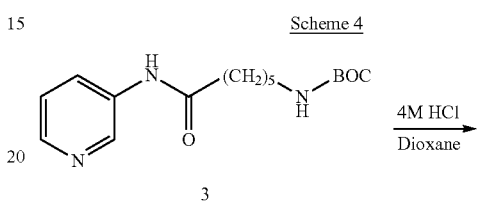

3

C$_{12}$H$_{16}$BN$_3$O$_2$
Mol. Wt.: 245.09

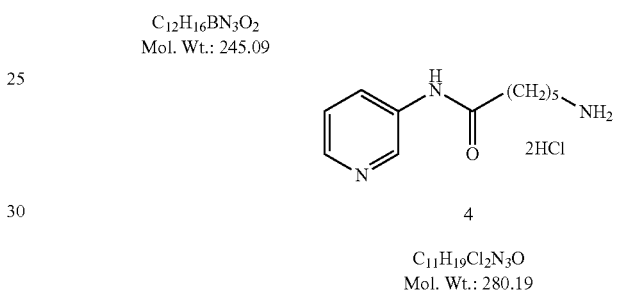

4

C$_{11}$H$_{19}$Cl$_2$N$_3$O
Mol. Wt.: 280.19

To an ice-cold mixture of (5-(Pyridin-3-ylcarbamoyl)pentyl)carbamic acid tert-butyl ester (3, 3.07 g, 10 mmole) in methylene chloride (30 mL) was added a solution of HCl in dioxane (4M, 10 mL). The mixture was stirred at room temperature overnight. The separated solid was filtered, washed with methylene chloride, dried in vacuum oven to give the product 4 as the hydrochloride salt (2.7 g, 96%). The $^1$H NMR spectrum of the pure solid was consistent with structure 4. $^1$H NMR (D$_2$O) δ 9.20 (s, 2H), 7.91 (m, 1H), 2.90 (t, 2H), 2.42 (t, 2H), 2.62 (m, 4H), 1.36 (m, 2H).

Alternative reaction conditions may be used to remove the BOC protecting group. The compound 4 can be prepared under standard amine deprotection conditions (for example, with 3.0 equivalents of 0.75M HCl (in ether), with stirring at room temperature for 12 hours. (See, P. Cali, M. Begtrup, *Synthesis*, 2002, 63-64.)

Similarly the following two compounds namely 6-Amino-N-(phenyl)hexanoamide dihydrochloride and 6-amino-N-(4-dimethylaminophenyl hexanoamide dihydrochloride [$^1$H NMR (CDCl$_3$) δ 7.32 (d, 2H), 6.67 (d, 2H), 2.91 (s, 6H), 2.68 (m, 2H), 2.31 (m, 2H), 1.72 (m, 2H), 1.43 (br m, 4H)] were synthesized using the above procedure.

Step 3: 2,2'-Dithio-bis(N-[5-(pyridin-3-ylcarbamoyl)pentyl]benzamide (6)

Scheme 5

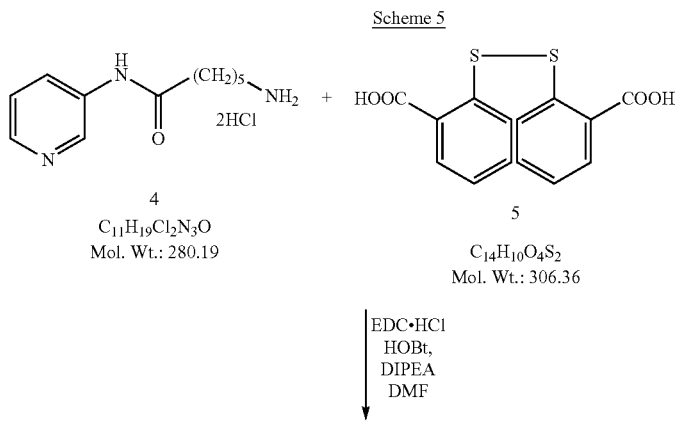

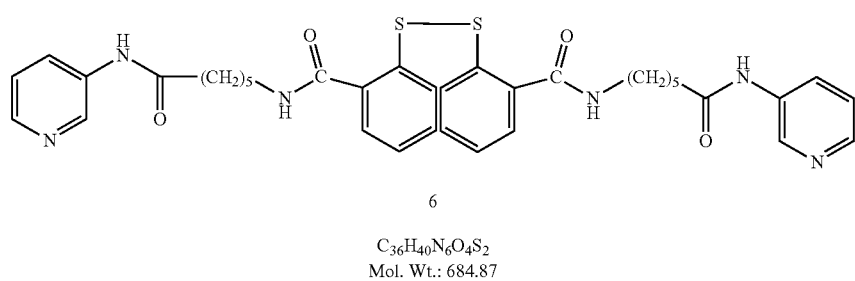

To a mixture 2-thiobenzoic acid disulfide (5, 0.765 g, 2.5 mmole), HOBt (0.665 g, 4.9 mmole), EDC. HCl (2 g, 10 mmole) in DMF (40 mL) was added the amine derivative 4 (1.5 g, 5 mmole) followed by DIPEA (3.5 mL, 20 mmole). The mixture was stirred at room temperature overnight. It was then poured into water and extracted with ethyl acetate (5×30 mL). The combined organic layers were washed with brine, dried over anhydrous sodium sulfate, filtered and concentrated. The crude residue was purified by column chromatography using 2 to 5% methanol in methylene chloride to elute the required product 6 (1 g, 27%) as a colorless solid. $^1$H NMR (DMSO-d$_6$) δ 10.01 (br s, 2H), 8.67 (s, 2H), 8.21 (d, 2H), 7.98 (m, 4H), 7.83 (d, 2H), 7.65 (t, 2H), 7.42 (t, 2H), 7.30 (m, 2H), 3.81 (t, 4H), 2.30 (t, 4H), 1.46 (m, 4H), 1.30 (m, 4H).

The following two compounds namely 2,2'Dithio-bis{N-(5-(phenylcarbamoyl)pentyl)benzamide and 2,2'Dithio-bis(N-[5-(4-dimethylaminophenylcarbamoyl)pentyl]benzamide} [$^1$H NMR (CDCl$_3$) δ 8.00 (d, 2H), 7.56 (m, 4H), 7.35 (m, 6H), 6.66 (d, 4H), 3.90 (t, 4H), 2.90 (s, 12H), 2.51 (t, 4H), 1.76 (m, 12H), 1.45 (m, 4H)] were also synthesized using the above procedure. The $^1$H NMR spectra of these two compounds are in agreement with the structures.

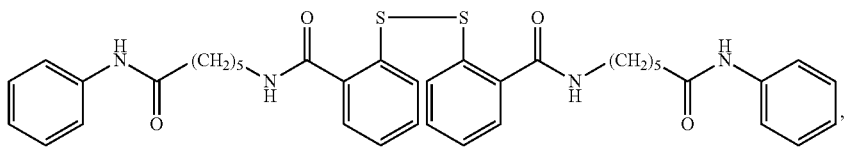

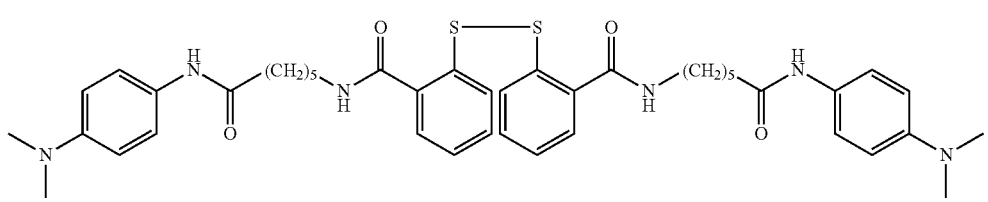

Step 4: 2-Mercapto-N-[5-(pyridin-3-ylcarbamoyl)pentyl]benzamide (205)

Scheme 6

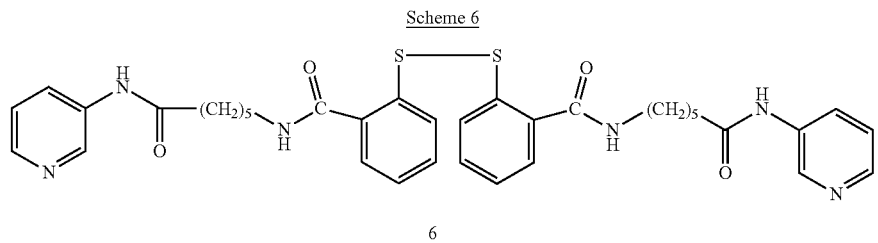

6

C$_{36}$H$_{40}$N$_{6}$O$_{4}$S$_{2}$
Mol. Wt.: 684.87

↓ Zn/HCl

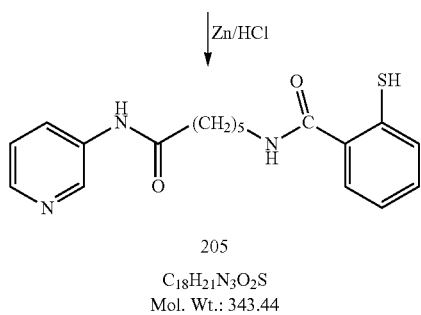

205

C$_{18}$H$_{21}$N$_{3}$O$_{2}$S
Mol. Wt.: 343.44

To an ice-cold solution of the disulfide derivative 6 (0.85 g, 1.2 mmole) in a mixture of methanol (10 mL) and methylene chloride (25 mL) was added conc. HCl (3.4 mL) followed by Zn dust (1.2 g) in portions over 10 minutes. After stirring at room temperature for 4 h, the mixture was diluted with water (30 mL) and methylene chloride (25 mL). The aqueous layer was separated and basified with aqueous saturated sodium bicarbonate while cooling the mixture simultaneously. The separated solid was filtered and air-dried overnight. The dried solid was extracted into a mixture of hot methanol and methylene chloride (200 mL, 2:3 ratio). The hot solution was then filtered through glass filter paper. The filtrate was evaporated to dryness and the residue was triturated with ethyl acetate to give the pure required product 205 (555 mg, 65%, mp 233-237° C.) as a colorless solid. $^1$H NMR (DMSO-d$_6$) δ 10.06 (br s, 1H), 9.41 (br s, 1H), 8.76 (d, 1H), 8.21 (d, 1H), 8.02 (d, 1H), 7.40 (m, 2H), 7.32 (m, 1H), 7.02 (t, 1H), 6.91 (t, 1H), 3.24 (q, 2H), 2.30 (t, 2H), 1.60 (m, 4H), 1.38 (m, 2H). FAB (MH$^+$) 344.

Using the above procedure the following two compounds namely 2-mercapto-N-[5-(phenylcarbamoyl)pentyl]benzamide (201), mp 110-112° C. and 2-Mercapto-N-[5-(4-dimethylaminocarbamoyl)pentyl]benzamide (206), mp 108-110° C. were synthesized. Their $^1$H NMR spectra are consistent, respectively, with the following structures:

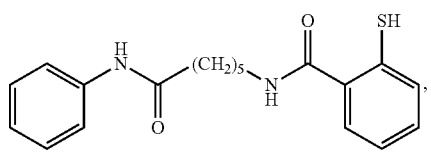

-continued

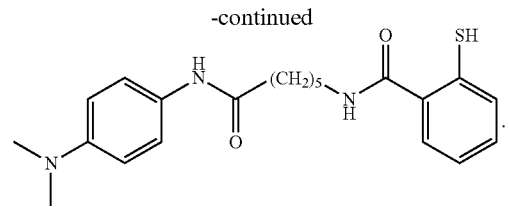

5-Chloro-2-mercapto-N-[4-(pyridin-3-ylcarbamoyl)pentyl]benzamide(207a)

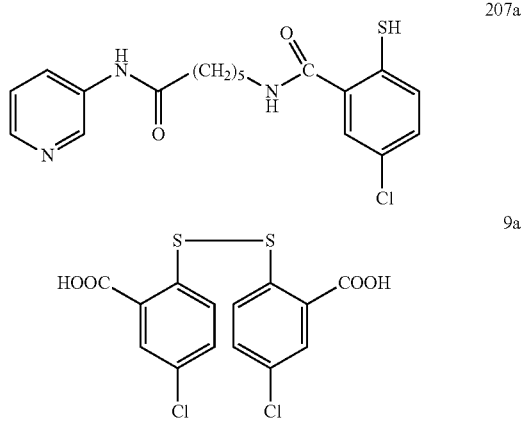

Using the above procedure the 5-Chloro-2-mercapto-N-[5-(pyridin-3-ylcarbamoyl)-pentyl]benzamide (207a), mp 238-

240° C. was prepared by treating the amine 4 in step 3 with 4,4'-dichloro-2,2'-dithiodibenzoic acid (9a) instead of 2,2'-dithiodibenzoic acid (5).

$^{1}$H NMR (DMSO-d$_{6}$) δ 10.06 (br s, 1H), 9.47 (br s, 1H), 8.71 (s, 1H), 8.20 (d, 1H, J=3.2 Hz), 8.02 (d, 1H, J=8.4 Hz), 7.30 (m, 3H), 7.04 (d, 1H, J=7.2 Hz), 3.14 (m, 2H), 2.30 (t, 2H), 1.60 (m, 4H), 1.34 (m, 2H). FAB (MH$^{+}$) 378.

2-Mercapto-N-[5-(phenyl-3-ylcarbamoyl)pentyl]benzamide (201)

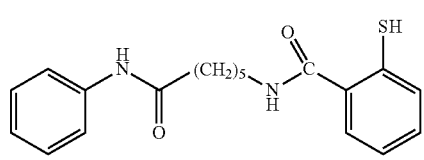

Similarly using the above methodology and starting from aniline and 6-tert-butoxy-carbonylaminohexanoic acid (2) 2-Mercapto-N-[5-(phenyl-3-ylcarbamoyl)-pentyl]-benzamide (201) was prepared. mp 110-112° C. $^{1}$H NMR (CDCl$_{3}$) δ 7.69 (br s, 1H), 7.58 (d, 2H, J=8 Hz), 7.49 (dd, 1H, J=6.3, 1.5 Hz), 7.35 (m, 4H), 7.16 (m, 2H), 6.41 (br s, 1H), 4.71 (s, 1H), 3.51 (q, 2H, J=6.6), 2.43 (t, 2H, J=7.2 Hz), 1.88-1.66 (m, 4H), 1.52 (m, 2H). EIMS (MH$^{+}$) 343.

2-Mercapto-N-[5-(4-dimethylamino-3-yl-carbamoyl)pentyl]benzamide (206)

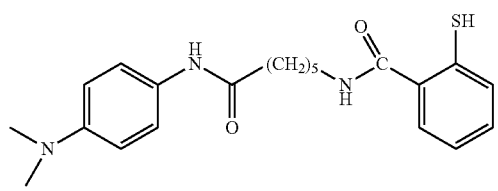

Similarly 2-Mercapto-N-(5-(4-dimethylamino-3-yl-carbamoyl)pentyl)benzamide (206), mp 108-110° C. was prepared starting from 4-dimethylamino aniline and 6-tert-butoxycarbonylaminohexanoic acid [2, $^{1}$H NMR (CDCl$_{3}$) δ 7.36 (d, 2H), 6.69 (d, 2H), 3.10 (m, 2H), 2.91 (s, 6H), 2.31 (t, 2H), 1.75 (m, 2H), 1.44 (m, 13H)] in four steps. 206: $^{1}$H NMR (DMSO-d$_{6}$) δ 9.52 (br s, 1H), 9.38 (br s, 1H), 7.37 (d, 4H J=9 Hz), 7.13 (m, 1H), 6.99 (m, 1H), 6.65 (d, 2H, J=9.00 Hz), 3.24 (m, 2H), 2.23 (t, 2H, J=7.4 Hz), 1.55 (m, 4H), 1.33 (m, 2H). FAB negative ion mode (M-H$^{+}$) 384.

2-Mercapto-N-[5-(4-Aminophenylcarbamoyl)-pentyl]benzamide (209)

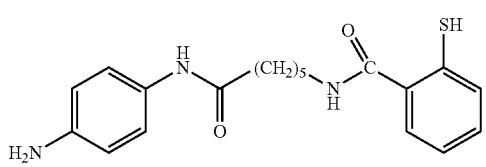

Analogously 2-Mercapto-N-[5-(4-Aminophenylcarbamoyl)-pentyl]benzamide (209) was synthesized starting from 4-nitroaniline and 6-tert-butoxycarbonylaminohexanoic acid (2). The nitro group was reduced to an amino group in step 4 during Zn/HCl reduction. NMR (DMSO-d$_{6}$) δ 9.39 (br s, 2H), 7.41 (d, 1H, J=8.00 Hz), 7.32 (d, 1H, J=8.0 Hz), 7.14 (m, 3H), 6.99 (m, 1H), 6.47 (d, 2H, J=8.7 Hz), 4.79 (s, 2H), 3.28 (m, 2H), 2.21 (t, 2H, J=7.5 Hz), 1.58 (m, 4H), 1.36 (m, 2H). ESMS (MH$^{+}$) 358.

5-Chloro-2-mercapto-N-(5-phenylcarbamoyl)-pentyl)benzamide (210)

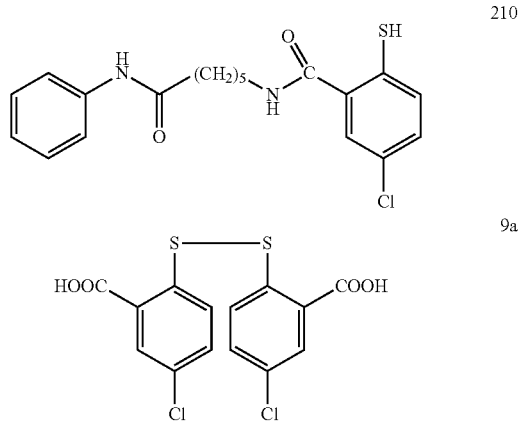

Similarly the 5-Chloro-2-mercapto-N-(5-phenylcarbamoyl)-pentyl)benzamide (210) was prepared from aniline and 6-tert-butoxycarbonylaminohexanoic acid (2). The corresponding amine in step 3 was reacted with 4,4'-dichloro-2,2'-dithiodibenzoic acid (9a) instead of 2,2'-dithiodibenzoic acid (5) to give the required product 210 in the final step.

$^{1}$H NMR (DMSO-d$_{6}$) δ 9.82 (br s, 1H), 8.56 (br s, 1H), 8.71 (s, 1H), 7.51 (m, 4H), 7.40 (m, 1H), 7.34 (m, 1H), 7.28 (m, 1H), 5.41 (br s, 1H), 3.20 (m, 2H), 2.30 (t, 2H, J=7.2 Hz), 1.61-1.50 (m, 4H), 1.35 (m, 2H). ESMS (MH$^{+}$) 377.

2-Mercapto-5-methoxy-N-(5-phenylcarbamoyl)-pentyl)benzamide (211)

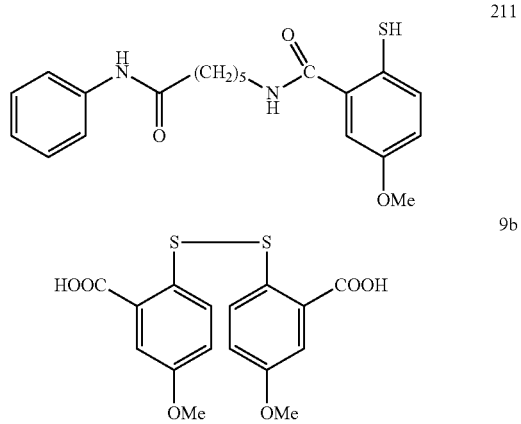

Again 2-Mercapto-5-methoxy-N-(5-phenylcarbamoyl)pentyl)benzamide (211) was prepared by treating the amine derivative in Step 3 with 4,4'-dimethoxy-2,2' dithio-dibenzoic acid (9b). $^{1}$H NMR (CDCl$_{3}$) δ 8.30 (br s, 1H), 7.53 (d, 2H, J=7.8 Hz), 7.44 (d, 1H, J=8.4°Hz), 7.24 (m, 2H), 7.08 (m, 2H), 6.87 (dd, 1H, J=3.0, 5.7 Hz), 6.49 (br s, 1H), 3.37 (q, 2H, J=6.5 Hz), 2.39 (t, 2H, J=7.5 Hz), 1.75 (m, 2H), 1.56 (m, 2H), 1.46 (m, 2H). ESMS (M H⁺) 373.

2-Mercapto-N-(6-phenylcarbamoyl-hexyl)benzamine (212)

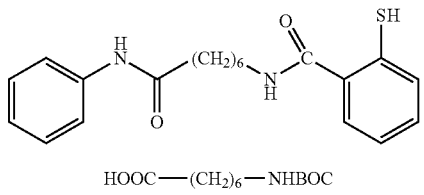

HOOC—(CH₂)₆—NHBOC  16

Similarly the 2-Mercapto-N-(6-phenylcarbamoyl-hexyl)benzamide (212) was synthesized starting from aniline and 7-tert-butoxycarbonylaminoheptanoic acid (16) instead of 6-tert-butoxycarbonylaminohexanoic acid (2) in step 1. ¹H NMR (DMSO-d₆) δ 9.82 (br s, 1H), 8.38 (br s, 1H), 7.56 (d, 2H, J=7.8 Hz), 7.41 (m, 2H), 7.26 (m, 3H), 7.25 (m, 1H), 6.99 (t, 1H, J=7.5 Hz), 5.34 (br s, 1H), 3.20 (m, 2H), 2.29 (t, 2H, J=7.2 Hz), 1.61-1.48 (m, 4H), 1.34 (m, 2H). m/e 356.

2-Mercapto-N-7-phenylcarbamoyl-heptyl)benzamide (213)

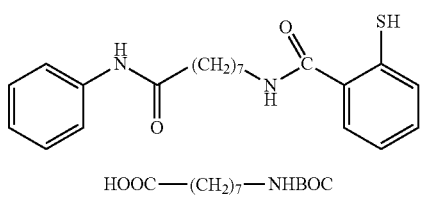

HOOC—(CH₂)₇—NHBOC  18

2-Mercapto-N-7-phenylcarbamoyl-heptyl)benzamide (213) was prepared starting from aniline and 8-tert-butoxycarbonylaminooctanoic acid (18) in place of 6-tert-butoxycarbonylaminohexanoic acid (2) in Step 1. ¹H NMR (DMSO-d₆) δ 9.82 (br s, 1H), 8.38 (br s, 1H), 7.57 (d, 2H, J=7.5 Hz), 7.40 (m, 2H), 7.25 (m, 3H), 7.15 (m, 1H), 6.99 (t, 1H, J=7.2 Hz), 5.34 (br s, 1H), 3.20 (m, 2H), 2.28 (t, 2H, J=7.2 Hz), 1.60-1.49 (m, 4H), 1.31 (m, 2H). m/e 370.

2-Mercapto-N-(10-phenylcarbamoyl-decyl)benzamide (214)

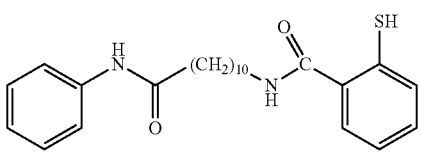

HOOC—(CH₂)₁₀—NHBOC  20

Finally the 2-Mercapto-N-(10-phenylcarbamoyl-decyl)benzamide (214) was made from aniline and 11-tert-butoxycarbonylaminoundecanoic acid (20) in Step 1 instead of 6-tert-butoxy-carbonylaminohexanoic acid (2) as previous. ¹H NMR (DMSO-d₆) δ 9.82 (br s, 1H), 8.37 (br s, 1H), 7.57 (d, 2H, J=8.00 Hz), 7.41 (m, 2H), 7.24 (m, 3H), 7.17 (m, 1H), 6.99 (t, 1H, J=7.5 Hz), 5.34 (br s, 1H), 3.20 (m, 2H), 2.27 (t, 2H, J=7.5 Hz), 1.56 (m, 2H), 1.48 (m, 2H), 1.34 (m, 2H). m/e 412.

TABLE 1

HDAC Inhibitor Compounds

| Compound | Structure |
|---|---|
| 201 | 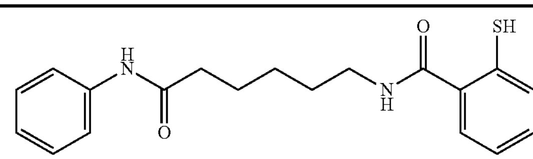 |
| 203 | 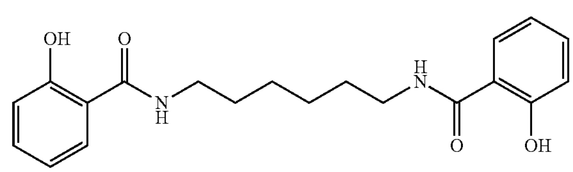 [SMILES: O=C(NCCCCCCNC(=O)c1ccccc1O)c1ccccc1O] |
| 204 | 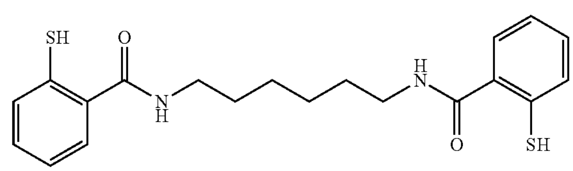 |
| 205 | 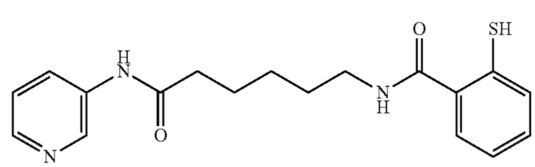 [SMILES: O=C(CCCCCNC(=O)c1ccccc1S)Nc1cccnc1] |

TABLE 1-continued
HDAC Inhibitor Compounds
| Compound | Structure |
|---|---|
| 206 | 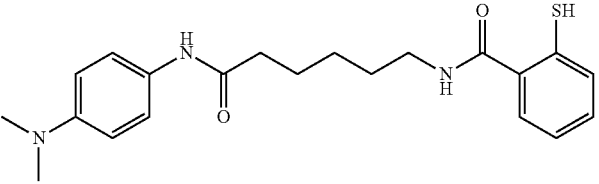 [SMILES: CN(C)c1ccc(NC(=O)CCCCCNC(=O)c2ccccc2S)cc1] |
| 207 | 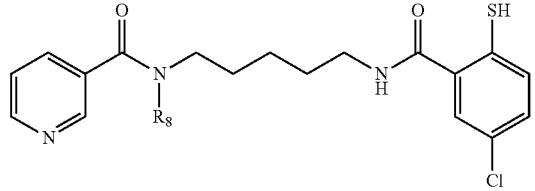<br>wherein R₈ is H, alkyl, or aryl. |
| 207a | 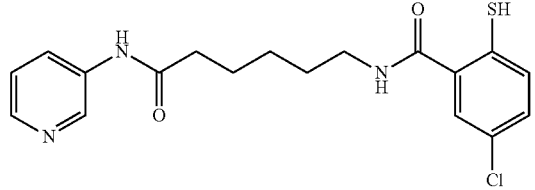 [SMILES: O=C(CCCCCNC(=O)c1cc(Cl)ccc1S)Nc1cccnc1] |
| 208 | 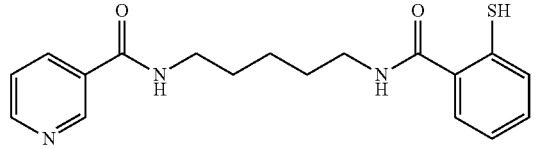 [SMILES: O=C(NCCCCCNC(=O)c1ccccc1S)c1cccnc1] |
| 209 | 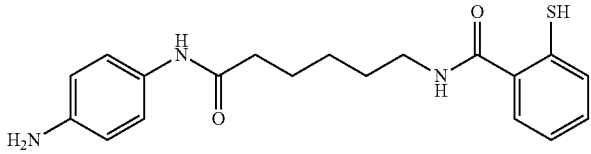 [SMILES: Nc1ccc(NC(=O)CCCCCNC(=O)c2ccccc2S)cc1] |
| 210 | 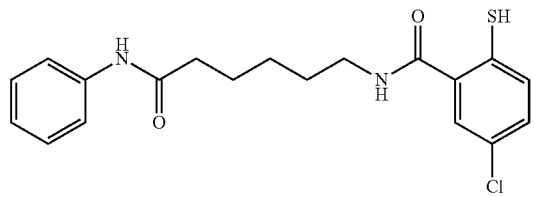 [SMILES: O=C(CCCCCNC(=O)c1cc(Cl)ccc1S)Nc1ccccc1] |
| 211 | 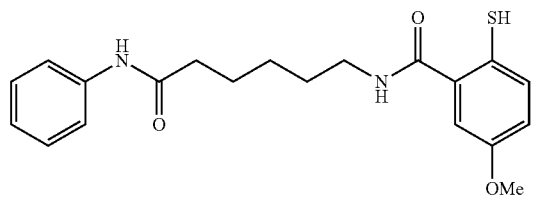 [SMILES: COc1ccc(S)c(C(=O)NCCCCCC(=O)Nc2ccccc2)c1] |
| 212 | 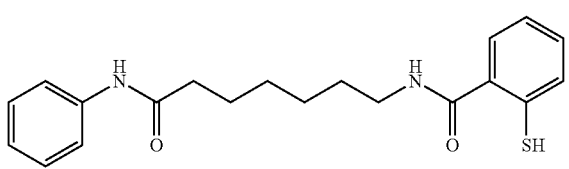 [SMILES: O=C(CCCCCCNC(=O)c1ccccc1S)Nc1ccccc1] |

TABLE 1-continued

HDAC Inhibitor Compounds

| Compound | Structure |
|---|---|
| 213 | 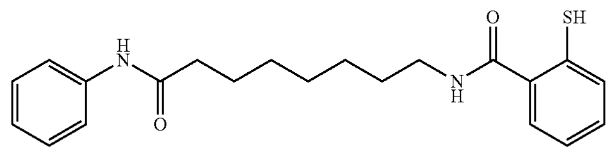 [SMILES: O=C(CCCCCCCNC(=O)c1ccccc1S)Nc1ccccc1] |
| 214 | 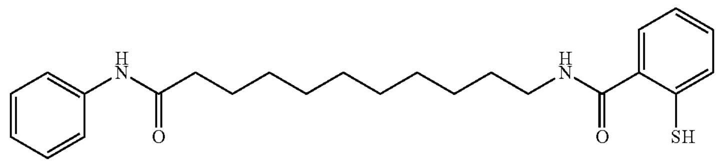 [SMILES: O=C(CCCCCCCCCCNC(=O)c1ccccc1S)Nc1ccccc1] |

Materials and Methods

MDA-MB-231, HT-29, NCI-H460, NCI-H522, NCI-H69, GXF-209, HepG2, OVAR-3, PANC-1, DU-145, LNCAP, HL-60, K-562, and MOLT-4 cell lines were either obtained from the American Type Culture Collection (ATCC; Manassas, Va.), or from the National Cancer Institute (NCI; Frederick, Md.). RPM-1640 media, L-glutamine dipeptide (HyQ SG-200), and HEPES were obtained from Hyclone (Logan, Utah). Fetal bovine serum (FBS) was obtained from Sigma-Aldrich, (St. Louis, Mo.). DMSO was purchases from Fisher Chemicals (Fair Lawn, N.J.). The CellTiter-Glo Luminescent Cell Viability Assay reagent was obtained from Promega Corporation (Madison, Wis.). All tissue culture plasticware was obtained from Corning Incorporated (New York, N.Y.). Compound 100 and Compound 102 were provided by Lixte Biotechnology Holdings, Inc. (East Setauket, N.Y.).

All cell lines were routinely cultured twice weekly in RPMI-1640 medium supplemented with 2 mM L-glutamine dipeptide, 10 mM HEPES, and 10% FBS.

The adherent cell lines MDA-MB-231, HT-29, NCI-H460, NCI-H522, GXF-209, HepG2, OVAR-3, PANC-1, DU-145, and LNCAP cells were each seeded into two 96-well plates at 2,500 cells per well in a total volume of 50 uL and incubated in a 37 C humidified 5% CO2 cell culture incubator overnight. The suspension cell lines NCI-H69, HL-60, K-562, and MOLT-4 were each seeded into two 96-well plates at 10,000 cell per well in a total volume of 50 uL and incubated in a 37 C humidified 5% CO2 incubator overnight.

A 20 mM stock of Compound 205 were made in DMSO. This was followed by making 2× stocks of the final concentrations required in RPM-1640 medium. 50 uL of the 2× stock solutions were added to the appropriate wells, which contained 50 uL of cells and medium to give the final concentrations outlined in the Appendix. 50 uL of media were added to media and cell control wells and 50 uL of a mock 2% DMSO stock solution were added to vehicle control wells. At the same time that the drugs were added to the cells, one of the plates from each cell line was used for the CellTiter-Glo assay as described below in order to obtain Day 0 values for each cell line. Following a 72 hr incubation period, the CellTiter-Glo assay was performed on the remaining plate.

CellTiter-Glo Assay

The assay was performed as per the manufacturer's instructions. Briefly, plates were removed from the incubator and placed on the bench at room temperatures for 30 minutes. Plates were not stacked. Following the 30 min incubation at room temperature, 100 uL of CellTiter-Glo reagent were added to each well on the plate and mixed for 2 minutes, followed by further 10 minute incubation at room temperature. Luminescence was then recorded using the PerkinElmer Microbeta scintillation and luminescence counter (Trilux).

Results and Discussion

These studies were performed as describes in Materials and Methods, with the raw data and plate set-up outlined in the Appendix. The IC50 values for compound 205 in each cell line are outlined in Table 2. The graphical representation of the effect of the compounds on each cell line, along with the associated curve fits, is illustrated in FIGS. 8A-N.

The majority of cell lines tested were sensitive to compound 205 in the low uM range (Table 2). against cell lines of: breast cancer; colon cancer; two major types of lung cancer, adenocarcinoma and small cell (large cell carcinoma was the least sensitive); stomach cancer; liver cancer (hepatoma); ovary adenocarcinoma; pancreas carcinoma, two types of prostate carcinoma; and three types of leukemia, promylocytic, chronic myelocytic, and acute lypmphocytic (Table 2). Compound 205 was most active against lung adenocarcinoma, stomach cancer, pancreatic cancer, and breast cancer.

TABLE 2

The Inhibitory Concentration of Compound 205 that Results in 50% Inhibition of the Proliferation of Human Cell Lines in vitro.

| Human Cancer Cell Line | Compound 205 $IC_{50}$ (uM) |
|---|---|
| MDA-MB-231 Breast | 24.8 |
| HT-29 Colon | 47.6 |
| NCI-H460 Lung large cell | >100 |
| NCI-H522 Lung adenoca | 1.8 |
| NCI-H69 Lung small cell | 16.1 |
| GXF-209 Stomach | 22 |
| HepG2 Hepatoma | 53.1 |
| OVCAR-3 Ovary adenoca | 18.7 |
| PANC-1 Pancreas | 11.9 |
| DU-145 Prostate | 50.2 |
| LNCAP Prostate | 6.2 |
| HL-60 Leukemia promyelocytic | 60* |
| K562 Leukemia chronic myelo | 58.3 |
| MOLT-4 Leukemia acute lympho | 26.3 |

*Denotes that $IC_{50}$ value was estimated from the data as no curve fit was possible.

Example 1

To identify novel therapeutic targets for the treatment of glioblastoma multiforme (GBM), the compounds of the subject invention were evaluated for their ability to inhibit glioblastoma multiforme cells in vitro and in vivo.

Figure 6:
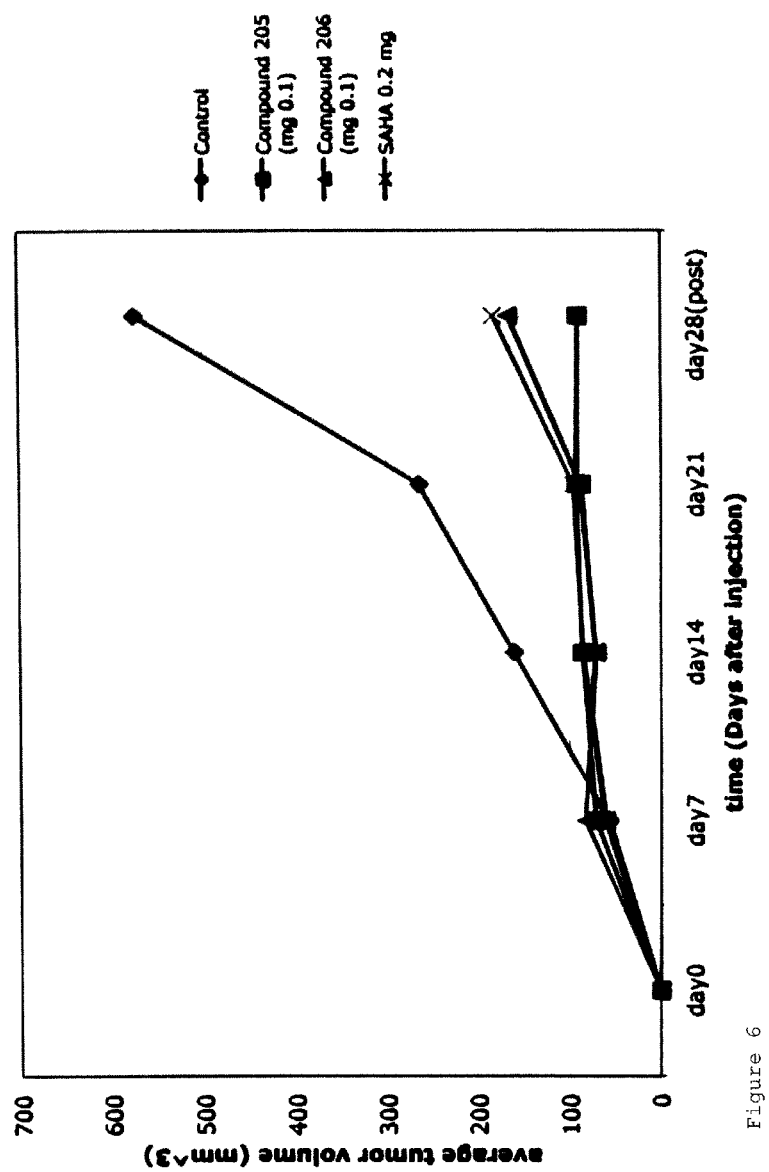
FIG. 6: Inhibition of compound 205, compound 206, or SAHA on GBM xenograft tumor volume measured at 0, 7, 14, 21 and 28 days.

Each of the compounds inhibited the growth of GBMs in a dose dependent manner in vivo as shown in FIGS. 1-5 and 16-22. Compounds 205 and 206 each inhibited the growth of GBM xenograft tumor volume in SCID mice as shown in FIG. 6.

From graphic plots of, the GBM cell line U373 as a function of exposure to different doses of drug for 7 days, the proportion relative to the control was measured and plotted graphically.

Figure 9:
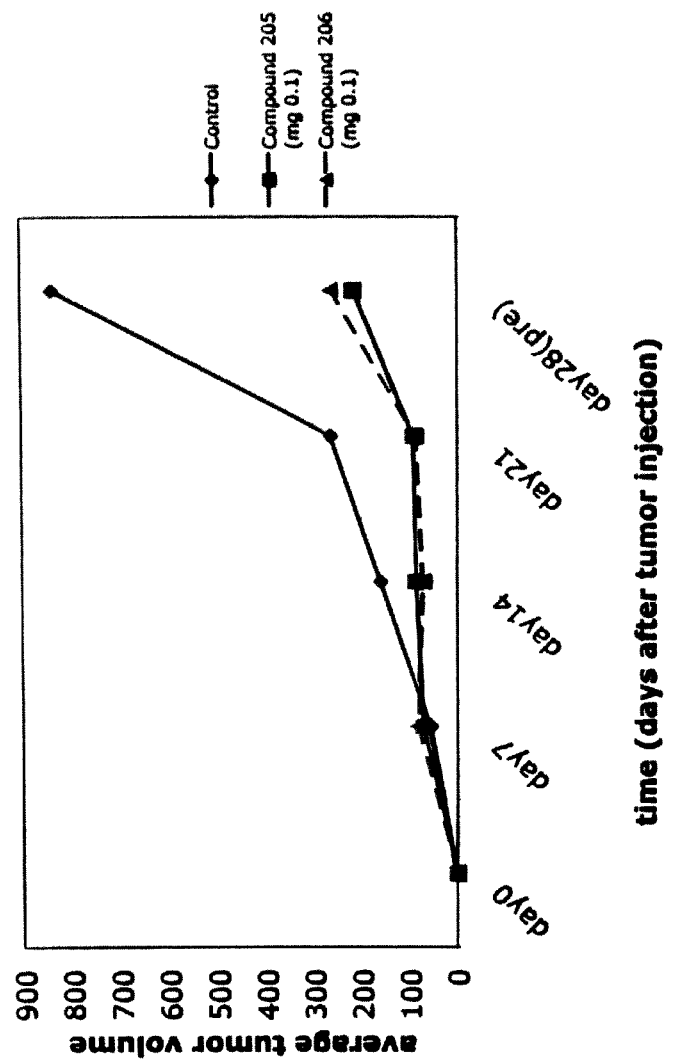
FIG. 9: Compound 205 and 206 Inhibition of 087 GBM Xenograft

All of the compounds are active against the cell line U-87, however compounds 201, 205, 206, 212, and 213 are the most potent on an equimolar basis. Both compounds 205 and 206 show significant inhibition of U87 GBM xenografts compared to control (FIG. 9).

Figure 7:
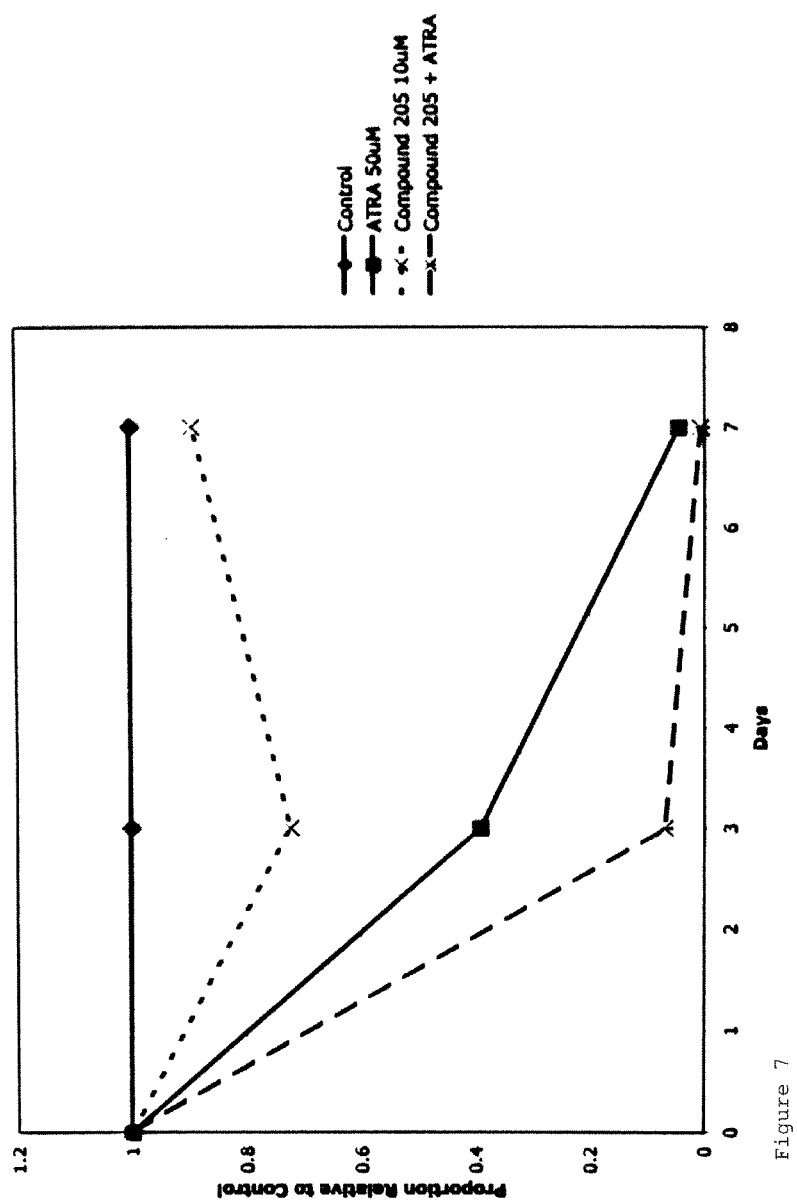
FIG. 7: Inhibition of growth of medulloblastoma cell line DAOY by compound 205 or compound 205 in combination with ATRA measured at 1, 3 and 7 days.
Figure 11:
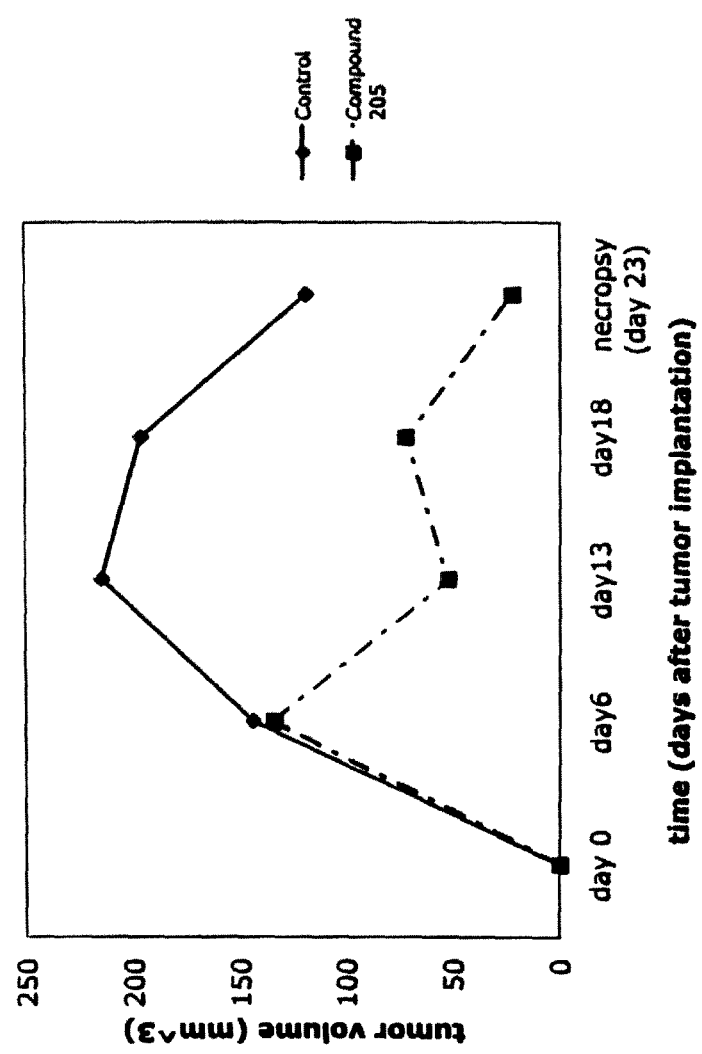
FIG. 11: Compound 205 Inhibition of DAOY Xenograft
Figure 12:
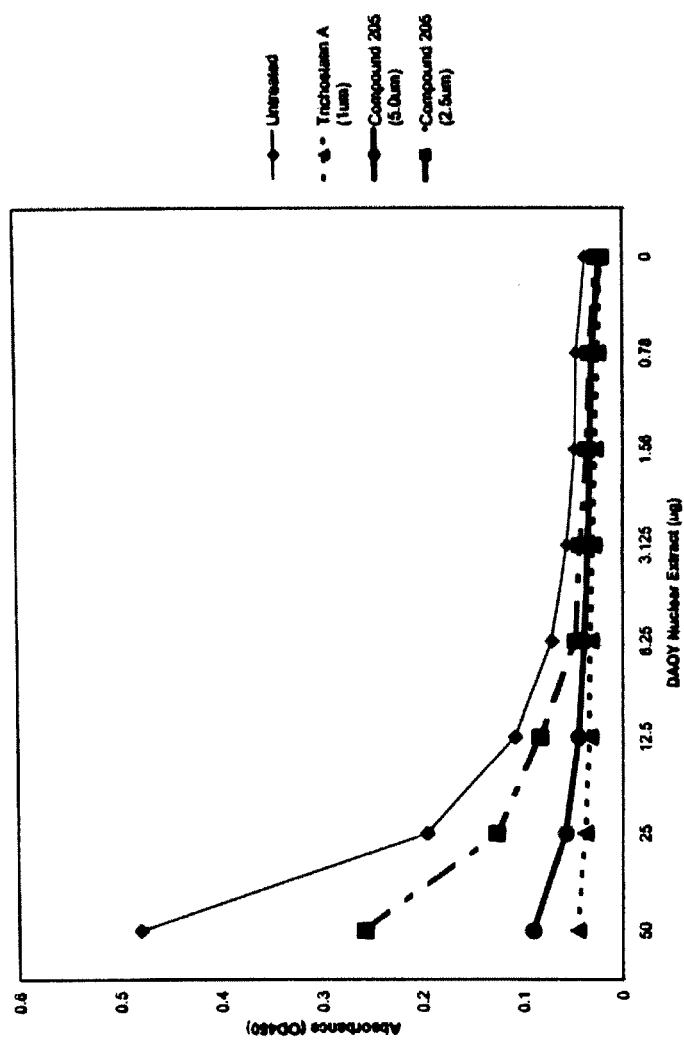
FIG. 12: Compound 205 and Trichostatin Inhibition of HDAC Activity in DAOY Cells
Figure 13:
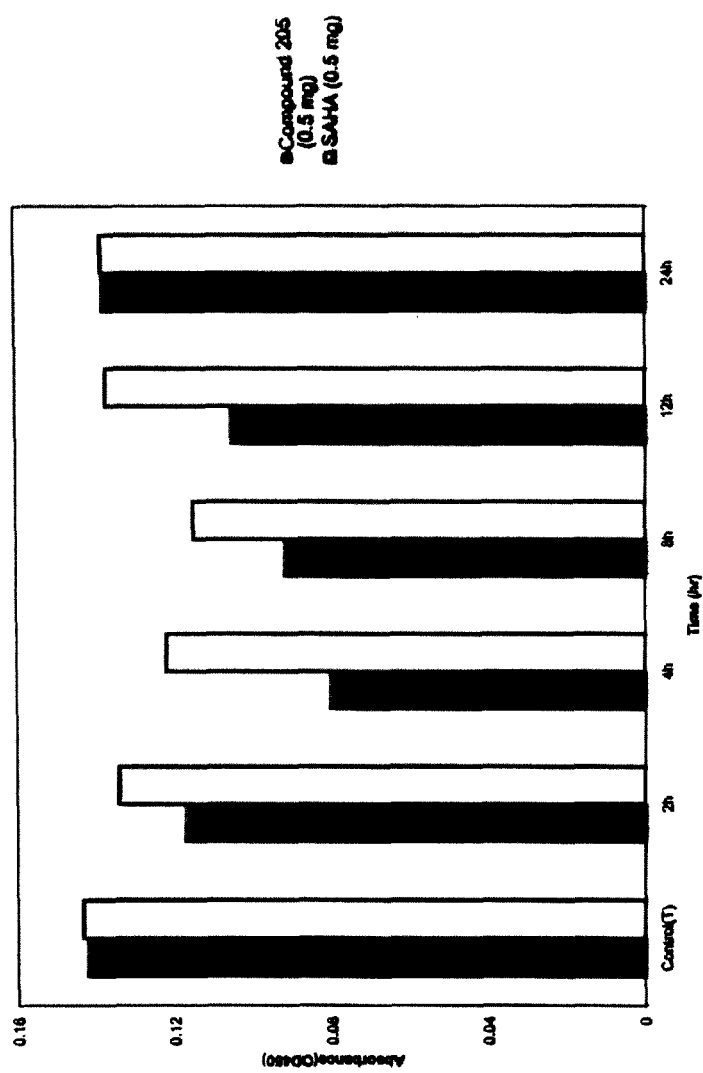
FIG. 13: Compound 205 and SAHA Inhibition of HDAC Activity in DAOY Xenografts

We have shown that compound 205 is active against medulloblastoma cell line DAOY (FIGS. 11-13). We have also shown the compound 205 in combination with ATRA is active against medulloblastoma cell line DAOY (FIG. 7).

Figure 10:
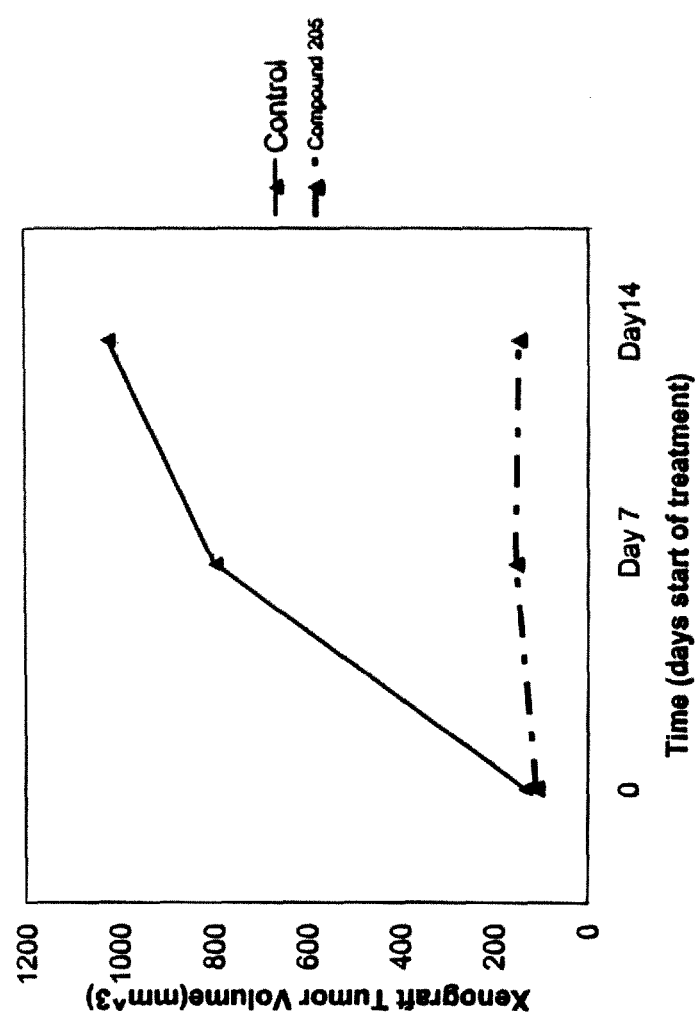
FIG. 10: Compound 205 Inhibition of SHSY-5Y Xenograft
Figure 14:
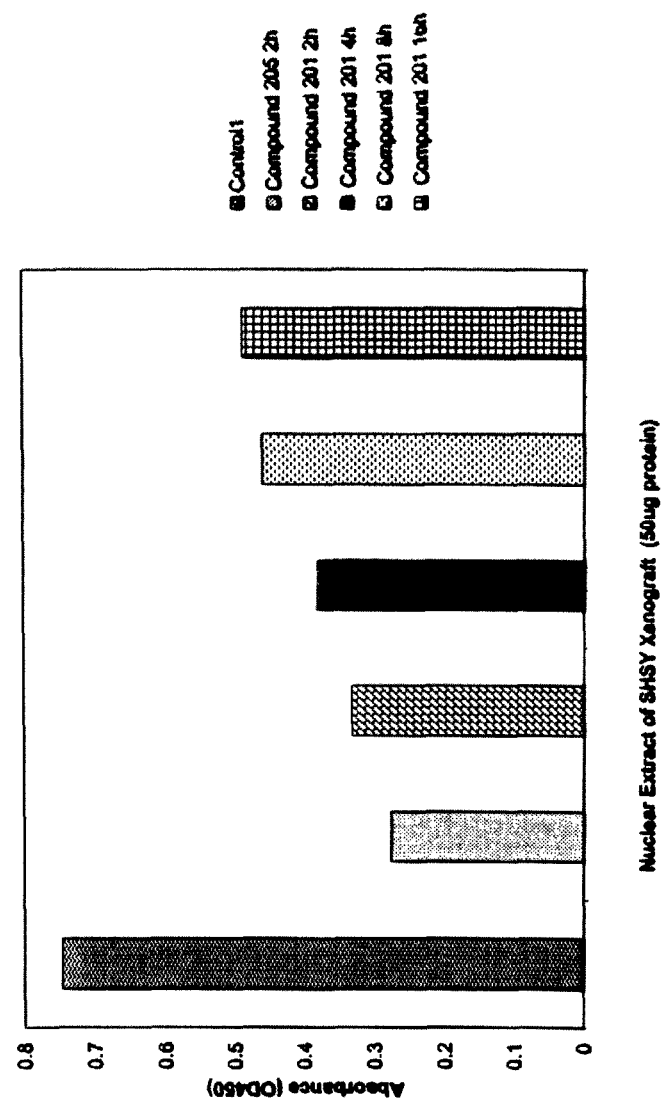
FIG. 14: Compound 201 and 205 Inhibition of HDAC Activity in SHSY-5Y Xenografts
Figure 15:
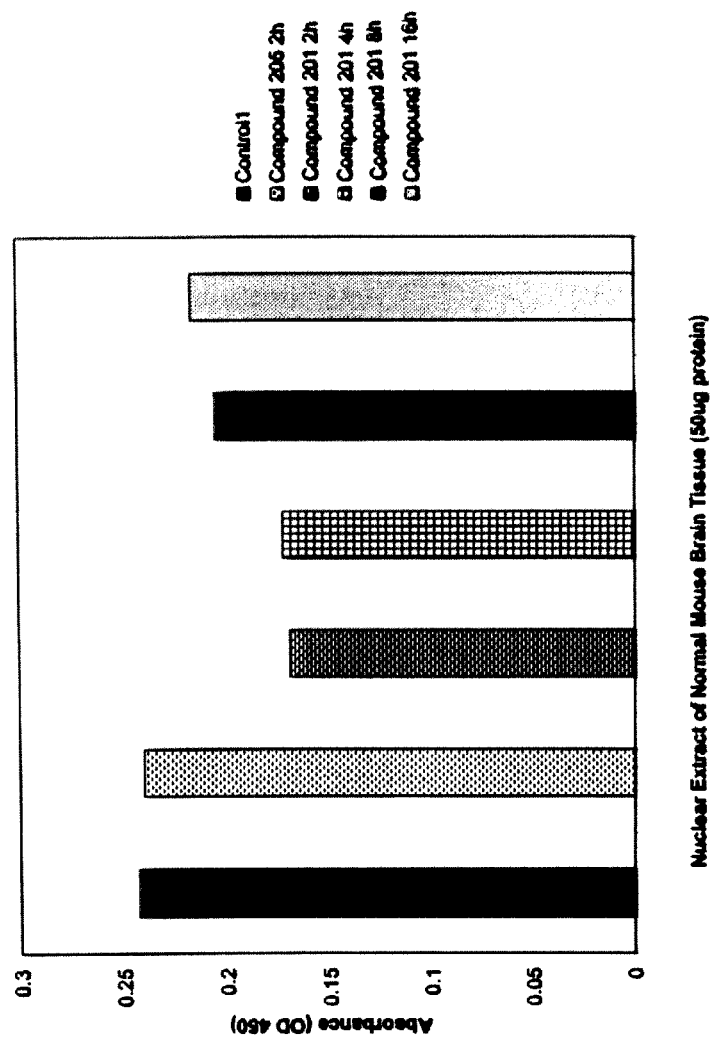
FIG. 15: Compound 201 and 205 in Normal Mouse Brain Tissue
Figure 16:
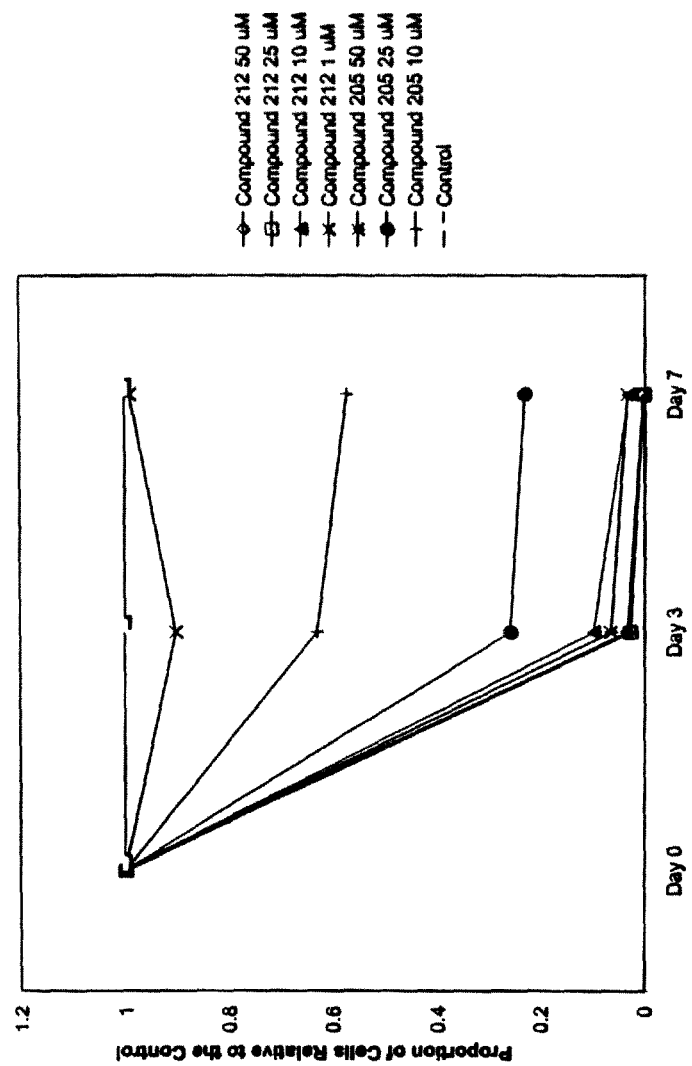
FIG. 16: Compound 205 and 212 against Glioblastoma Multiforme (U373)
Figure 17:
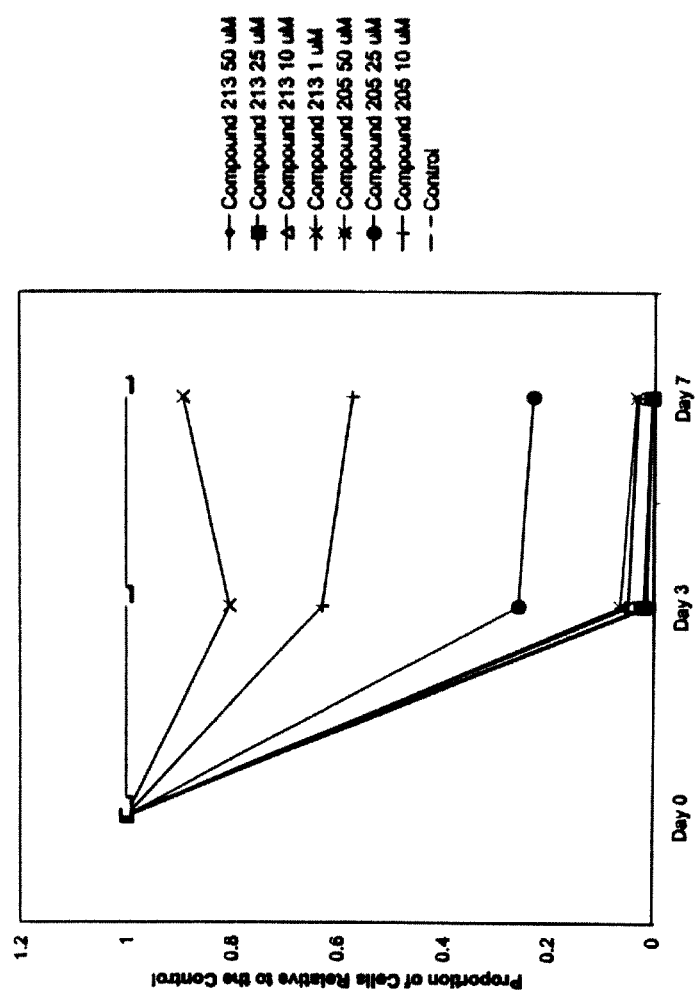
FIG. 17: Compound 205 and 213 against Glioblastoma Multiforme (U373)
Figure 18:
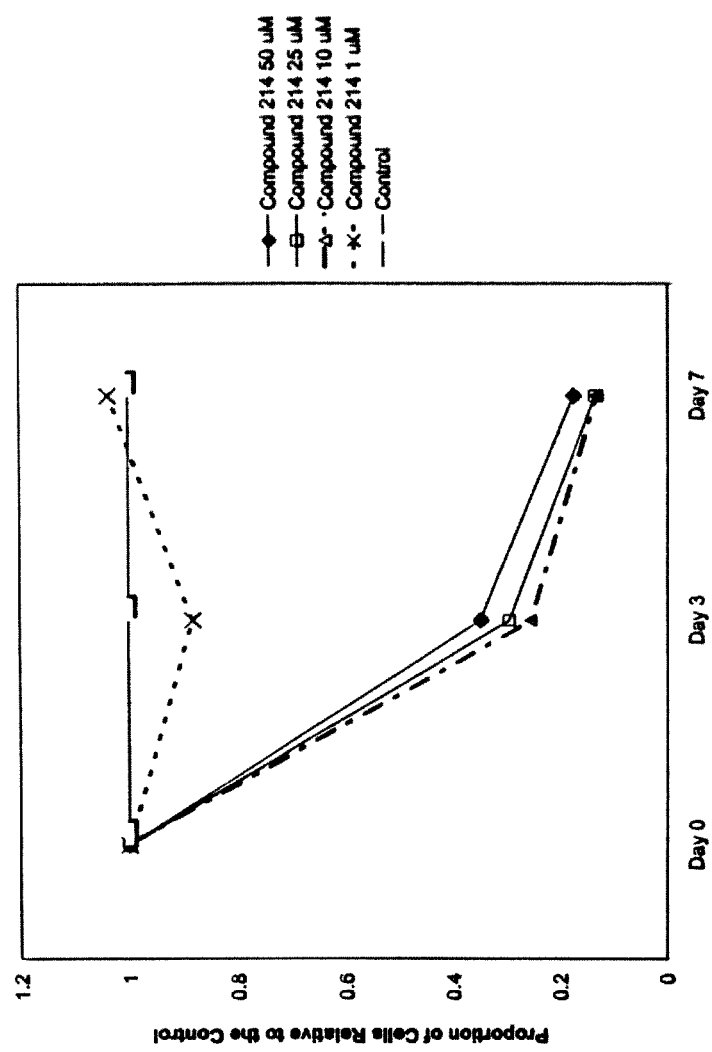
FIG. 18: Compound 214 against Glioblastoma Multiforme Line 0373
Figure 19:
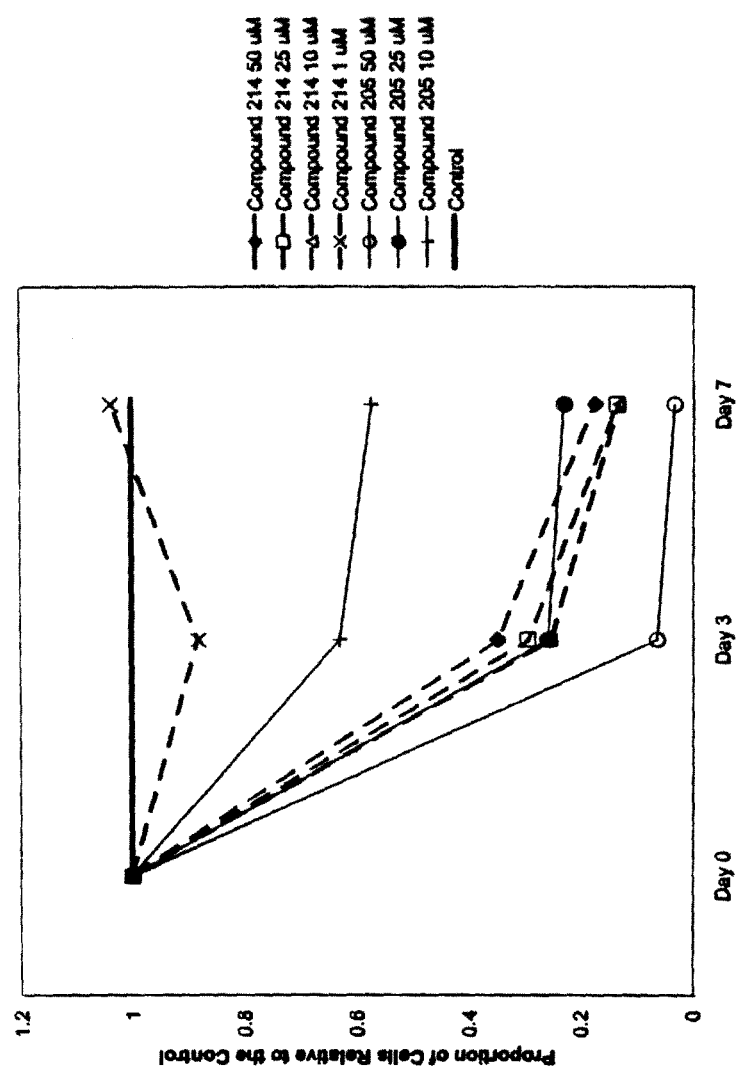
FIG. 19: Compound 205 and 214 against Glioblastoma Multiforme (U373)
Figure 20:
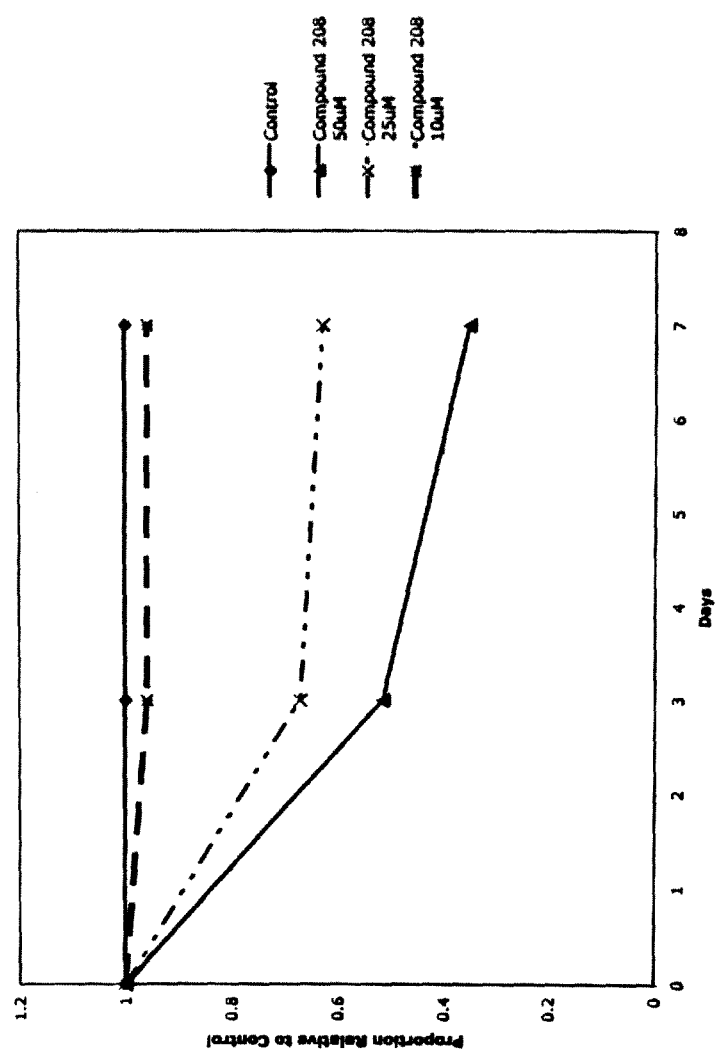
FIG. 20: Compound 208 against Glioblastoma Multiforme: Line U373
Figure 21:
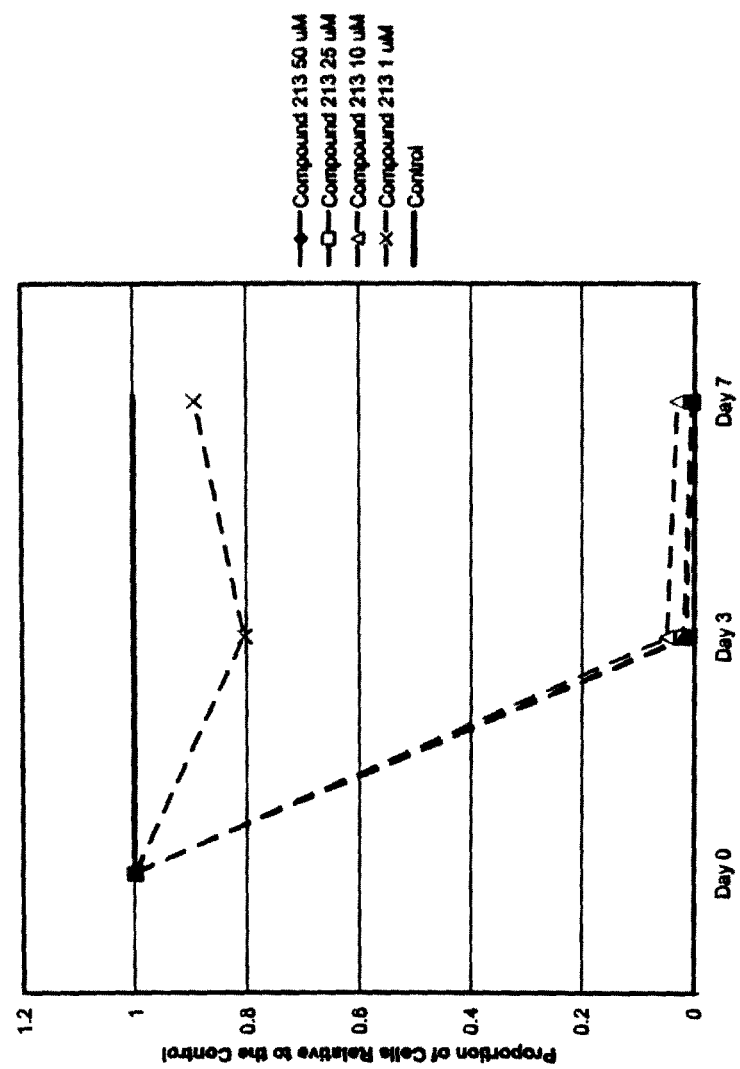
FIG. 21: Compound 213 against Glioblastoma Multiforme U373
Figure 22:
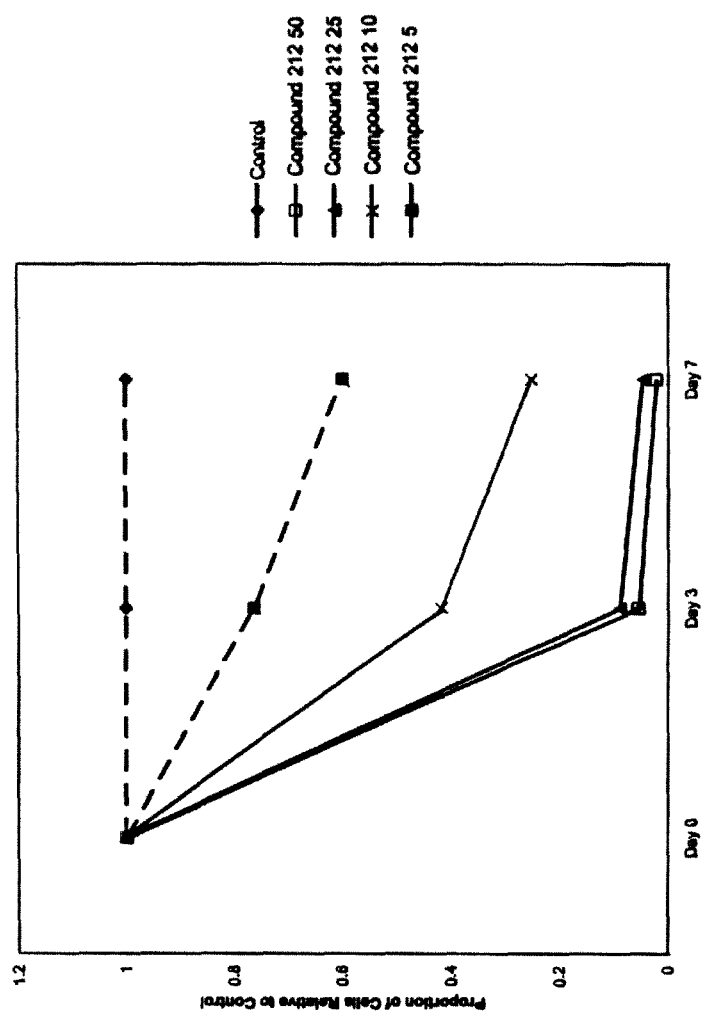
FIG. 22: Compound 212 versus Glioblastoma Multiforme Line U373

Compound 205 shows activity against the growth of SHSY-5Y xenografts (FIGS. 10 and 14) while not inhibiting normal cell growth, as evidenced by high viability of normal mouse brain cells compared to control (FIG. 15).

We have also shown that compound 205 is active against multiple human cancer cell lines at low micromolar concentrations. These cancers include those of the breast, colon, lung (3 types), stomach, liver (hepatoma), ovary, pancreas and prostrate and three types of leukemia, promyeloctyic, chromic myelocytic, and acute lymphocytic (Table 2, FIGS. 8A-N).

We have also found that compound 205 is active in an in vivo mouse model of human glioblastome multiforme (GBM) when the tumor cells are implanted subcutaneously in SCID mice. In addition, we found that in this case compound 205 is more active than, an equimolar dose of SAHA.

Therefore, based on the anti-cancer activity of the compounds of this invention, it is also contemplated that given the structure of these compounds, they will be active as anti-HIV agents targeting Zn functional groups in retroviral zinc finger domains.

Example 2

New antimycotics continue to reach the market, many with the promise of increased activity over those agents that are currently available.

A total of 23 isolates were tested to include 3 *Candida albicans*, 3 *Candida glabrata*, 3 *Cryptococcus neoformans*, 3 *Aspergillus fumigatus*, 3 *Rhizopus oryzae*, 3, *Fusarium solani*, 3 *Pseudallescheria boydii*, and 2 *Trichosporon rubrum*. All isolates were clinical isolates submitted to the Fungus Testing Laboratory for evaluation. Antifungal susceptibility testing was accomplished according to the methods outlined in the National Committee for Clinical Laboratory Standards, M-27A2, Reference Method for Broth Dilution Antifungal Susceptibility Testing of Yeasts; Approved Standard, and M38-A "Reference Method for Broth Dilution Antifungal Susceptibility Testing of Conidium-Forming Filamentous Fungi; Approved Standard". This includes testing in RPMI-1640 with glutamine and without bicarbonate, an inoculum size of 0.5-2.5×$10^3$ for yeasts or 1-5×$10^0$ for moulds, and incubation at 35° C. for 24 and 48 hours. The minimum inhibitory concentration (MIC) was defined as the lowest concentration that resulted in a 50% reduction in turbidity as compared to a drug-free control tube for the yeast and 80% inhibition for the moulds. Drug concentrations were 0.125-64 µg/ml.

Endpoints were determined for most species when testing the compounds.

Introduction

The growing population of immunocompromised patients due to transplantation, HIV/AIDS and cancer, primarily leukemia, has resulted in an increase in severe fungal infections. The fungi most often recovered from infections in these patients are *Aspergillus* spp. and *Candida* spp. Effective therapies are available for the treatment of *Candida* spp. but there remains a concern about the treatment of infections caused by *Aspergillus* spp., which are associated with high mortality in the immunocompromised host. Such infections are difficult to clear in this group of patients thus increasing the need for agents with good activity against these fungi. As a result of the changing scene of fungal infections and the lack of an overall cure for these infections, the compounds of this invention are proposed as potential anti-fungal agents.

Materials and Methods

Testing was completed with a common lot for each agent.

A 10 mg portion of each powder was weighed out and added to 1 ml of 100% DMSO for compound 205. The resulting concentration of 10 µg/ml was diluted to a working concentration of 6400 µg/ml for compound 205 in 100% DMSO. All subsequent dilutions were also made using the respective diluents. Final testing concentrations ranged from 0.125-64 µg/ml.

The NCCLS recommended medium RPMI-1640 (Hardy Diagnostics, Santa Monica, Calif.) was utilized as the test medium.

All isolates in this study were clinical isolates received in the Fungus Testing Laboratory for standard antifungal susceptibility testing and/or identification. Isolates, which were not sent for identification, were confirmed to assure testing integrity. A total of 23 were tested to include 3 *Candida albicans*, 3 *Candida glabrata*, 3 *Cryptococcus neoformans*, 3 *Aspergillus fumigatus*, 3 *Rhizopus oryzae*, 3, *Fusarium solani*, 3 *Pseudallescheria boydii*, and 2 *Trichosporon rubrum*.

Minimum inhibitory concentrations (MIC) were determined at the first 24-hour interval where growth could be determined in the drug-free control tube. The defined MIC yeast was the lowest concentration that exhibited an 50% reduction in turbidity as compared to the growth control while the MIC for moulds was determined where 80% reduction was noted.

Discussion

We have developed a new class of histone deacetylase inhibitors. Their novelty resides on the use of a 2-mercapto-N-benzoylamino group linked to a substituted or unsubstituted 5-phenyl-3-ylcarbamoyl terminal group or a 5-pyridin-3-ylcarbamoyl group separated by 5 to 10 methylene groups. The novelty of these compounds resides in the use of the mercaptobenzoylamino group for zinc chelation. We show that this class of HDAC inhibitors is active against a wide spectrum of human cancer cells growing in culture and growing as xenografts in immunosupressed mice. We demonstrate further that this group of HDAC inhibitors inhibits both class I (histone 3) and class II (histone 4) histone deacetylases. We show that compounds of this type inhibit HDAC in xenografts growing in nude mice and inhibit HDAC activity in normal brain tissue of mice when given systemically. Thus, compounds of this type inhibit their intended target in vivo and reach normal brain tissue at doses of drug which result in no discernable toxicity to mice yet cause marked inhibition of tumor growth.

An important advantage of this group of drugs is that they may be readily derivatized on both the mercaptobenzamoyl moiety and the opposite end of the molecule, which may be any of many structures including the examples shown consisting of substituted and unsubstituted pyridinyl and phenyl moieties and a novel symmetrical molecule with two mercaptobenzoylamino moieties (bis-1,6-(mercaptobenzoylamino) hexane (compound 204).

Another potential advantage to this group of drugs is that HDAC inhibitors operate by a mechanism apart from all standard anti-cancer drugs. It is likely that the HDACs can be combined with other drugs to achieve enhanced anti-cancer activity without increased toxicity. We provide one example that shows that the combination of all-trans retinoic acid with compound 205 has greater than additive activity in inhibiting the growth of neuroblastoma cells (FIG. 7).

CONCLUSION

The results for the compounds are shown in Table 2. The compounds of this invention do possess endpoints. Depending on achievable levels of these compounds in human subjects, safety profiles and other pertinent factors to consider in moving forward to development, these compounds may be viable contenders as anti-fungal agents on human and plant infections as we demonstrate that members of this class of HDAC inhibitors have significant anti-proliferative activities against medically important pathogenic fungi (summarized in Tables 3 and 4).

In addition, because members of this group of compounds crosses the blood brain barrier and inhibits HDAC activity in normal brain, and because there are many reports that such neural activity has beneficial effects on several models of neurodegenerative diseases, we believe these compounds will be useful as neuroprotective agents, with potential utility for treating chronic neurodegenerative diseases of unknown origin such as the tauopathies and traumatic brain injury.

Furthermore, compounds of this class are expected to be useful for the treatment of chronic and potentially acute inflammatory diseases including those associated with fibrosis, such as cardiac hypertrophy and rheumatoid arthritis.

TABLE 3

Antifungal Activity of compounds 201, 204, 205, 206, and 207

| | | Compound 201 24 | Compound 201 48 | Compound 204 24 | Compound 204 48 | Compound 206 24 | Compound 206 48 | Compound 205 24 | Compound 205 48 | Compound 207 24 | Compound 207 48 |
|---|---|---|---|---|---|---|---|---|---|---|---|
| CP | Control | 8 | >64 | 8 | >64 | 8 | 64 | 32 | 32 | 16 | 16 |
| 07-3006 | C. albicans | 8 | >64 | >64 | >64 | 64 | >64 | 32 | 64 | >64 | >64 |
| 07-3011 | C. albicans | 4 | >64 | >64 | >64 | 64 | >64 | 32 | >64 | >64 | >64 |
| 07-3012 | C. albicans | 4 | >64 | >64 | >64 | >64 | >64 | 32 | 64 | >64 | >64 |
| 07-2964 | C. glabrata | 2 | >64 | >64 | >64 | 32 | >64 | 32 | 64 | >64 | >64 |
| 07-2965 | C. glabrata | 1 | >64 | >64 | >64 | 32 | >64 | 32 | 64 | >64 | >64 |
| 07-3013 | C. glabrata | 2 | >64 | >64 | >64 | 32 | >64 | 32 | 64 | >64 | >64 |
| 07-2665 | C. neoformans | 2 | >64 | 4 | 4 | 16 | 32 | 32 | 32 | 16 | 32 |
| 07-2737 | C. neoformans | 2 | 4 | >64 | >64 | 16 | 32 | 32 | 32 | 32 | >64 |
| 07-2829 | C. neoformans | 2 | 2 | >64 | >64 | 64 | 64 | 32 | 32 | >64 | >64 |
| 07-1870 | R. arrhizus | 4 | 4 | >64 | >64 | 32 | 64 | >64 | >64 | >64 | >64 |
| 07-2044 | R. arrhizus | 8 | >64 | >64 | >64 | 32 | 64 | 64 | 64 | >64 | >64 |
| 07-2078 | R. arrhizus | >64 | >64 | >64 | >64 | >64 | >64 | 64 | >64 | >64 | >64 |
| 07-1399 | F. solani | 16 | >64 | >64 | >64 | >64 | >64 | 64 | >64 | >64 | >64 |
| 07-1755 | F. solani | 16 | >64 | >64 | >64 | >64 | >64 | >64 | >64 | >64 | >64 |
| 07-1867 | F. solani | 16 | >64 | >64 | >64 | 64 | >64 | 32 | 64 | >64 | >64 |
| 07-1333 | S. apiospermum | 1 | 1 | 0.5 | 1 | 1 | 2 | 8 | 16 | 0.5 | 1 |
| 07-1502 | S. apiospermum | 2 | 4 | 2 | 2 | 8 | 16 | 32 | 64 | 16 | 32 |
| 07-1601 | S. apiospermum | 0.25 | 0.25 | <0.125 | 0.5 | 2 | 2 | 2 | 4 | 4 | 4 |
| 05-388 | A. fumigatus | 1 | >64 | 2 | >64 | 16 | >64 | 16 | >64 | 16 | >64 |
| 06-4126 | A. fumigatus | 0.5 | 8 | 1 | >64 | 8 | 64 | 16 | >64 | 16 | >64 |
| 07-2039 | A. fumigatus | 1 | >64 | 1 | >64 | 8 | >64 | 8 | >64 | >64 | >64 |
| 07-1743 | T. rubrum | 2 | 2 | 1 | 1 | 0.25 | 0.25 | 16 | 32 | 0.25 | 0.25 |
| 07-2055 | T. rubrum | 2 | 2 | 1 | 1 | 0.25 | 0.25 | 8 | 16 | 0.25 | 0.25 |

TABLE 4

Antifungal Activity of Compounds 201, 209, 210, and 211.

| | | Compound 201 24 | Compound 201 48 | Compound 209 24 | Compound 209 48 | Compound 210 24 | Compound 210 48 | Compound 211 24 | Compound 211 48 |
|---|---|---|---|---|---|---|---|---|---|
| 07-3006 | C. albicans | 4 | >64 | 2 | 32 | >64 | >64 | >64 | >64 |
| 07-3011 | C. albicans | 8 | >64 | 2 | 32 | >64 | >64 | >64 | >64 |
| 07-3012 | C. albicans | 8 | >64 | 2 | 32 | >64 | >64 | >64 | >64 |
| 07-2964 | C. glabrata | 4 | >64 | 2 | 32 | >64 | >64 | >64 | >64 |
| 07-2965 | C. glabrata | 2 | >64 | 2 | 32 | >64 | >64 | >64 | >64 |
| 07-3013 | C. glabrata | 2 | >64 | 2 | 32 | >64 | >64 | >64 | >64 |
| 07-2665 | C. neoformans | 2 | 2 | 32 | 32 | >64 | >64 | 8 | 16 |
| 07-2737 | C. neoformans | 2 | 4 | 8 | 16 | >64 | >64 | 8 | 16 |
| 07-2829 | C. neoformans | 2 | 2 | 16 | 16 | >64 | >64 | 8 | 16 |
| 07-1870 | R. arrhizus | 16 | >64 | 2 | >64 | 4 | >64 | 4 | >64 |

TABLE 4-continued

Antifungal Activity of Compounds 201, 209, 210, and 211.

| | | Compound 201 24 | Compound 201 48 | Compound 209 24 | Compound 209 48 | Compound 210 24 | Compound 210 48 | Compound 211 24 | Compound 211 48 |
|---|---|---|---|---|---|---|---|---|---|
| 07-2044 | R. arrhizus | 4 | >64 | 2 | >64 | 4 | >64 | 4 | >64 |
| 07-2078 | R. arrhizus | >64 | >64 | >64 | >64 | >64 | >64 | 8 | >64 |
| 07-1399 | F. solani | 2 | 4 | >64 | >64 | 1 | >64 | 4 | 8 |
| 07-1755 | F. solani | 2 | >64 | >64 | >64 | 1 | >64 | 4 | 8 |
| 07-1867 | F. solani | 2 | >64 | >64 | >64 | 2 | >64 | 2 | 8 |
| 07-1333 | S. apiospermum | 2 | 2 | 64 | >64 | 1 | >64 | 2 | 4 |
| 07-1502 | S. apiospermum | 2 | 2 | 32 | >64 | 1 | >64 | 2 | 4 |
| 07-1601 | S. apiospermum | 2 | 2 | 8 | >64 | 1 | >64 | 2 | 4 |
| 05-388 | A. fumigatus | 1 | >64 | 16 | >64 | 2 | >64 | 2 | >64 |
| 06-4126 | A. fumigatus | 1 | >64 | 16 | >64 | 2 | >64 | 2 | >64 |
| 07-2039 | A. fumigatus | 1 | >64 | 32 | >64 | 2 | >64 | 2 | >64 |
| 07-1743 | T. rubrum | 1 | 1 | 8 | 8 | 0.25 | 0.5 | <=0.125 | <=0.125 |
| 07-2055 | T. rubrum | 1 | 1 | 8 | 8 | 0.25 | 0.5 | <=0.125 | <=0.125 |

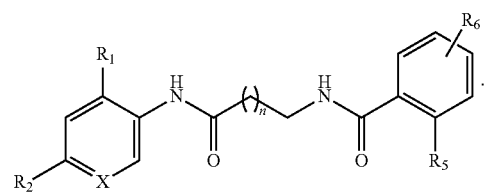

What is claimed is:

1. A compound having the structure

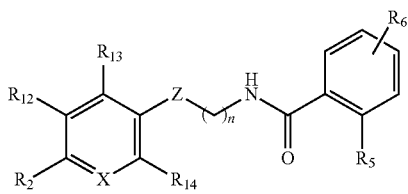

wherein
n is 1-10;
X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;
$R_2$ is H or $NR_3R_4$, wherein $R_3$ and $R_4$ are each independently H or $C_2$-$C_6$ alkyl;
$R_5$ is SH; and
$R_6$, $R_{12}$, $R_{13}$, and $R_{14}$ are each independently H, OH, SH, F, Cl, $SO_2R_{15}$, $NO_2$, trifluoromethyl, methoxy, or CO—$R_{15}$, wherein $R_{15}$ is alkyl, alkenyl, alkynyl, $C_3$-$C_8$ cycloalkyl, or aryl, or
a salt of the compound.

2. The compound of claim 1 having the structure

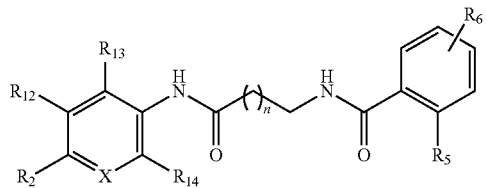

wherein
n is 1-9;
X is C—$R_{11}$ or N, wherein $R_{11}$ is H, OH, SH, F, Cl, $SO_2R_7$, $NO_2$, trifluoromethyl, methoxy, or CO—$R_7$, wherein $R_7$ is alkyl, alkenyl, alkynyl, $C_3$-$C_8$ cycloalkyl, or aryl;
$R_1$ is H;
$R_2$ is H or $NR_3R_4$, wherein $R_3$ and $R_4$ are each independently H, $C_1$-$C_6$ alkyl, or $C_3$-$C_8$ cycloalkyl;
$R_5$ is SH; and
$R_6$, is H, OH, SH, F, Cl, $SO_2R_{15}$, $NO_2$, trifluoromethyl, methoxy, or CO—$R_{15}$, wherein $R_{15}$ is alkyl, alkenyl, alkynyl, $C_3$-$C_6$ cycloalkyl, or aryl.

3. The compound of claim 2,
wherein
n is 3-6;
X is N;
$R_1$ is H;
$R_2$ is H or $NR_3R_4$, wherein $R_3$ and $R_4$ are each independently H, $C_1$-$C_6$ alkyl, or $C_3$-$C_8$ cycloalkyl;
$R_5$ is SH; and
$R_6$ is Cl or methoxy.

4. The compound of claim 3,
wherein
n is 3-6;
X is N;
$R_1$ is H;
$R_2$ is $NR_3R_4$, wherein $R_3$ and $R_4$ are each —H or $C_1$-alkyl;
$R_5$ is SH; and
$R_6$ is Cl or methoxy.

5. The compound of claim 3,
wherein
n is 3-6;
X is C—$R_{11}$, wherein $R_{11}$ is H, OH, SH, Cl, or methoxy;
$R_1$ is H;
$R_2$ is H or $NR_3R_4$, wherein $R_3$ and $R_4$ are each independently H, $C_1$-$C_6$ alkyl, or $C_3$-$C_8$ cycloalkyl;
$R_5$ is SH; and
$R_6$ is Cl or methoxy.

6. The compound of claim 5,
wherein
n is 3-6;
X is C—$R_{11}$, wherein $R_{11}$ is H, OH, SH, Cl, or methoxy;
$R_1$ is H;
$R_2$ is $NR_3R_4$, wherein $R_3$ and $R_4$ are each —H or —$CH_3$;
$R_5$ is SH; and
$R_6$ is Cl or methoxy.

7. The compound of claim 4, wherein n is 4 or 5.

8. The compound of claim 6, wherein n is 4 or 5.

9. The compound of claim 1, wherein the aromatic ring bearing the SH group is an aza, or polyaza-aromatic five- or six-membered ring.

10. A pharmaceutical composition comprising the compound of claim 1 or a pharmaceutically acceptable salt thereof, and a pharmaceutically acceptable carrier.

11. A method for reducing the size of a tumor overexpressing nuclear receptor corepressor (N-CoR) comprising administering to the subject the pharmaceutical composition of claim 10, so as to reduce the size of the tumor.

12. The method of claim 11, wherein the tumor overexpressing nuclear receptor corepressor (N-CoR) is a brain tumor.

13. A method of inhibiting the activity of histone deactylase (HDAC) comprising contacting the HDAC with the compound of claim 1 so as to inhibit the activity of histone deacetylase.

14. The method of claim 13, wherein the HDAC is histone deacetylase 3 (HDAC3) or histone deacetylase 4 (HDAC4).

15. A method of inhibiting HIV replication comprising contacting an HIV-infected cell with the compound of claim 1 so as to inhibit HIV replication.

16. A method of inhibiting cardiac hypertrophy comprising administering to the subject an amount of the compound of claim 1 effective to inhibit cardiac hypertrophy.

17. A method of treating a subject afflicted with breast cancer, colon cancer, large cell lung cancer, adenocarcinoma of the lung, small cell lung cancer, stomach cancer, liver cancer, ovary adenocarcinoma, pancreas carcinoma, prostate carcinoma, promyelocytic leukemia, chronic myelocytic leukemia, or acute lymphocytic leukemia, comprising administering to the subject the pharmaceutical composition of claim 10, thereby treating the subject.

18. A method of inhibiting fungal growth comprising contacting the fungus with the compound of claim 1 so as to inhibit the growth of the fungus.

19. A process for preparing a compound having the structure:

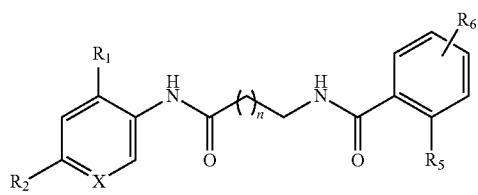

wherein n is 4;

X is C—$R_{11}$ or N, wherein $R_{11}$ is H;

$R_1$ is H;

$R_2$ is H;

$R_5$ is SH; and $R_6$ is H, comprising:

a) contacting the compound having the structure

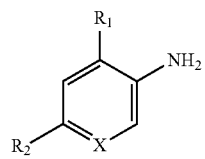

with a compound having the structure

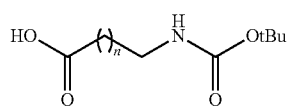

in the presence of one or more suitable first amide bond-forming reagents, a suitable first base, and a suitable first solvent to form the compound having the structure

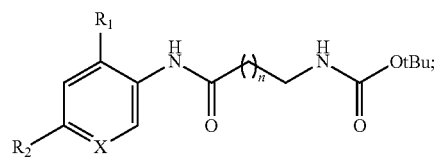

b) exposing the product of step a) to suitable deprotection conditions to form the compound having the structure

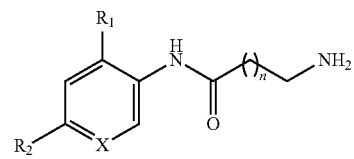

wherein the product is obtained as a free base or salt;

c) contacting the product of step b) with a compound having the structure

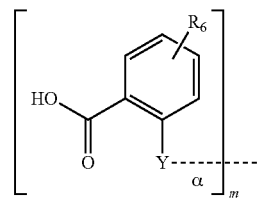

in the presence of one or more suitable second amide bond-forming reagents, a suitable second base, and a suitable second solvent to form the compound having the structure

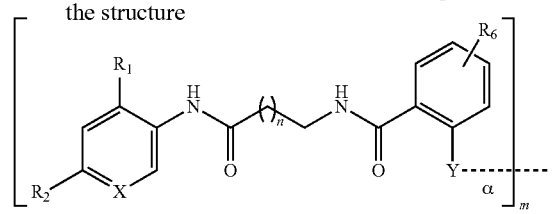

wherein m is 1 or 2, and
when m is 1, then α is absent and Y is SH; or
when in is 2, a is present, and Y is S.

20. The process of claim 19, further comprising
d) reacting the product of step c),
wherein in is 2, α is present, and Y is S,
with zinc, in the presence of hydrochloric acid to obtain the compound having the structure